US011331294B2

(12) United States Patent
Kelley

(10) Patent No.: US 11,331,294 B2
(45) Date of Patent: May 17, 2022

(54) BENZOQUINONE DERIVATIVE E3330 IN COMBINATION WITH CHEMOTHERAPEUTIC AGENTS FOR THE TREATMENT OF BLADDER CANCER

(71) Applicant: Indiana University Research and Technology Corporation, Indianapolis, IN (US)

(72) Inventor: Mark R. Kelley, Zionsville, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 540 days.

(21) Appl. No.: 16/418,276

(22) Filed: May 21, 2019

(65) Prior Publication Data
US 2019/0274988 A1 Sep. 12, 2019

Related U.S. Application Data

(63) Continuation-in-part of application No. 16/044,981, filed on Jul. 25, 2018, now abandoned, which is a continuation of application No. 14/690,973, filed on Apr. 20, 2015, now Pat. No. 10,058,523, which is a continuation of application No. 12/679,824, filed as application No. PCT/US2008/077210 on Sep. 22, 2008, now Pat. No. 9,040,505.

(60) Provisional application No. 60/989,566, filed on Nov. 21, 2007, provisional application No. 60/975,396, filed on Sep. 26, 2007.

(51) Int. Cl.
| | | |
|---|---|---|
| A61K 31/201 | (2006.01) | |
| A61K 31/7068 | (2006.01) | |
| A61K 31/198 | (2006.01) | |
| A61K 31/454 | (2006.01) | |
| A61K 39/395 | (2006.01) | |
| A61K 31/122 | (2006.01) | |
| A61K 45/06 | (2006.01) | |
| A61K 31/282 | (2006.01) | |
| A61K 31/195 | (2006.01) | |
| A61K 31/13 | (2006.01) | |
| A61K 31/203 | (2006.01) | |
| A61K 33/243 | (2019.01) | |

(52) U.S. Cl.
CPC .......... *A61K 31/201* (2013.01); *A61K 31/122* (2013.01); *A61K 31/13* (2013.01); *A61K 31/195* (2013.01); *A61K 31/198* (2013.01); *A61K 31/203* (2013.01); *A61K 31/282* (2013.01); *A61K 31/454* (2013.01); *A61K 31/7068* (2013.01); *A61K 33/243* (2019.01); *A61K 39/3955* (2013.01); *A61K 45/06* (2013.01)

(58) Field of Classification Search
CPC .............. A61K 2300/00; A61K 31/122; A61K 31/198; A61K 31/201; A61K 31/203; A61K 31/454; A61K 31/7068; A61K 33/24; A61K 31/13; A61K 31/195; A61K 31/282; A61K 39/395; A61K 39/3955; A61K 45/06; A61K 31/192; A61P 35/00; A61P 27/02

See application file for complete search history.

(56) References Cited

U.S. PATENT DOCUMENTS

| | | |
|---|---|---|
| 5,210,239 A | 5/1993 | Abe et al. |
| 5,849,793 A | 12/1998 | Pan et al. |
| 5,919,643 A | 7/1999 | Kelley et al. |
| 6,190,661 B1 | 2/2001 | Kelley et al. |
| 6,235,756 B1 | 5/2001 | D'Amato |
| 6,406,917 B1 | 6/2002 | Kelley et al. |
| 2003/0091574 A1 | 5/2003 | Gevas et al. |
| 2003/0229004 A1 | 12/2003 | Zarlilng et al. |
| 2004/0002499 A1 | 1/2004 | Aggarwal |
| 2005/0186208 A1 | 8/2005 | Fyfe et al. |
| 2006/0024691 A1 | 2/2006 | Benz |
| 2010/0297113 A1 | 11/2010 | Kelley et al. |

FOREIGN PATENT DOCUMENTS

| | | |
|---|---|---|
| EP | 0813866 A2 | 12/1997 |
| JP | 07291859 | 7/1995 |
| WO | 200100229 A1 | 1/2001 |

OTHER PUBLICATIONS

Hunter et al., Retinal angiomatous proliferation: clinical characteristics and treatment options; Optometry; Sep. 2004; vol. 75, No. 9, pp. 577-588.

Fayette, J., et al., Use of angiogenesis inhibitors in tumour treatment, European Journal of Cancer, 41/8, pp. 1109-1116, May 1, 2005.

Fishel, M., et al., The DNA base excision repair protein Ape1/Ref.-1 as a therapeutic and chemopreventative target, Molecular Aspects of Medicine, 28/3-4, pp. 375-395, Jun. 2007.

(Continued)

*Primary Examiner* — Jean P Cornet
(74) *Attorney, Agent, or Firm* — Stinson LLP

(57) ABSTRACT

Disclosed are novel methods for the therapeutic treatment of cancer and angiogenesis. The enzyme Ape1/Ref-1, via its redox function, enhances the DNA binding activity of transcription factors that are associated with the progression of cancer. The present disclosure describes the use of agents to selectively inhibit the redox function of Ape1/Ref-1 and thereby reduce tumor cell growth, survival, migration and metastasis. In addition, Ape1/Ref-1 inhibitory activity is shown to augment the therapeutic effects of other therapeutics and protect normal cells against toxicity. Further, Ape1/Ref-1 inhibition is shown to decrease angiogenesis, for use in the treatment of cancer as well other pathologic conditions of which altered angiogenesis is a component.

7 Claims, 59 Drawing Sheets

Specification includes a Sequence Listing.

(56) References Cited

OTHER PUBLICATIONS

Gura, T., Systems for Identifying New Drugs Are Often Faulty, Science, vol. 278, No. 5340, pp. 1041-1042, Nov. 7, 1997.
Kaiser, J., First Pass at Cancer Genome Reveals Complex Landscape, Science, vol. 313, No. 5792, pp. 1370, Sep. 8, 2006.
Kelly et al., Abstracts, 36th Central Regional Meeting of the Amer. Chem. Soc., Jun. 2-4, 2004, Chem. Eng. News, vol. 82 (3), pp. 88, Jan. 19, 2004.
Database WPI Week 1996 Thomson Scientific, London, GB; AN 1996-017132 XP002508298 Goto Masaki et al: "NFkB transcription factor inhibitor"—& JP 07 291859 A (Eisai Co Ltd) Nov. 7, 1995 (Nov. 7, 1995).
Mital, A., et al., Synthesis of novel 2-substituted 1,4-naphthoquinones using Heck reaction in 'green' reaction media Arkivoc Journal, vol. 11, No. ISSN:1424-6376, 2006, pp. 99-106.
Luo, M., et al., Inhibition of the human apurinic/apyrimidic endonuclease DNA base excision repair enzyme/redox factor (APE1/REF-1) using small molecule redox and repair inhibitors: Therapeutic implications, Proceedings of the Annual Meeting of the American Association for Cancer Research, 45/1, pp. 703-704, Mar. 1, 2004.
Macular degeneration, Wikipedia, the free encyclopedia, accessed on Dec. 16, 2013.
Proprionic Acid (MP Biomedicals™—U.S. Appl. No. 15/698,866—Chemical Product Phy. Prop Display—Fisher Scientific, 2014.
Proprionic Acid 79-09-4 (Chemical Book, htp://www.chemicalbook.com/ChemicalProductProperty_EN_CB4138567.htm, 2010.
Jiang, Y., et al., Implications of apurinic/apyrimidinic endonuclease in reactive oxygen signaling response after cisplatin treatment of dorsal root ganglion neurons, Cancer Research / American Association for Cancer Research, Philadelphia, PA. : AACR, vol. 68, No. 15, Aug. 1, 2008 (Aug. 1, 2008), pp. 6425-6434.
Reed, A., et al., Potentiation of melphalan-induced cytotoxicity through targeting of the base excision repair pathway in multiple myeloma, Blood, American Society of Hematology, US, vol. 110, No. 11, Part 2, Nov. 1, 2007 (Nov. 1, 2007), p. 273B.
Uetsuka, K., et al., Protective effects of a novel quinone derivative, E3330, on mouse hepatitis virus (MHV)-induced chronic hepatitis in athymic nude mice, Exp. Anim. vol. 46 (3), pp. 219-223, Jul. 1997.
Saitou Y, et al., (2005) Augmentation of tumor necrosis factor family-induced apoptosis by E3330 in human hepatocellular carcinoma cell lines via inhibition of NF kB. World Journal of Gastroenterology 11 6258-6261.
E3330-PubChem (PubChem Compound http://pubchem.ncbi.nim.nih.gov/summary/summary.cgi?cid=6439397, Apr. 29, 2006.
Van Noort, JM., et al., Cell Biology of Autoimmune Diseases, Int Rev. Cytol., 1998, vol. 178, pp. 127-206.
Goto et al., Inhibitory Effect of E3330, a Novel quinine Derivative Able to Suppress Tumor Necrosis Factor-a Generation, on Activation of Nuclear Factor-kB, Molecular Pharmacology, 49:860-873, 1996.
Kakolyris et al., Human AP endonuclease 1 (HAP1) protein expression in breast cancer correlates with lymph node status and angiogenesis; British Journal of Cancer (1998), vol. 77, No. 7, pp. 1169-1173.
Silvestris et al., Rationale for the use of gemcitabine in breast cancer (Review); International Journal of Oncology; 2004, vol. 24, pp. 389-398.
Toschi et al., Role of gemcitabine in cancer therapy; Drug Evaluation, Future Oncology, 2005, vol. 1, No. 1, pp. 7-17.
Luo et al., Role of the Multifunctional DNA Repair and Redox Signaling Protein Ape1/Ref-1 in Cancer and Endothelial Cells: Small-Molecule Inhibition of the Redox Function of Ape1; Antioxidants & Redox Signaling; pp. 1853-1867.
Nanji et al., Protective Effectsofa Novel Quinone Derivative, (2E)-3-[5-(2,3 dimethoxy-6-methyl-1,4-benzoquinoyl)]-2-nonyl-2-propanoic acid on Experimental Alcoholic Liver Injury, Journal of Pharmacology and Experimental Therapeutics, Aug. 1993, vol. 266, No. 2, pp. 1085-1090.

FIG. 3B
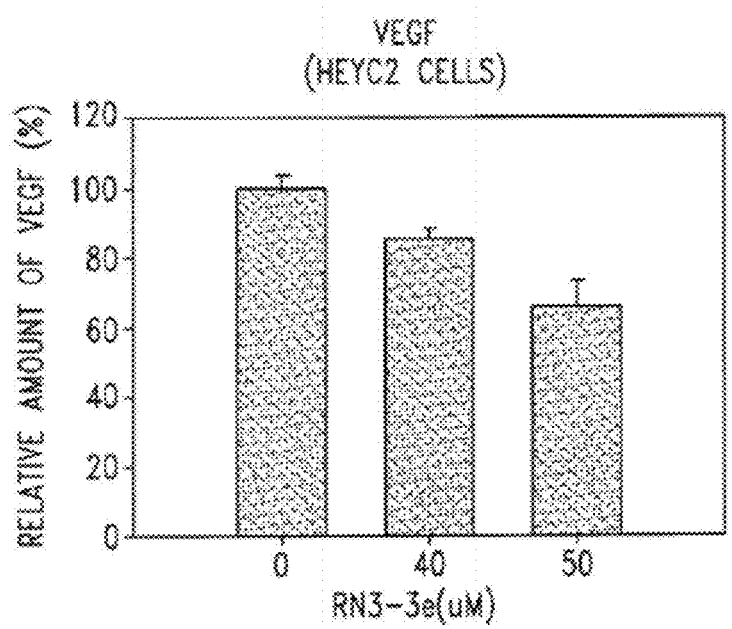
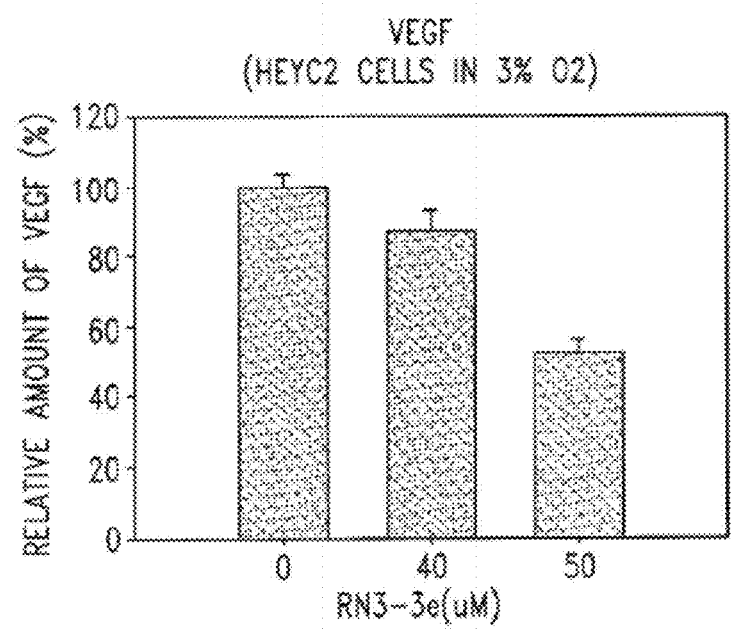

FIG. 4B
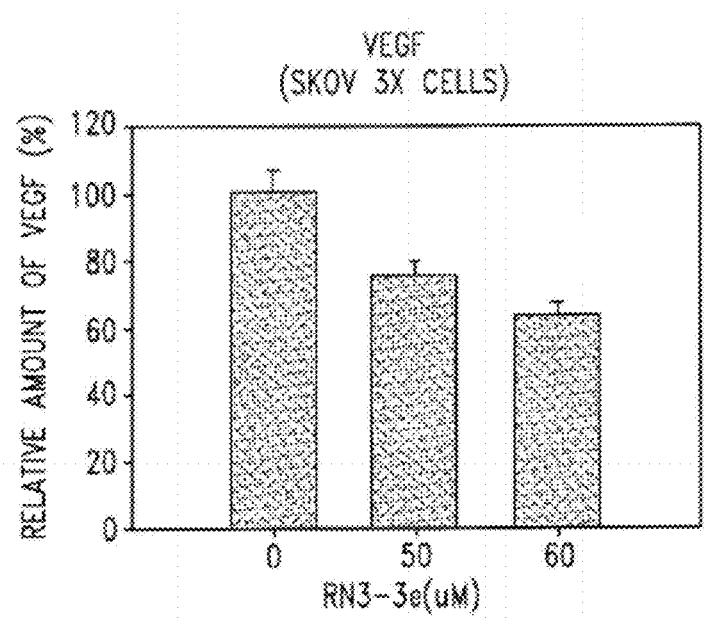
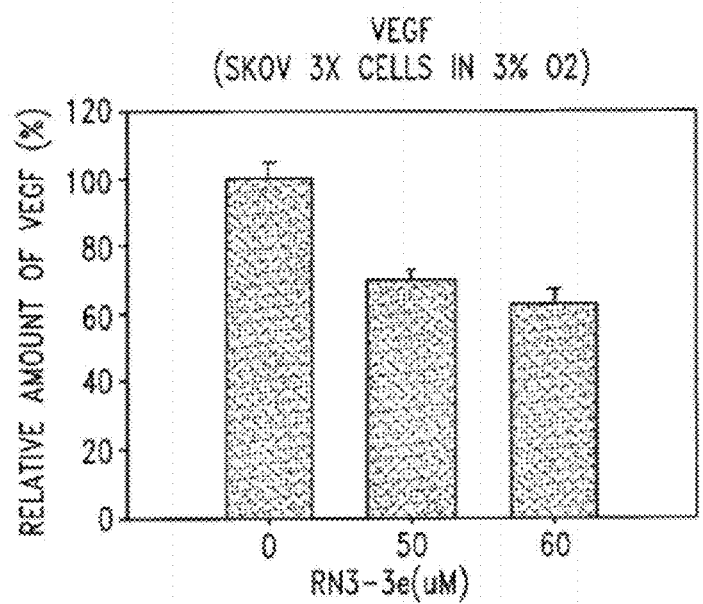

FIG. 10

MTS PROLIFERATION ASSAY:

| | EBM | EBM + bFGF |
|---|---|---|
| CONTROL | 100 ± 11.03467 | 177.41 |
| DMSO CONTROL | 62.41 ± 9.5616 | 144.47 ± 23.1686 |
| 10 µM E3330 | 26.85 ± 8.6409 | 74.01 ± 8.2798 |
| 25 µM 3330 | 6.586 ± 8.4687 | 1.861 ± 3.3570 |
| 50 µM 3330 | 14.84 ± 10.9869 | 2.448 ± 3.6067 |
| 100 µM 3330 | 7.713 ± 1.7757 | 3.462 ± 1.4779 |

P VALUE

| | EBM | EBM + bFGF |
|---|---|---|
| DMSO-10 µM E3330 | 0.001489 | 0.001229 |
| DMSO-25 µM E3330 | 0.000124 | 0.000019 |
| DMSO-50 µM E3330 | <0.001 | <0.001 |
| DSMO-100 µM E3330 | <0.001 | <0.001 |
| 10 µM E3330 - 25 µM3330 | 0.006595 | 0.000003 |

| Survival | | | | | | |
|---|---|---|---|---|---|---|
| Dose of E3330 | | Day 2 | Day 3 | Day 4 | Day 5 | |
| mg/kg | | 19 Sep | 20-Sep | 21-Sep | 22-Sep | |
| 0 | female | 4/4 | 4/4 | 4/4 | 4/4 | |
| | male | 4/4 | 4/4 | 4/4 | 4/4 | |
| 10 | female | 4/4 | 4/4 | 4/4 | 4/4 | |
| | male | 4/4 | 4/4 | 4/4 | 4/4 | |
| 25 | female | 4/4 | 3/4 | 3/4 | 3/4 | |
| | male | 4/4 | 4/4 | 4/4 | 4/4 | |
| 50 | female | 4/4 | 4/4 | 1/4 | 3/4 | |
| | male | 3/4 | 2/4 | 2/4 | 1/4 | |
| 100 | female | 0/6 | N/A | N/A | N/A | |
| | male | 0/1 | | | | |

| Mouse Sample ID | Time (hrs) | E-3330 Peak Area | BMC Peak Area | Area Ratio | Estimated Conc. (ng/mL) | Std. Curve Range | μM | Cage # | Tail mark | Time | Sample ID |
|---|---|---|---|---|---|---|---|---|---|---|---|
| | | | | | | E-3330 | | | | | |
| 2 | 0.5 | 1970000 | 41300 | 47.6998 | 2200 | 0-10000 | 5.8 | 371529 | 1 | 30 | 2 |
| 7 | 1 | 1230000 | 52000 | 23.6538 | 954 | | 2.5 | 371529 | 1111 | 60 | 7 |
| 12 | 2 | 1010000 | 21400 | 47.1963 | 2174 | | 5.7 | 371528 | 111 | 2 | 12 |
| 17 | 4 | 806000 | 52100 | 15.4702 | 476 | 0-3000 | 1.3 | 371529 | 1 | 4 | 17 |
| 22 | 8 | 73500 | 11100 | 6.6216 | 209 | | 0.6 | 371529 | 1111 | 8 | 22 |
| 27 | 24 | 18800 | 27300 | 0.6886 | 16 | 0-30 | 0.041 | 371528 | 111 | 24 | 27 |

FIG. 22

| Group | lambda (hr-1) | $t_{1/2}$ (hr) | Dosage (mg) | Weight (kg) | AUC $_{0-infinity}$ (hr*ng/mL) | | Cl/F | |
|---|---|---|---|---|---|---|---|---|
| | | | | | | mL/hr | L/hr | mL/min |
| All mice | 0.198 | 3.5 | 0.5181 | 0.0207 | 3789 | 136.72 | 0.137 | 2.3 |
| Female | 0.1988 | 3.5 | 0.483 | 0.0193 | 5691 | 84.86 | 0.085 | 1.4 |
| Male | 0.1919 | 3.6 | 0.578 | 0.0231 | 941 | 614.27 | 0.614 | 10.2 |
| Definition of Terms | | | | | | | | |
| $t_{1/2}$ is half-life | | | | | | | | |
| Cl/F is blood clearance divided by the bioavailability of the drug | | | | | | | | |

FIG. 25

EC3330 held constant and RA varying dosages

| CELLS | CD11 EXP 03607 day 4 | day 6 |
|---|---|---|
| WT HL60 EtOH | 7 | 4 |
| 25uM E3330 | 11 | 13 |
| 10-5M RA | 140 | 185 |
| 10-5M RA+25uM E3330 | 280 | 390 |
| 10-6M RA | 150 | 223 |
| 10-6M RA+25uM E3330 | 246 | 409 |
| 10-7M RA | 140 | 212 |
| 10-7M RA+25uM E3330 | 147 | 309 |
| 10-8M RA | 100 | 124 |
| 10-8M RA+25uM E3330 | 130 | 248 |
| 10-9M RA | 35 | 21 |
| 10-9M RA+25uM E3330 | 31 | 35 |

RA+E330 yields approximately a 2 fold increase in cellular differentiation compared to the same concentration of RA alone. You can achieve the same amount of differentiation with 1000 fold lower dose. (Compare numbers for 10-5M RA and 10-8M RA+25 uM E3330.)

FIG. 26

| CELLS | Annexin: (UR+LR) | |
|---|---|---|
| | Exp 03607 | |
| | day4 | day6 |
| WT HL60 EtOH | 4 | 4 |
| 25uM E3330 | 7 | 15 |
| 10-5M RA | 15 | 37 |
| 10-5M RA+25uM E3330 | 28 | 66 |
| 10-6M RA | 15 | 36 |
| 10-6M RA+25uM E3330 | 18 | 50 |
| 10-7M RA | 15 | 27 |
| 10-7M RA+25uM E3330 | 14 | 34 |
| 10-8M RA | 14 | 20 |
| 10-8M RA+25uM E3330 | 15 | 31 |
| 10-9M RA | 7 | 10 |
| 10-9M RA+25uM E3330 | 11 | 27 |

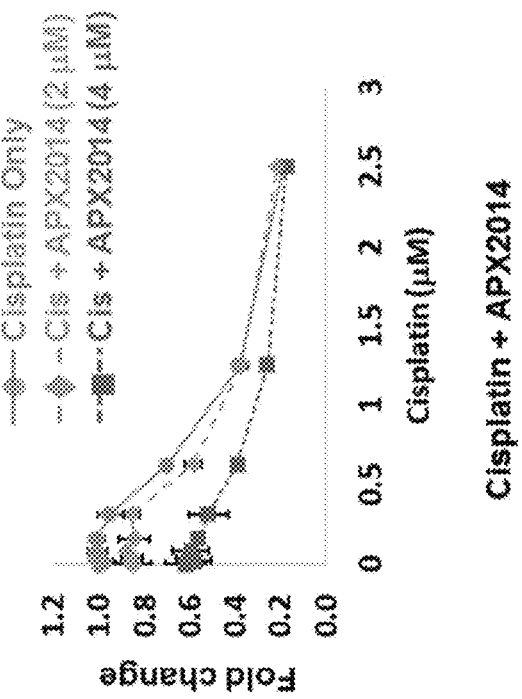
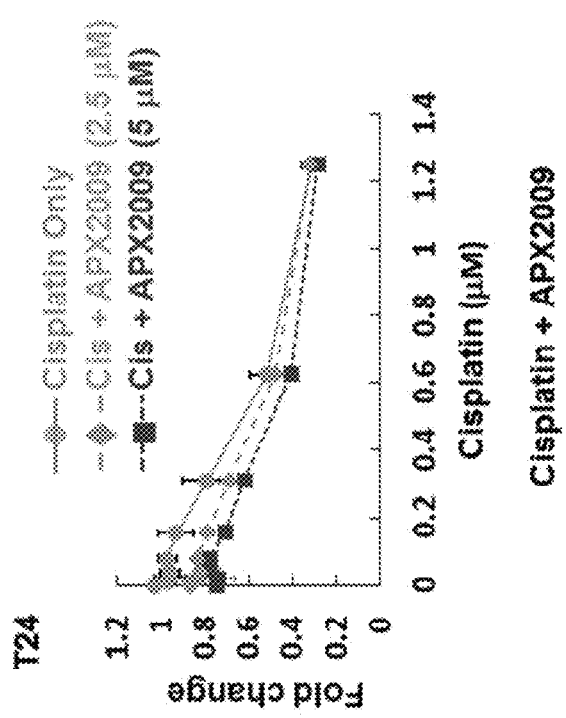
FIG. 30C

BENZOQUINONE DERIVATIVE E3330 IN COMBINATION WITH CHEMOTHERAPEUTIC AGENTS FOR THE TREATMENT OF BLADDER CANCER

CROSS REFERENCE TO RELATED APPLICATIONS

This is a Continuation-in-Part Application of U.S. patent application Ser. No. 16/044,981 filed on Jul. 25, 2018, which is a Continuation Application of U.S. patent application Ser. No. 14/690,973 (now U.S. Pat. No. 10,058,523) filed on Apr. 20, 2015, which is a Continuation Application of U.S. patent application Ser. No. 12/679,824 (now U.S. Pat. No. 9,040,505) filed on Jul. 6, 2010, which is a U.S. national counterpart application of international application serial No. PCT/US2008/077210 filed on Sep. 22, 2008, which claims priority to U.S. Provisional Patent Application No. 60/975,396 filed on Sep. 26, 2007 and to U.S. Provisional Patent Application No. 60/989,566 filed on Nov. 21, 2007, each of which is incorporated by reference herein in its entirety.

INCORPORATION OF SEQUENCE LISTING

A paper copy of the Sequence Listing and a computer readable form of the Sequence Listing containing the file named "2008-020-42_ST25.txt", which is 947 bytes in size (as measured in MICROSOFT WINDOWS® EXPLORER), are provided herein and are herein incorporated by reference. This Sequence Listing consists of SEQ ID NOs:1-2.

FIELD OF THE DISCLOSURE

The present disclosure relates generally to the fields of molecular biology, biochemistry, and pathology. More specifically, in certain aspects, the disclosure relates to the use of Ape1/Ref-1 redox inhibitors in the treatment of cancer, and in particular, bladder cancer, and for inhibition of angiogenesis.

BACKGROUND OF THE DISCLOSURE

Bladder cancer is the fourth most common malignancy and eighth leading cause of cancer-related death of men in the United States and the ninth most common cancer worldwide, with an estimated 430,000 new cases and 165,000 deaths annually. Twenty-three percent of bladder cancer patients die within 5 years of diagnosis from the disease. Although cisplatin is used routinely in treating bladder cancers, refractory diseases remains lethal for many patients. The recent addition of immunotherapy has improved patient outcomes, however, a large cohort of patients do not respond to these treatments. Further, in the last 5 years, there has been the development of PD-1/PD-L1 immunotherapy that has led to a 20-30% response in cisplatin refractory disease. Therefore, identification of innovative molecular targets for bladder cancer is crucial.

Apurinic/apyrimidic endonuclease (Ape 1), also known as redox effector factor (Ref-1) (hereinafter Ape1/Ref-1), is an enzyme with a dual role. In addition to its DNA base excision repair (BER) activity, Ape1/Ref-1 also functions as a redox effector maintaining transcription factors in an active reduced state (see FIG. 1).

Ape1/Ref-1 has been shown to stimulate the DNA binding activity of several transcription factors such as HIF-1α, NFκB, AP-1 and p53, STATS, and others known and unknown, which are related to tumor survival and progression (Evans et al., Mutat Res 2000, 461, 83). Ape1/ref-1 expression has been shown to be altered in a variety of cancers including breast, cervical, germ cell tumors, adult and pediatric gliomas, osteosarcomas, rhabdomyosarcomas, non-small cell lung cancer, and multiple myeloma (Puglisi et al., Oncol Rep 2002, 9, 11; Thomson et al., Am J Pediatr Hematol Oncol 2001, 23, 234; Roberston et al., Cancer Res 2001, 61, 2220; Puglisi et al., Anticancer Res 2001, 21, 4041; Koukourakis et al., Int J Radiat Oncol Biol Phys 2001, 50, 27; Kakolyris et al., Br J Cancer 1998, 77, 1169; Bobola et al., Clin Cancer Res 2001, 7, 3510). High Ape1/Ref-1 expression has also been associated with a poor outcome for chemoradiotherapy, poor complete response rate, shorter local relapse-free interval, poorer survival, and high angiogenesis (Koukourakis et al., Int J Radiat Oncol Biol Phys 2001, 50, 27; Kakolyris et al., Br J Cancer 1998, 77, 1169; Bobola et al., Clin Cancer Res 2001, 7, 3510).

Angiogenesis is an important component of cancer growth, survival, migration, and metastasis. The formation of new blood vessels at the site of a cancerous tumor provides a source of nutrients for accelerated tumor growth and expansion as well as a path for tumor cells to enter the bloodstream and spread to other parts of the body. Thus, effective inhibition of angiogenesis is a useful mechanism to slow or prevent the growth and spread of cancer. An increase in Ape1/Ref-1 activity has been associated with angiogenesis. Vascular endothelial growth factor (VEGF) is an important signaling protein involved in both vasculogenesis and angiogenesis. Ape1/Ref-1 is a component of the hypoxia-inducible transcriptional complex formed on the vascular endothelial growth factor (VEGF) gene's hypoxic response element (Ziel et al., Faseb J 2004, 18, 986).

In addition to cancer, altered angiogenesis contributes to pathological conditions related to, among others, cardiovascular disease, chronic inflammatory disease, rheumatoid arthritis, diabetic retinopathy, degenerative maculopathy, retrolental fibroplasias, idiopathic pulmonary fibrosis, acute adult respiratory distress syndrome, asthma, endometriosis, psoriasis, keloids, and systemic sclerosis. Inhibition of angiogenesis is a desirable clinical outcome for the amelioration or prevention of diseases involving excessive angiogenesis.

SUMMARY OF THE DISCLOSURE

Targeted inhibition of the redox function of Ape1/Ref-1 is a novel approach to the treatment of cancer and angiogenesis. In one embodiment, the present disclosure is directed to the use of anticancer therapeutic agents that inhibit the redox function of Ape1/Ref-1. In another embodiment, the present disclosure is directed to anti-angiogenic agents that inhibit the redox function of Ape1/Ref-1. In yet other embodiments, the present disclosure is directed to combinations of agents that inhibit the redox function of Ape1/Ref-1 and other chemotherapeutic agents.

In one particular aspect, the present disclosure is directed to a method for inhibiting bladder cancer associated with altered angiogenesis. The method comprises administering to a subject in need thereof an effective amount of an APE1/Ref-1 inhibitor selected from the list of Table 1, pharmaceutically acceptable salts and pharmaceutically acceptable solvates thereof, and combinations thereof, which selectively inhibits the redox function of Ape1/Ref-1.

In another aspect, the present disclosure is directed to a method for inhibiting bladder cancer. The method comprises administering to a subject in need thereof an effective amount of an APE1/Ref-1 inhibitor selected from the list of Table 1, pharmaceutically acceptable salts and pharmaceutically acceptable solvates thereof, and combinations thereof, which selectively inhibits the redox function of Ape1/Ref-1 and inhibits tumor cell growth.

BRIEF DESCRIPTION OF THE DRAWINGS

FIGS. 3A & 3B. VEGF ELISA Assay.

FIGS. 4A & 4B. VEGF ELISA Assay.

FIG. 10. MTS Proliferation Assay with retinal endothelial cell proliferation in cells treated with or without basic fibroblast growth factor (bFGF).

FIG. 20. Survival data of mice treated with RN3-3 (APX3330) at various amounts and observed on days 2, 3, 4 or 5 after treatment.

FIGS. 21A & 21B. Pharmacokinetic data of APX3330 (RN3-3) over a 24 hr time course experiment.

FIG. 22. Pharmacokinetic data for APX3330 (RN3-3).

FIG. 25. Effect of RN3-3 (APX3330) and various doses of RA.

FIG. 26. Effect of APX3330 (RN3-3) and RA on HL-60 cells undergoing apoptosis (annexin/PI assay).

(FIG. 28G *-p<0.05, ANOVA). Established bladder cancer lines exhibit significantly higher expression than the benign HUC cell line.

FIGS. 30A-30C. Combination treatment with cisplatin and APX inhibitors resulted in an enhancement of cisplatin-induced cytotoxicity. RP-B-01, RP-B-02, and T24 cell lines were treated with increasing concentrations of cisplatin in combination with a single dose of either APX2009 or APX2014 as indicated (n=3±SE). Cell proliferation was normalized to Saline control and expressed as Fold Change. Combination index (CI) values calculated with Compusyn for combination of APX inhibitors and cisplatin. CI values indicated mainly additivity (0.95-1.2) to synergy (0.8-0.94).

DETAILED DESCRIPTION

Figure 1:
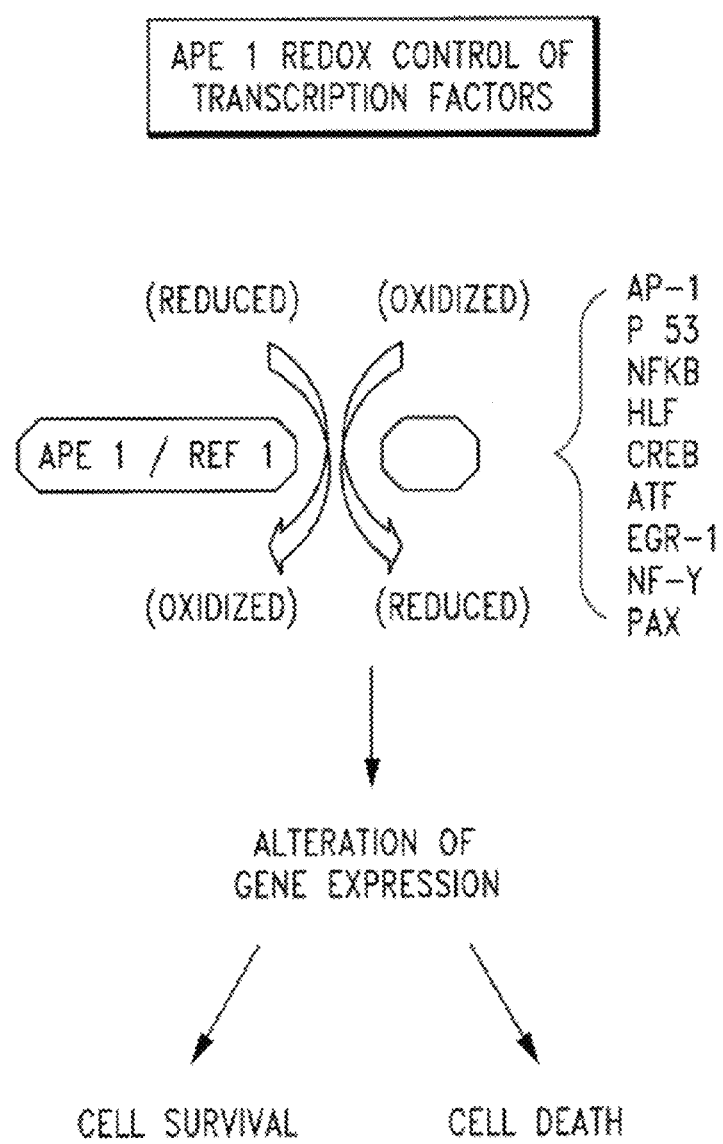
FIG. 1. Redox role of Ape1/Ref-1 in the regulation of transcription factors important in tumor survival.

The present disclosure is directed to the use of anti-cancer and anti-angiogenic agents that selectively inhibit the redox function of Ape1/Ref-1. Such selective inhibition includes specific inhibition, or, in other words, where there is no or no appreciable effect on the BER function of APE1/Ref-1, as well as where the predominant effect is on the redox function, vis-a-vis the BER function. Also encompassed by the disclosure is the use of such agents in combination with additional chemotherapeutic/therapeutic agents. It is desired that the other agents work on a subject in a different way to that of the agents which selectively inhibit the redox function of Ape1/Ref1.

Physiological disorders associated with altered angiogenesis encompass those disorders associated with inappropriate angiogenesis, which are directly or indirectly deleterious to the subject. Altered angiogenesis contributes to pathological conditions related to, among others, cancer (including growth, survival, migration, microenvironment, and metastasis), and cardiovascular disease, chronic inflammatory disease, rheumatoid arthritis, diabetic retinopathy, degenerative maculopathy, retrolental fibroplasias, idiopathic pulmonary fibrosis, acute adult respiratory distress syndrome, asthma, endometriosis, psoriasis, keloids, and systemic sclerosis.

The term subject includes vertebrate animals, and preferably is a human subject. The term inhibit, and derivatives thereof, includes its generally accepted meaning, which includes prohibiting, preventing, restraining, and slowing, stopping, or reversing progression or severity. Thus, the present methods include both medical therapeutic and prophylactic administration, as appropriate. As such, a subject in need thereof, as it relates to the therapeutic uses herein, is one identified to require or desire medical intervention. An effective amount is that amount of an agent necessary to inhibit the pathological diseases and disorders herein described. When at least one additional therapeutic agent is administered to a subject, such agents may be administered sequentially, concurrently, or simultaneously, in order to obtain the benefits of the agents.

The redox function of Ape1/Ref-1 was found to be selectively inhibited by 3-[(5-(2,3-dimethoxy-6-methy11,4-benzoquinoyl)]-2-nonyl-2-proprionic acid, below (hereinafter "APX3330", also referred to as "RN3-3" or "E3330" or "3330" in this application).

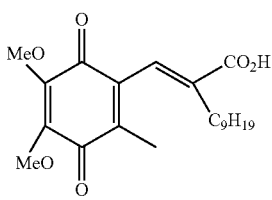

Interestingly, the research indicates that selective blocking of the redox function of Ape1/Ref-1 does not cause any or any appreciable apoptosis in normal cells. One very well might expect that the selective blocking resulting in increased apoptosis in cancerous cells would also impair normal cells. However, this has not been found to be the case.

Other suitable selective redox Ape1/Ref-1 inhibitors for use in the present disclosure include analogues of APX3330, including for example, [(2E)-2-[(3-methoxy-1,4-dioxo-1,4-dihydronaphthalen-2-yl)methylidene]-N,N-diethylpentanamide] (hereinafter "APX2009"), (2E)-2-[(3-methoxy-1,4-dioxo-1,4-dihydronapthalen-2-yl)methylidene]-N,N-dimethylpentanamide] (hereinafter "APX2007"), (2E)-2-[(3-methoxy-1,4-dioxo-1,4-dihydronapthalen-2-yl)methylidene]-N-methoxypentanamide] (hereinafter "APX2014"), (2E)-2-(3-methoxy-1,4-dioxo-1,4-dihydronaphthalen-2-yl)-N,N,2-trimethylprop-2-enamide (hereinafter "APX2032")). Additional suitable analogs are shown below and in Table 1. Further information on APX3330 may be found in Abe et al., U.S. Pat. No. 5,210,239, and information on APX2009 may be found in Kelley et al., J Pharmacol Exp Ther. 2016 November, 359(2): 300-309, each incorporated herein by reference to the extent they are consistent herewith. Particularly, processes for preparing, formulations, and pharmaceutically acceptable salts are described.

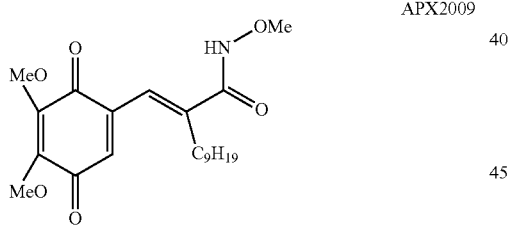

APX2009

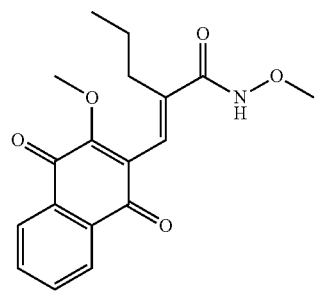

APX2014

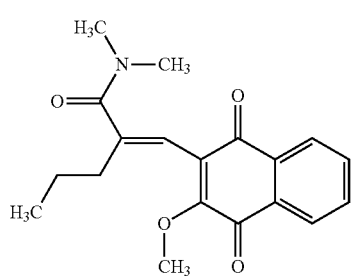

APX2007

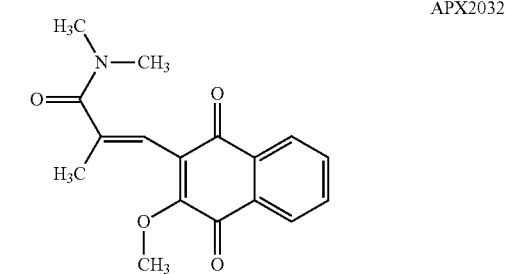

APX2032

TABLE 1

| COMPOUND ID | $R_1$ | X | C(=O)Y | $R_2$ | $R_3$ | $R_4$ | $R_5$ | $R_6$ | EF | MW |
|---|---|---|---|---|---|---|---|---|---|---|
| APX3330 | $CH_3$ | $CH=CR_2$ | OH | $C_9H_{19}$ | =O | MeO | MeO | =O | $C_{21}H_{30}O_6$ | 378.459 |
| APX2006 | MeO | $CH=CR_2$ | NMe | $C_3H_7$ | =O | napthoquinone | | =O | $C_{18}H_{19}NO_4$ | 313.353 |
| APX2007 | MeO | $CH=CR_2$ | $N(Me)_2$ | $C_3H_7$ | =O | napthoquinone | | =O | $C_{19}H_{21}NO_4$ | 327.38 |
| APX2008 | MeO | $CH=CR_2$ | NEt | $C_3H_7$ | =O | napthoquinone | | =O | $C_{19}H_{21}NO_4$ | 327.38 |
| APX2009 | MeO | $CH=CR_2$ | $N(Et)_2$ | $C_3H_7$ | =O | napthoquinone | | =O | $C_{21}H_{25}NO_4$ | 355.428 |
| APX2010 | CH3 | $CH=CR_2$ | $NCH_3$ | $C_4H_9$ | =O | napthoquinone | | =O | $C_{17}H_{23}NO_3$ | 321.373 |
| APX2011 | CH3 | $CH=CR_2$ | $N(CH_3)_2$ | $C_4H_9$ | =O | napthoquinone | | =O | $C_{20}H_{23}NO_3$ | 325.408 |
| APX2012 | $CH_3$ | $CH=CR_2$ | $NCH_2CH_3$ | $C_4H_9$ | =O | napthoquinone | | =O | $C_{20}H_{23}NO_3$ | 325.408 |
| APX2013 | $CH_3$ | $CH=CR_2$ | $N(Et)_2$ | $C_4H_9$ | =O | napthoquinone | | =O | $C_{22}H_{27}NO_3$ | 353.462 |
| APX2014 | MeO | $CH=CR_2$ | NOMe | $C_3H_7$ | =O | napthoquinone | | =O | $C_{18}H_{19}NO_5$ | 329.352 |
| APX2015 | $CH_3$ | $CH=CR_2$ | N-cPro | $C_4H_9$ | =O | napthoquinone | | =O | $C_{21}H_{23}NO_3$ | 337.419 |
| APX2016 | $CH_3$ | $CH=CR_2$ | NOMe | $C_4H_9$ | =O | napthoquinone | | =O | $C_{19}H_{21}NO_4$ | 327.38 |
| APX2017 | $CH_3$ | $CH=CR_2$ | N-Et-Pip | $C_4H_9$ | =O | napthoquinone | | =O | $C_{24}H_{30}N_2O_3$ | 394.515 |
| APX2018 | $CH_3$ | $CH=CR_2$ | N-cHexyl | $C_4H_9$ | =O | napthoquinone | | =O | $C_{24}H_{29}NO_3$ | 379.492 |
| APX2019 | $CH_3$ | $CH=CR_2$ | 2-Piperdone | $C_4H_9$ | =O | napthoquinone | | =O | $C_{22}H_{24}N_2O_4$ | 380.444 |
| APX2020 | $CH_3$ | $CH=CR_2$ | N(Me)OMe | $C_4H_9$ | =O | napthoquinone | | =O | $C_{20}H_{23}NO_4$ | 341.407 |

TABLE 1-continued

| COMPOUND ID | $R_1$ | X | C(=O)Y | $R_2$ | $R_3$ | $R_4$ | $R_5$ | $R_6$ | EF | MW |
|---|---|---|---|---|---|---|---|---|---|---|
| APX2021 | $CH_3$ | $CH=CR_2$ | E-Morpholino | $C_4H_9$ | =O | napthoquinone | | =O | $C_{22}H_{25}NO_4$ | 367.445 |
| APX2022 | $CH_3$ | $CH=CR_2$ | Z-Morpholino | $C_4H_9$ | =O | napthoquinone | | =O | $C_{22}H_{25}NO_4$ | 367.445 |
| APX2023 | $CH_3$ | $CH=CR_2$ | $NH_2$ | $C_4H_9$ | =O | napthoquinone | | =O | $C_{18}H_{19}NO_3$ | 297.348 |
| APX2024 | $CH_3$ | $CH=CR_2$ | E—$NCH_2CH_2OMe$ | $C_4H_9$ | =O | napthoquinone | | =O | $C_{21}H_{25}NO_4$ | 355.434 |
| APX2025 | $CH_3$ | $CH=CR_2$ | Z—$NCH_2CH_2OMe$ | $C_4H_9$ | =O | napthoquinone | | =O | $C_{21}H_{25}NO_4$ | 355.434 |
| APX2026 | Cl | $CH=CR_2$ | NOMe | $C_3H_7$ | =O | napthoquinone | | =O | $C_{17}H_{16}ClNO_4$ | 333.77 |
| APX2027 | Cl | $CH=CR_2$ | $N(Et)_2$ | $C_3H_7$ | =O | napthoquinone | | =O | $C_{20}H_{22}ClNO_3$ | 359.85 |
| APX2028 | OH | $CH=CR2$ | OH | $C_3H_7$ | =O | napthoquinone | | =O | $C16H14O5$ | 286.283 |
| APX2029 | MeO | $CH=CR_2$ | $N(Et)_2$ | $C_3H_7$ | =O | napthoquinone | | =O | $C_{21}H_{25}NO_4$ | 355.434 |
| APX2030 | Me | $CH=CR_2$ | $N(Me)_2$ | $C_3H_7$ | =O | napthoquinone | | =O | $C_{19}H_{21}NO_3$ | 311.381 |
| APX2031 | MeO | $CH=CR_2$ | $NCH_3$ | $CH_3$ | =O | napthoquinone | | =O | $C_{16}H_{15}NO_4$ | 285.295 |
| APX2032 | MeO | $CH=CR_2$ | $N(CH_3)_2$ | $CH_3$ | =O | napthoquinone | | =O | $C_{17}H_{17}NO_4$ | 299.321 |
| APX2033 | MeO | $CH=CR_2$ | OH | $CH_3$ | =O | napthoquinone | | =O | $C_{15}H_{12}O_5$ | 272.253 |
| APX2034 | MeO | $CH=CR_2$ | OH | $C_3H_7$ | =O | napthoquinone | | =O | $C_{17}H_{16}O_5$ | 300.306 |
| APX2043 | MeO | $CH=CR_2$ | $N(CH_3)_2$ | $C_3H_7$ | OH | napthoquinone | | OH | $C_{19}H_{25}NO_4$ | 331.412 |
| APX2044 | $CF_3O$ | $CH=CR_2$ | $N(Et)_2$ | $C_3H_7$ | =O | napthoquinone | | =O | $C_{21}H_{22}F_3NO_4$ | 409.405 |
| APX2045 | $CH_3$ | $CH=CR_2$ | $N(Et)_2$ | $C_3H_7$ | =O | napthoquinone | | =O | $C_{21}H_{25}NO_3$ | 339.435 |
| APX2046 | $CH_3$ | $CH=CR_2$ | $N(Et)_2$ | $CF_3CH_2CH_2$ | =O | napthoquinone | | =O | $C_{21}H_{22}F_3NO_3$ | 393.406 |
| APX2047 | $CH_3$ | $CH=CR_2$ | $N(Et)_2$ | $C_3H_7$ | $OCH_3$ | napthoquinone | | $OCH_3$ | $C_{23}H_{31}NO_3$ | 369.505 |
| APX2048 | $CH_3$ | $CH=CR_2$ | $NOCH_3$ | $C_9H_{19}$ | =O | MeO | MeO | =O | $C_{23}H_{31}NO_4$ | 397.515 |
| APX2049 | $CH_3$ | $CH=CR_2$ | $N(CH_3)CC(O)C(O)C(O)C(O)COH$ | $C_9H_{19}$ | =O | MeO | MeO | =O | $C_{28}H_{45}NO_{10}$ | 555.665 |
| APX2050 | $CH_3$ | $CH=CR_2$ | $N(CH_3)OCH_3$ | $C_9H_{19}$ | =O | MeO | MeO | =O | $C_{23}H_{35}NO_6$ | 421.534 |

Where subject applications are contemplated, particularly in humans, it will be necessary to prepare pharmaceutical compositions in a form appropriate for the intended application. Generally, this will entail preparing compositions that are essentially free of impurities that could be harmful to a subject.

The agents can be administered orally, intravenously, intramuscularly, intrapleurally or intraperitoneally at doses based on the body weight and degree of disease progression of the subject, and may be given in one, two or even four daily administrations.

One will generally desire to employ appropriate salts and buffers to render agents stable and allow for uptake by target cells. Aqueous compositions of the present disclosure comprise an effective amount of the agent, dissolved or dispersed in a pharmaceutically acceptable carrier or aqueous medium. Such compositions also are referred to as innocuously. The phrase pharmaceutically or pharmacologically acceptable refers to molecular entities and compositions that do not produce adverse, allergic, or other untoward reactions when administered to a subject. As used herein, pharmaceutically acceptable carrier includes any and all solvents, dispersion media, coatings, antibacterial and antifungal agents, isotonic and absorption delaying agents and the like. The use of such media and agents for pharmaceutically active sub-stances is well known in the art. Supplementary active ingredients also can be incorporated into the compositions.

Compositions for use in the present disclosure may include classic pharmaceutical preparations. Administration of these compositions according to the present disclosure will be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically accept-able compositions, described supra.

For example, the compounds can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as calcium carbonate and sodium bicarbonate; agents for retarding dissolution such as paraffin; resorption accelerators such as quaternary ammonium com-pounds; surface active agents such as cetyl alcohol, glycerol monostearate; adsorptive carriers such as kaolin and bentonite; and lubricants such as talc, calcium and magnesium stearate, and solid polyethyl glycols.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

For oral administration agents of the present disclosure may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including gels, pastes, powders and slurries. The active ingredient may be added in a therapeutically effective amount to a paste dentifrice that may include water, binders, abrasives, flavoring agents, foaming agents, and humectants.

The compositions for use in the present disclosure may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, general safety and purity standards as required by FDA and foreign counterpart agencies.

In some embodiments, the APE1/Ref-1 inhibitor is APX3330 and is administered in an effective amount of from about 10 μM to about 100 μM. In other embodiments, the APE1/Ref-1 inhibitor is APX2009 and is administered in an effective amount of from about 1 μM to about 50 μM. In still other embodiments, the APE1/Ref-1 inhibitor is APX2014 and is administered in an effective amount of from about 1 μM to about 50 μM.

Inhibition of the redox function of Ape1/Ref-1 was shown to decrease VEGF release, impair capillary tube formation, and inhibit the growth of large cell number colonies, indicating anti-angiogenic activity. Particularly, the Ape1/Ref-1 protein plays a critical role in transcription factor function by regulating the redox signaling of transcription factors (TFs) via reduction of cysteine residues that affect the ability of TFs to bind to DNA and activate gene expression. Additionally, APE1/Ref-1 has been shown to interact with NPM1, directly acting upon RNA quality control mechanisms. Subsequently, APE1/Ref-1 protein performs multiple major functions in cells that affect a number of cellular processes including cell proliferation and cell survival.

Two of the primary TF targets of APE/Ref-1 redox regulation are the ubiquitous factors NFκB and STAT3. These two central transcription factors have been shown to regulate proliferation and survival in multiple cancers, as well as playing a role in cancer progression, signaling within the microenvironment, and resistance to chemotherapy. NFκB and STAT3 has dynamic effects on cancer cells, and targeting APE/Ref-1 as a master regulator of the activity of these pathways is a promising approach in cancer therapy.

The following examples are for illustrative purposes only and are not intended to limit the scope of the present disclosure.

Figure 2:
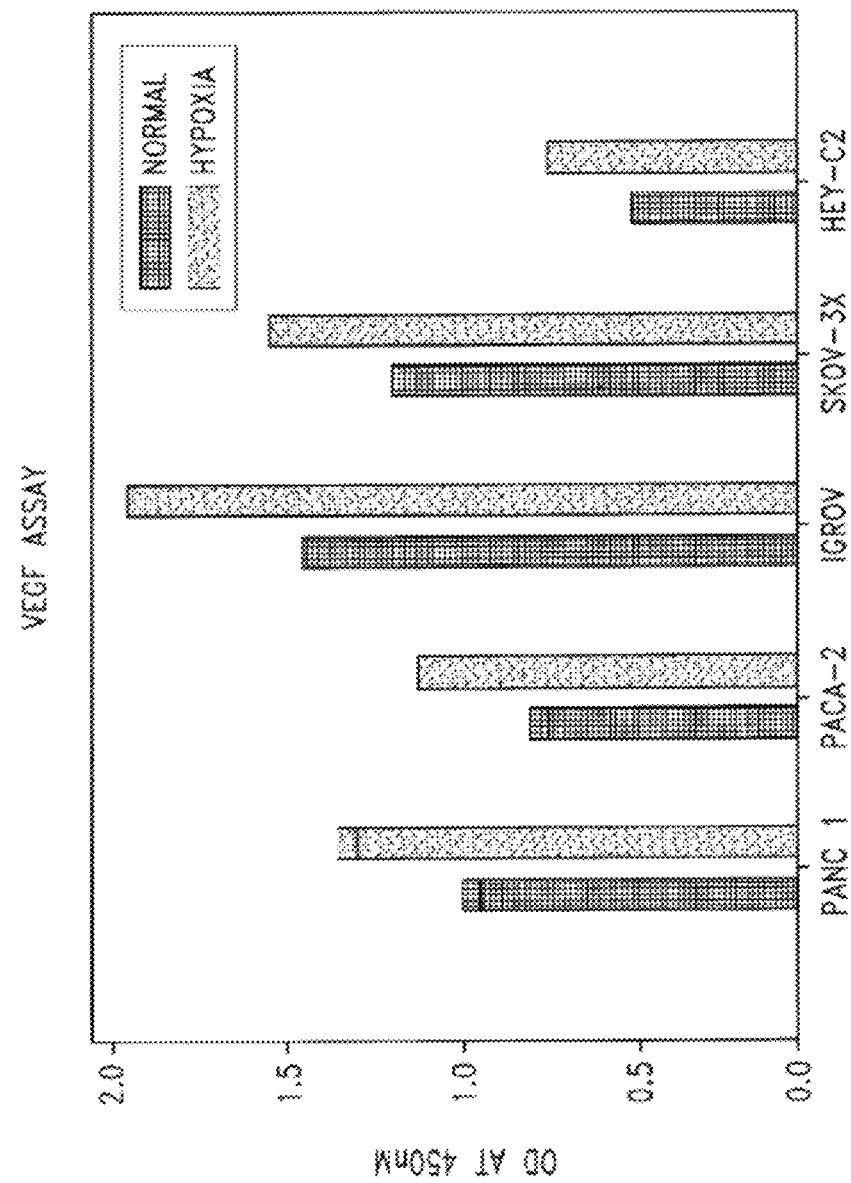
FIG. 2. VEGF enzyme-linked immunosorbent assay (ELISA).
Figure 3A:
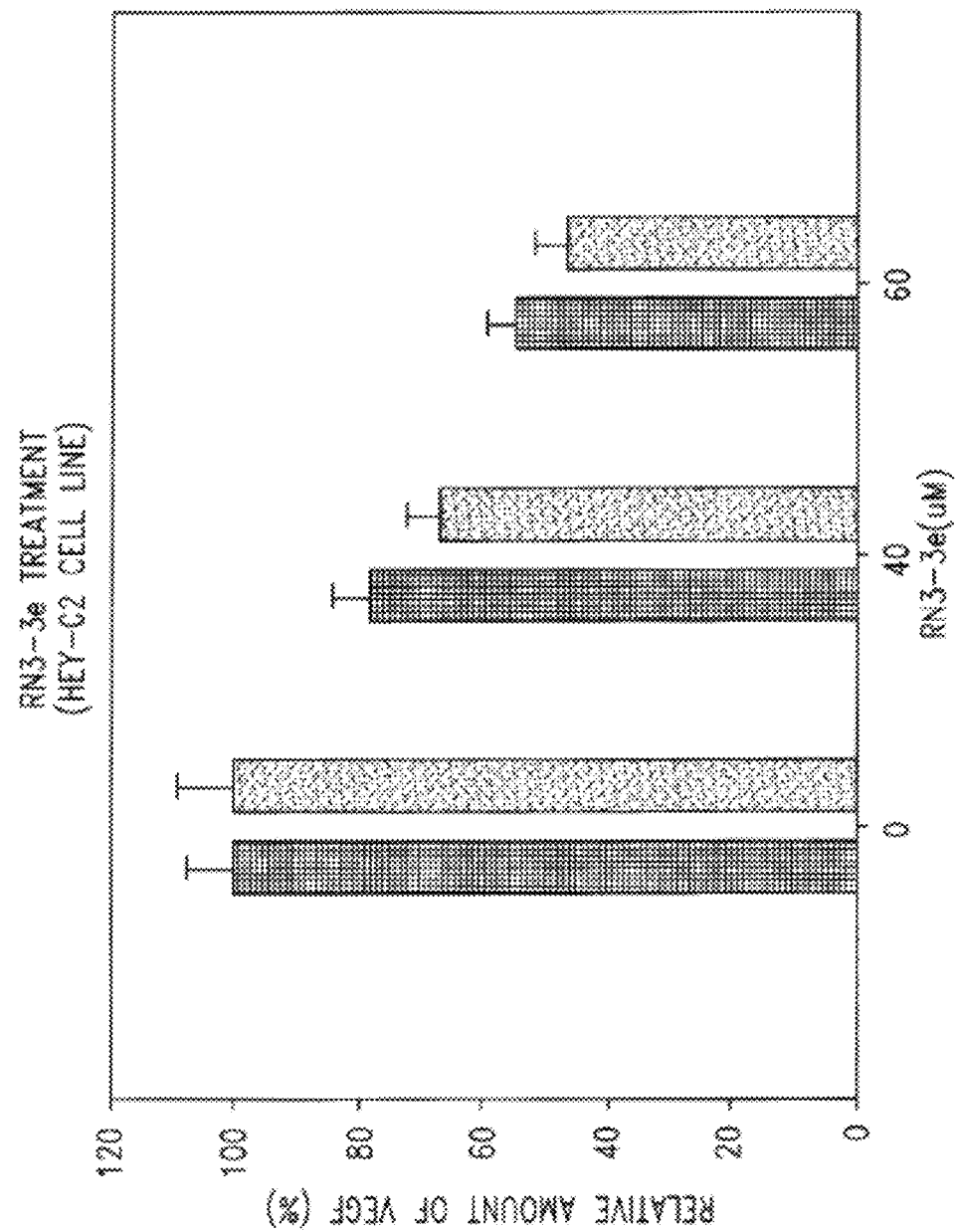
Figure 4A:
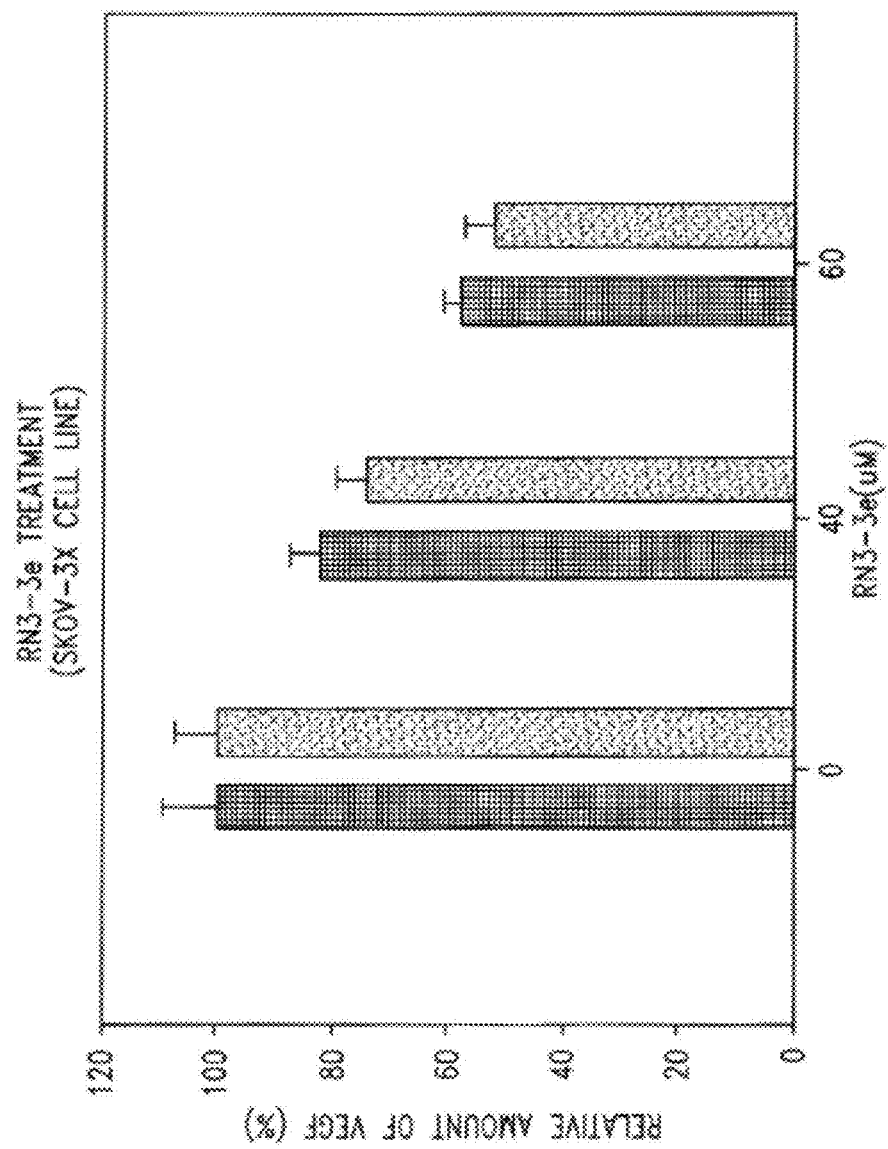
Figure 5:
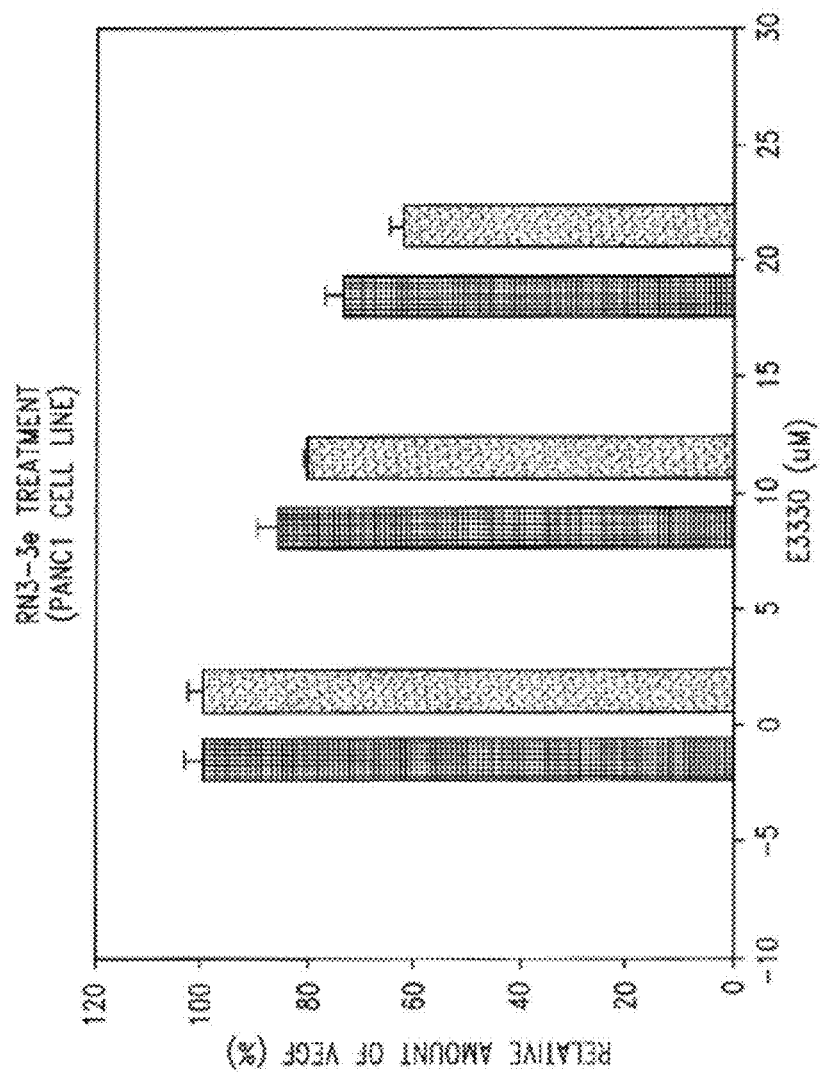
FIG. 5. VEGF ELISA Assay.
Figure 6:
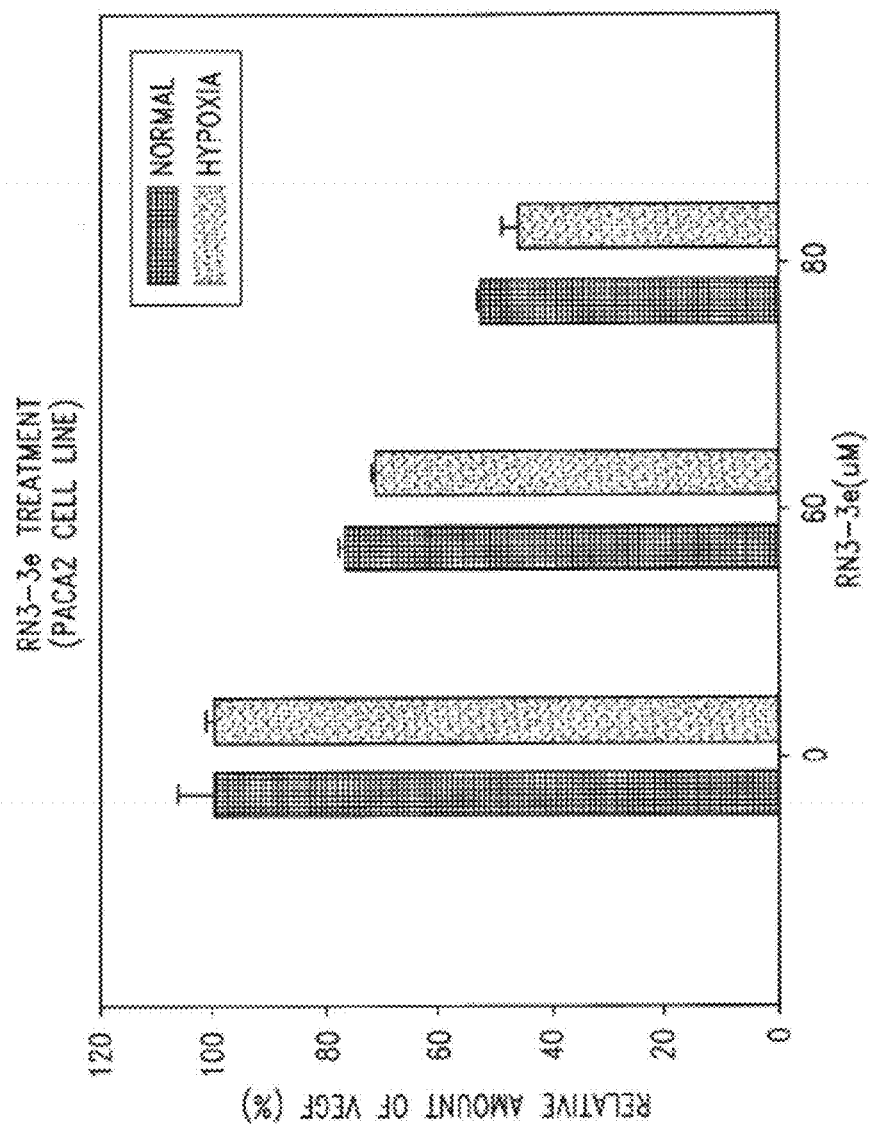
FIG. 6. VEGF ELISA Assay.
Figure 7:
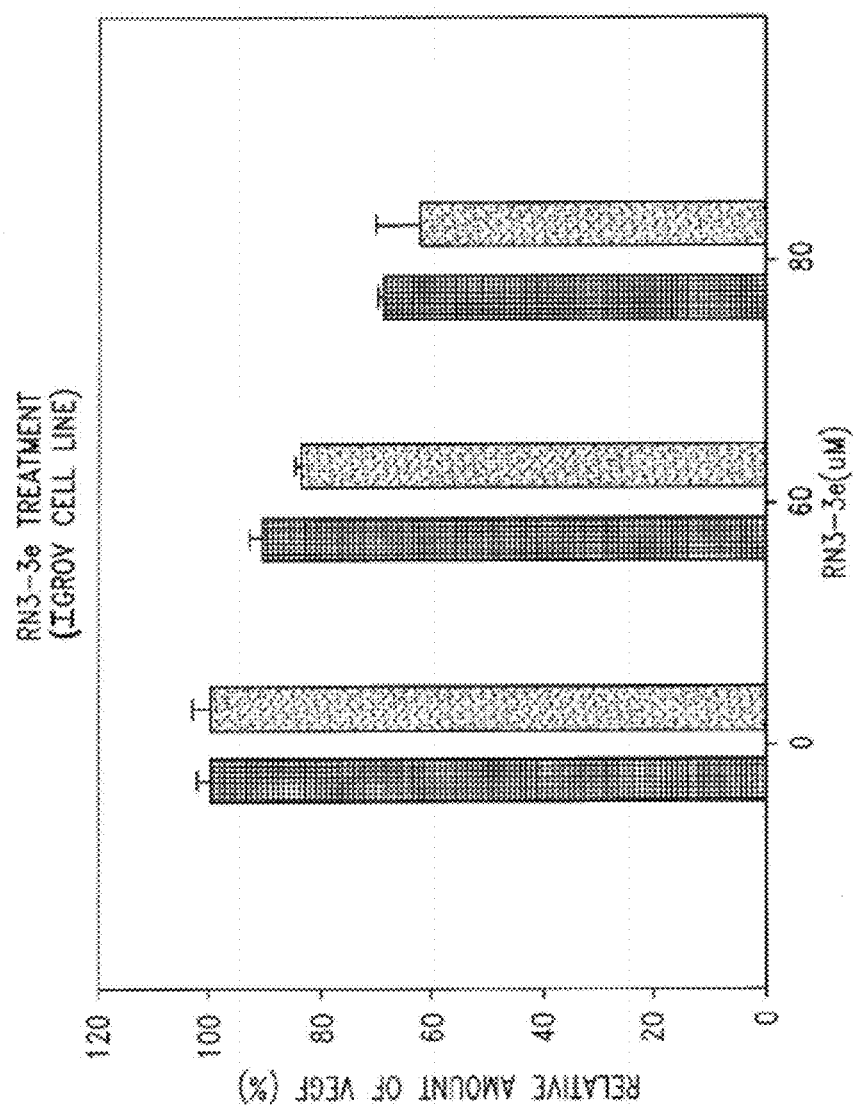
FIG. 7. VEGF ELISA Assay.

Inhibition of VEGF release. VEGF enzyme-linked immunosorbent assay (ELISA). Various cancer cell lines were plated in a 24-well plate and treated in duplicates with for about 24 hrs in normoxic (about 21% oxygen) or hypoxic (about 2% oxygen) condition. The supernatants of cells were collected and subjected to an ELISA assay with a kit specific for human VEGF according to the manufacturer (R&D Systems, Minneapolis, Minn.) VEGF ELISA assay results were read in a 96-well format plate reader by measuring absorbance at 450 nm with correction at 540 nm. Hypoxia induced an increase in VEGF release (FIG. 2). (For FIGS. 2-7, black bars=normoxia; gray bars=hypoxia.)

VEGF ELISA Assays. Hey-C2 (ovarian cancer), SKOV-3X (ovarian cancer), Pancl (pancreatic cancer), PaCa-2 (pancreatic cancer), and Igrov (ovarian cancer) cells were plated in a 24-well plate and treated in duplicates with (RN3-3 e) at different concentrations for about 24 hrs in normoxic (about 21% oxygen) or hypoxic (about 2% oxygen) condition. The supernatants of cells were collected and subjected to an ELISA assay with a kit specific for human VEGF according to the manufacturer (R&D Systems, Minneapolis, Minn.). VEGF ELISA assay results were read in a 96-well format plate reader by measuring absorbance at 450 nm with correction at 540 nm. APX3330 (RN3-3e) reduced the amount of VEGF release from the cells under both normoxia and hypoxia conditions through inhibition of Ape 1/Ref-1 redox function (FIGS. 2-7).

Inhibition of capillary tube formation. The capillary tube formation assay was performed using CB-ECFC cells plated on MATRIGEL® and treated with APX3330 or control media. ECFCs were cultured as previously described (Blood, 1 Nov. 2004, Vol. 104, No. 9, pp. 2752-2760). ECFC colonies appeared between 5 and 22 days of culture. Colonies were counted by visual inspection using an inverted microscope (Olympus, Lake Success, N.Y.) under ×40 magnification. Cells were passaged as previously described. Blood, 1 Nov. 2004, Vol. 104, No. 9, pp. 2752-2760.)

Figure 8:
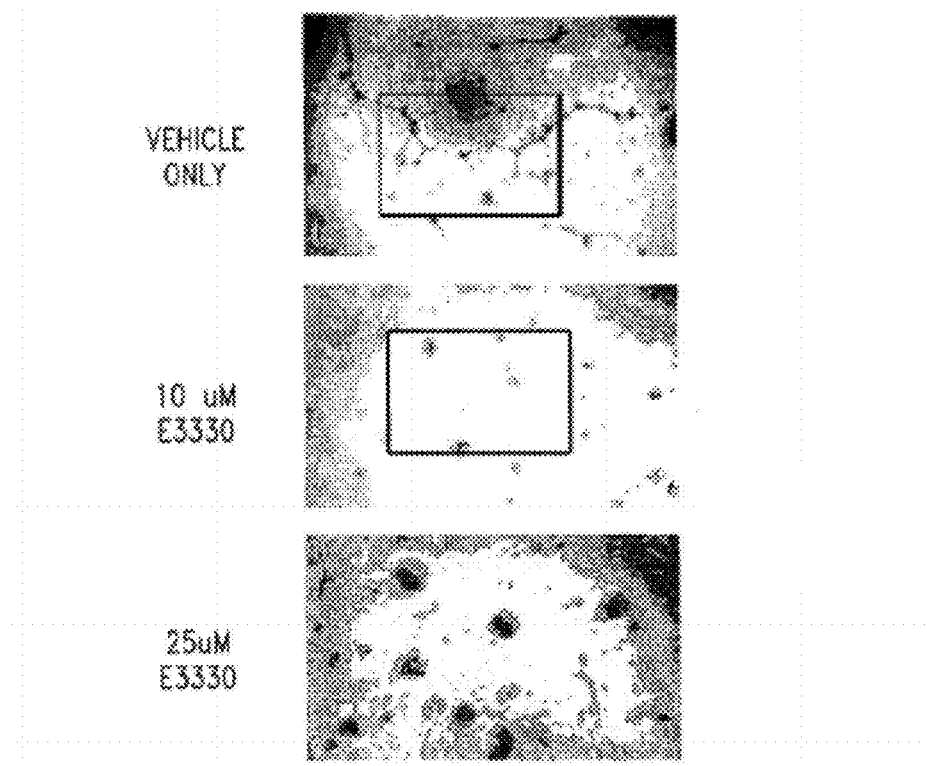
FIG. 8. Capillary tube formation assay using CB-ECFC cells plated on MATRIGEL®.

The tube formation assay was performed as described previously (J. Biol. Chem. 274 (1999), pp. 35562-135570). Various concentrations of APX3330 were given to CB-ECFCs for about 30 min at room temperature before seeding and plated onto the layer of MATRIGEL® at a density of about $1 \times 10^4$ cells/well. After about eight hours, the enclosed networks of complete tubes from randomly chosen fields were counted and photographed under a microscope. APX3330 and its analogues inhibit tube formation, an indicator of anti-angiogenesis and growth inhibition (FIG. 8).

Figure 9:
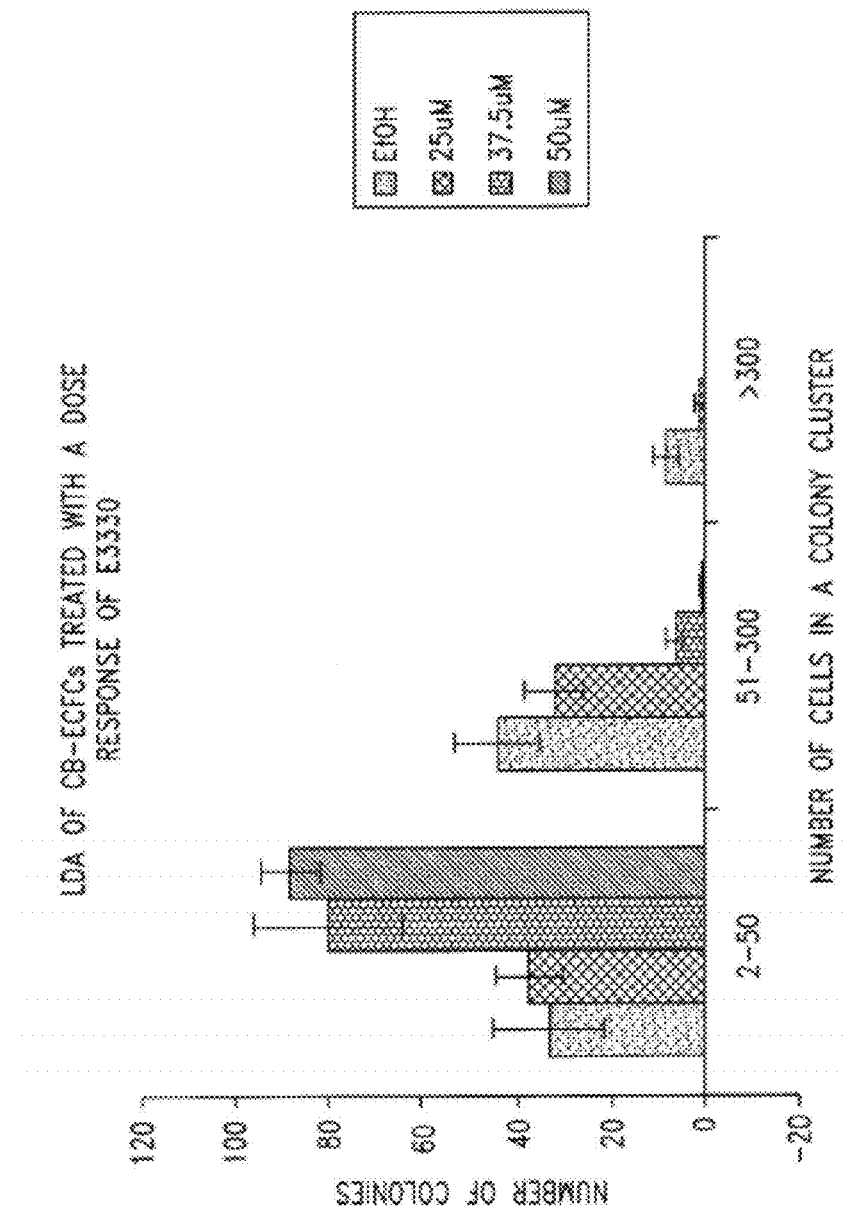
FIG. 9. Limiting dilution assay (LDA).

Limiting dilution assay. APX3330 inhibit growth of large cell number colonies in the limiting dilution assay (LDA) which is also an indicator of anti-angiogenesis (FIG. 9). ECFCs were cultured as previously described (Blood, 1 Nov. 2004, Vol. 104, No. 9, pp. 2752-2760). ECFC colonies appeared between 5 and 22 days of culture. Colonies and the number of cells per colony were counted by visual inspection using an inverted microscope. APX3330 inhibit growth of large cell number colonies in the limiting dilution assay (LDA) which is also an indicator of anti-angiogenesis. Increasing amounts of APX3330(RN3-3) leads to a decrease in the number of colonies with large numbers of cells and an increase in colonies with only small cell numbers indicative of inhibition of cell growth. (FIG. 9). (In FIG. 9, the bars are, left to right, EtOH, and E330 dosed at 25 μM, 37.5 μM, and 50 μM.)

Inhibition of endothelial cell proliferation. APX3330 at about 10-100 μM decreased retinal endothelial cell proliferation in cells treated with or without basic fibroblast growth factor (bFGF). Young adult mouse retinal tissues were dissected out and digested. Cells were plated in 24 well plates and grown to confluence, then seeded to 96 well plates for assay. Three days after seeding, the total number of cells was assayed by MTS measurement (Promega). The proliferation rate was calculated according to manufacturer's instructions. Proliferations of RECs from different groups were compared for statistical significance. APX3330 (RN3-3) blocked REC proliferation indicative of anti-blood vessel formation effects. (FIG. 10)

Figure 11:
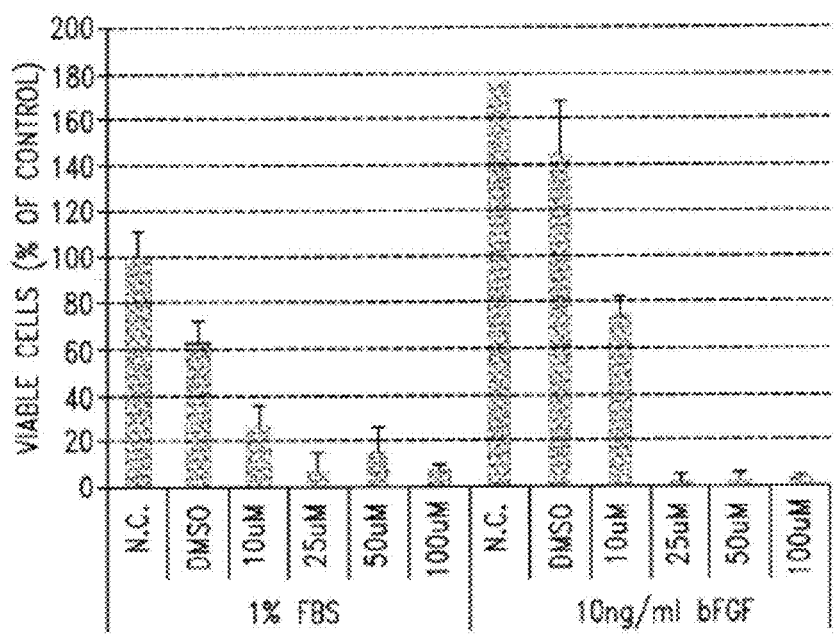
FIG. 11. Effect of APX3330 (RN3-3) on the proliferation of retinal vascular endothelial cells (RVEC)-wild/sv40 cells.

APX3330 10-100 μM decreased cell proliferation of retinal vascular endothelial cells (RVEC) (FIG. 11). In basal media, APX3330 inhibited REVC cell proliferation at all 4 concentrations tested, 10 μM-57%, 25 μM-93% (p<0.01). REC proliferation was significantly boosted when bFGF was added in the media. A similar inhibitory effect was also seen in bFGF media at 10 μM, 25 μM, and higher concentration of APX3330.

In vitro tube formation assay. Additionally, it was observed that in an assay observing in vitro tube formation, APX3330, like AVASTIN®, prevented formation of blood-vessel-like tubules in endothelial cells, in a dose dependent manner. In that assay it was also observed that a combination use of AVASTIN® and APX3330 was synergistically more effective than either alone.

SNV in vldlr−/− knockout mice assay. It has been observed APX3330 intravitreal treatment significantly reduces the number of subretinal neovascularization (SNV) in vldlr−/− retina. Experiments were carried out in very-low-density lipoprotein receptor (vldr) knockout mice to determine the effect of APX3330 on inhibition of SNV development in the vldlr−/− mutant. Each animal received a single intravitreal injection of 1 μl volume of BSS as a vehicle control and the fellow eye received 1 μl of 200 nm APX3330. The final concentration of APX3330 was equivalent to approximately 20 μM in the retina. Quantitative measurement of SNV was carried out one week after the treatment in the whole mount retina after lectin-FITC staining. The results showed that 17/20 individuals had reduced number of SNV in the eyes treated with APX3330 with ~30% reduction. In contrast, neither AVASTIN® (VEGF antibody) nor bFGF antibody treatment showed any sign of inhibition to the number of SNV. The apparent increase of SNV after antibody injection could be due to foreign protein triggered immune response which has been reported before (Tator et al., 2008). APX3330 reduced the number of SNV at a statistically significant level (p<0.01 in paired t-test). These data are very encouraging as this model of retinal angiomatous proliferation (RAP), similar to human, is difficult to treat and does not respond well to current avail-able treatments including anti-VEGF and anti-bFGF agents. The Ape1/Ref-1 inhibitor offers a new approach to control angiogenesis for advanced macular degeneration (AMD) treatment.

The present disclosure also encompasses the use of agents that inhibit the redox function of Ape1/Ref-1 as anti-cancer therapeutics. Such cancers include breast, prostate, pancreatic, colon, cervical, germ cell tumors, adult and pediatric gliomas, osteosarcomas, rhabdomyosarcomas, non-small cell lung cancer, leukemias, and multiple myeloma. Ape1/Ref-1 has been shown to stimulate the DNA binding activity of several transcription factors such as HIF-1α, Nfκrβ, AP-1 and p53, which are related to tumor survival and progression. Selective inhibition of the redox function of Ape1/Ref-1 by APX3330 decreases the binding of transcription factors to DNA and impairs the ability of cancer cells to thrive. The following examples are for illustrative purposes only and are not intended to limit the scope of the present disclosure.

Figure 12:
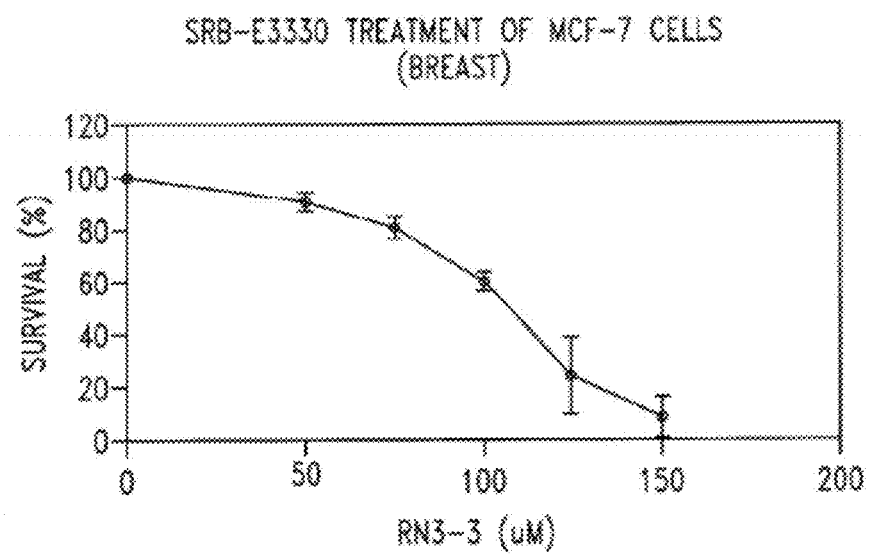
FIG. 12. MTS assay using MCF-7 tumor cells derived from human breast adenocarcinoma. 3-(4-5-Dimeth-ylthi-azol-2-yl)-5-(3-carboxymethoxyphenyl)-2-(4-sulfophenyl)-2H-tetrazolium salt (MTS) assay used for cell survival/growth analysis.
Figure 13:
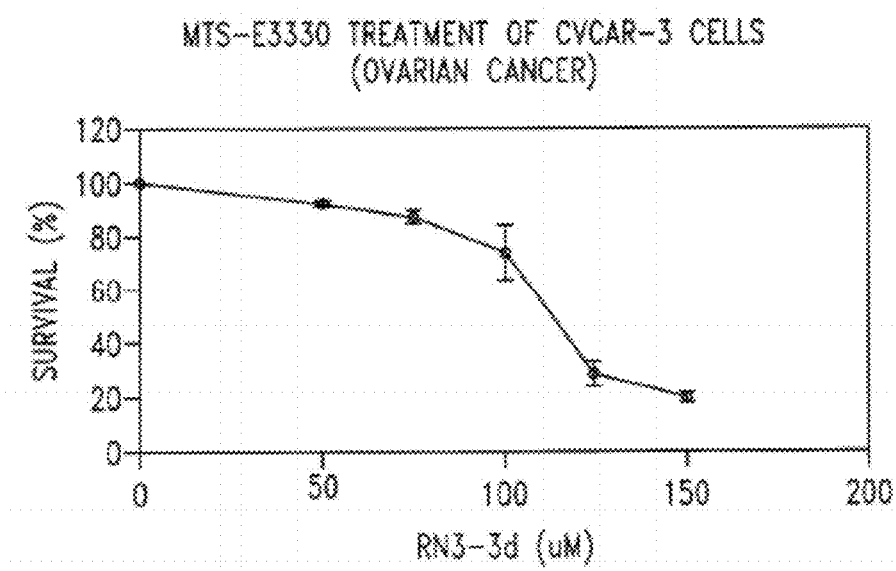
FIG. 13. MTS assay using OVCAR-3 tumor cells derived from human ovarian adenocarcinoma.
Figure 14A:
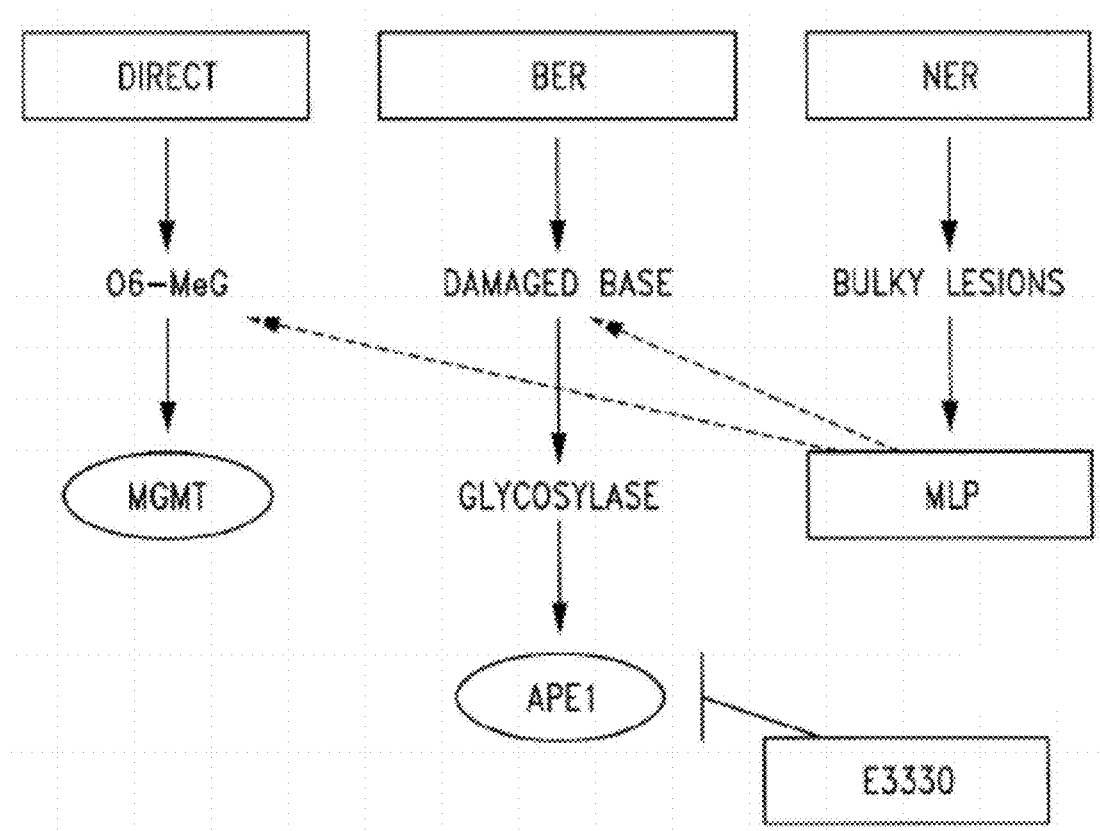
FIGS. 14A-14D. Effect of APX3330 (RN3-3) in combination with the chemotherapeutic drug melphalan on multiple myeloma cells.
Figure 14B:
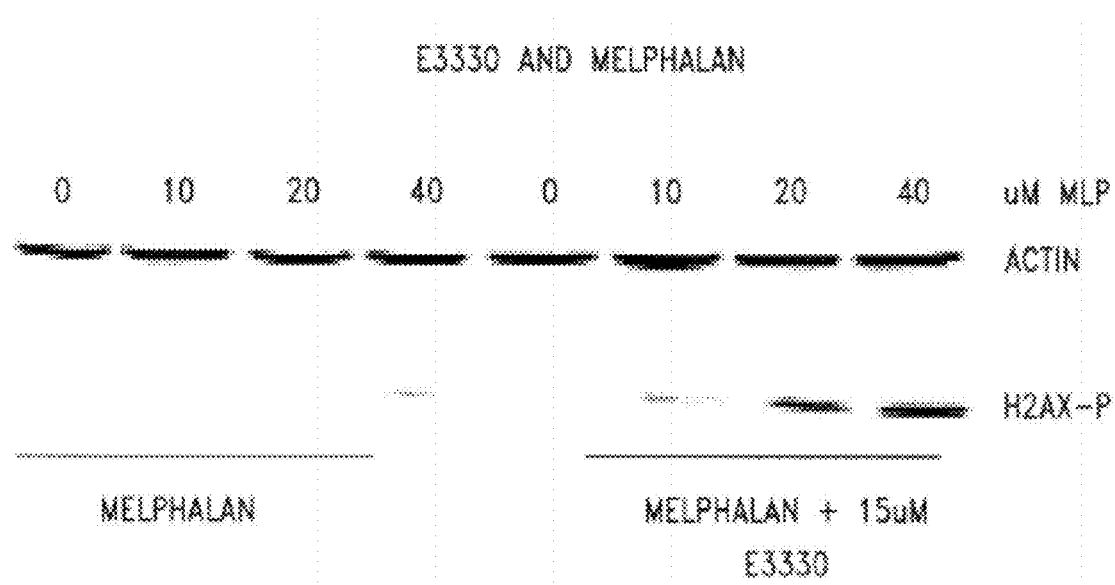
Figure 14C:
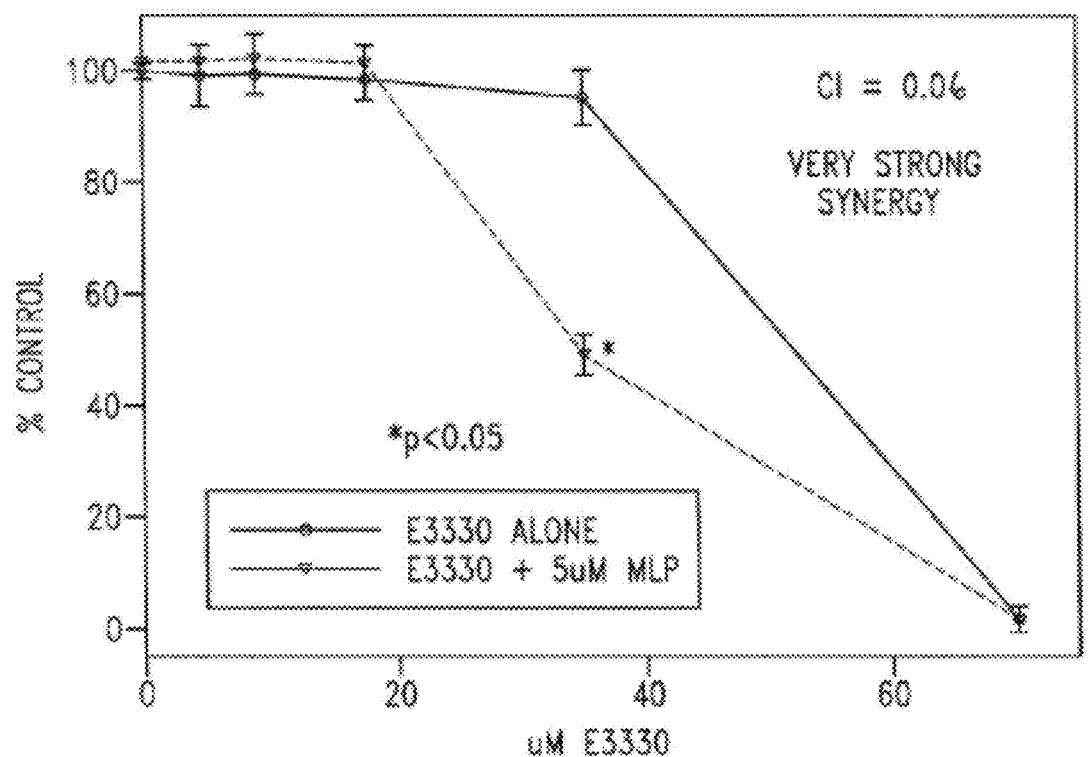
Figure 14D:
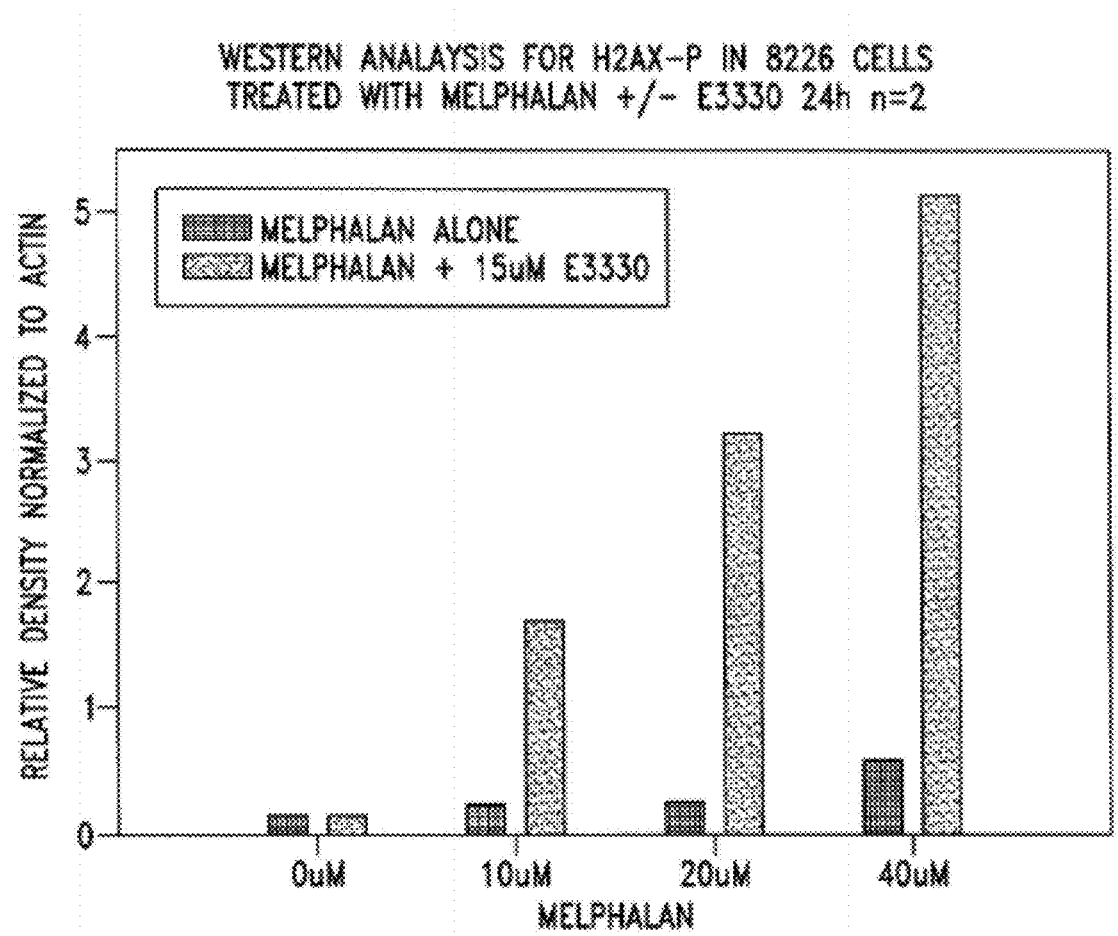

Decreased cancer cell survival. MCF-7 or OVCAR-3 cells (about 2-4,000) were aliquoted into each well of a 96-well plate in triplicate and allowed to adhere overnight. APX3330 (RN3-3) was added to the cultures. After about 24 or 72 h, about 0.05 mg/mL 3-(4-5-Dimethylthiazol-2-yl)-5-(3-carboxymethoxyphenyl)-2-(4-sulfophenyl)-2H-tetrazolium salt (MTS) reagent was added to each well and incubated at about 37° C. for about 4 h followed by absorbance measurement at 490 nm. The values were standardized to wells containing media alone. Independently, APX3330 dose dependently killed MCF-7 tumor cells derived from human breast adenocarcinoma (FIG. 12) and OVCAR-3 tumor cells derived from human ovarian adenocarcinoma (FIG. 13). Similar effects can be seen in multiple myeloma, prostate, non-small cell lung carcinoma, colon, and glioma derived cells. In contrast, significant growth inhibition in our studies with normal cells such as hematopoietic embryonic cells or in human CD34+ progenitor cells was not observed. These data are novel in that they implicate the redox role of Ape1/REF-1 in cancer, but not "normal" cell survival.

Glioma Cell Migration Assay. APX3330 was tested to determine if it would inhibit the migration ability of SF767 glioma cells. In order to do this, we plated $1.5 \times 10^6$ SF767 cells in a 60 mm tissue culture dish and allowed them to attach overnight and form a confluent monolayer. A scratch or wound was made across the plate using a 200 μL pipette tip as described previously (Liang 2007). The cells were then rinsed to remove floating cells and media contain 25, 50, 75 or 100 μM APX3330 or the appropriate vehicle control, DMSO. The drug-containing media was removed after 24 h and fresh media was added Images were taken at three marked places along the scratch at 0, 24, 36 and 48 h after the drug was added. Migration was quantified in ten uniform places for each image taken using Spot Software (Diagnostic Instruments, Sterling Heights, Mich.) to measure the distance in microns between the leading edges of the scratch. Each set of data, a total of thirty for each data point, was normalized to the migration of the vehicle control at 0 h and used to determine standard deviation. The results indicate the APX3330 inhibited the ability of the SF767 cells to migrate, and exhibited as much as 4.0-fold inhibition with 100 µM APX3330-treated cells as compared to the vehicle control at 48 h.

Our results support an effect on the microenvironment, or stroma. The microenvironment, which is distinct from the cancer cells per se, plays a part in a tumor's progression, including metastasis. It can limit the access of therapeutics to the tumor, alter drug metabolism, and contribute to drug resistance. Clearly, being able to affect the microenvironment can assist in the ultimate therapeutic results achieved in regard to tumors.

In another embodiment, the present disclosure is directed to the use of agents that inhibit the redox function of Ape1/Ref-1 in combination with other therapeutics. Such therapeutics include, but are not limited to, melphalan, gem-citabine, cisplatin, methoxyamine, thalidomide and its derivatives, and retinoic acid (RA). Selective Ape1/Ref-1 inhibition can act synergistically with other therapeutics to increase anticancer efficacy. Thus, lower doses of therapeutics, which cause sickness and are toxic to normal cells at higher doses, can be administered without a decrease in anti-cancer efficacy. Use of agents that selectively inhibit the redox function of Ape1/Ref-1 can provide protection for normal cells against the effects of cisplatin and other chemotoxic compounds. The following examples are for illustrative purposes only and are not intended to limit the scope of the present disclosure.

APX3330 in combination with chemotherapeutic Melphalan. APX3330 in combination with the chemotherapeutic drug melphalan synergistically enhanced killing of multiple myeloma cells (FIGS. 14A-14D). Synergistic plots made using CalcuSyn software. APX3330 was either given alone or in combination with melphalan. As an indicator of DNA double stranded breaks (DSBs), the phosphorylation of histone H2AX at Ser$^{139}$ was measured with a phosphorylation-specific H2AX antibody from Upstate Cell Signaling Solutions (Waltham, Md.). Cells were treated with melphalan alone or melphalan plus APX3330. After drug treatment, exponentially growing cells were harvested, washed in cold PBS, and lysed in about 100 µL RIPA assay buffer as described above. Protein was quantified and electrophoresed in SDS gel-loading buffer on a 12% SDS-polyacrylamide gel. Mouse monoclonal anti-phosphohistone H2AX (about 1:1000) or anti-actin antibody (about 1:1000; as a loading control, LabVision Corp., NeoMarkers, Fremont, Calif.) was used to probe for protein levels as described previously. Bands were detected using a chemiluminescence kit from Roche Applied Biosciences (Indianapolis, Ind.). The bands were visualized using Bio-Rad Chemidoc XRS (Hercules, Calif.) and quantitated using Chemidoc software, Quantity One 4.6.1. There is an increase in DSBs in the melphalan plus APX3330 (RN3-3) compared to melphalan alone.

Figure 15:
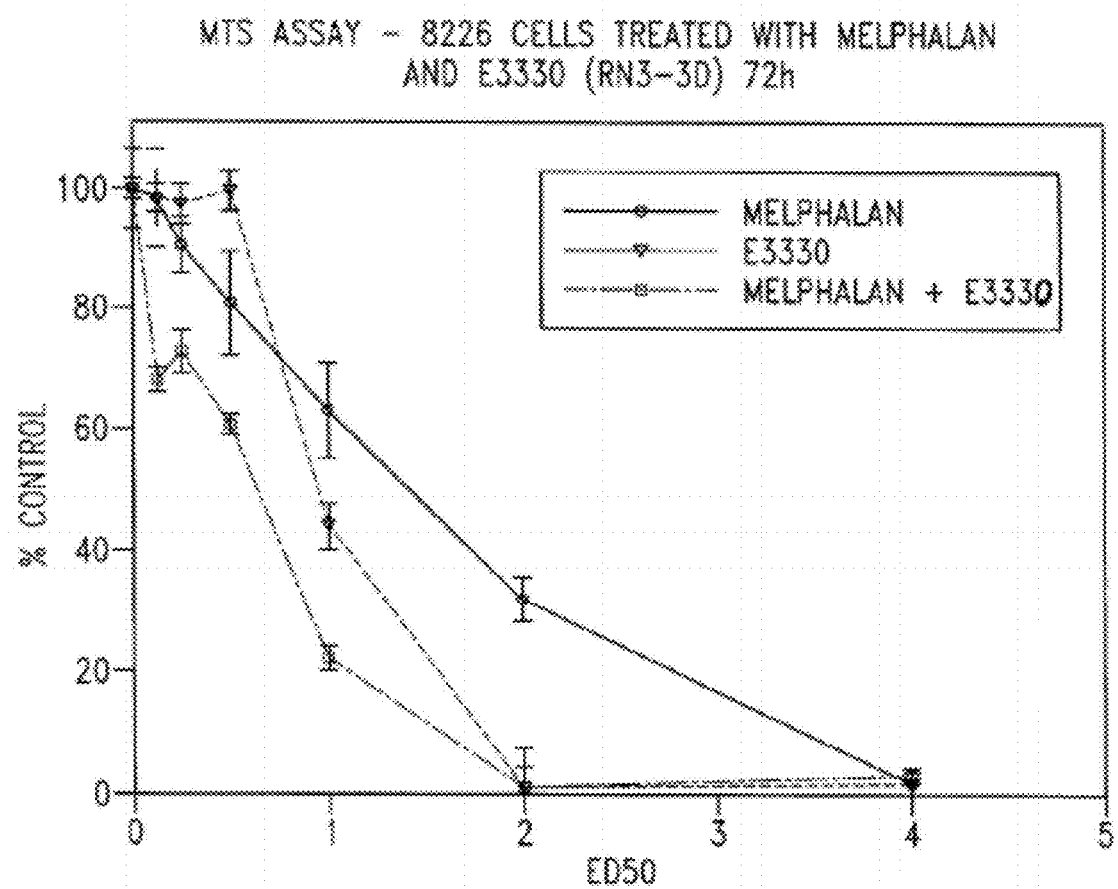
FIG. 15. Effect of APX3330 (RN3-3) in combination with chemotherapeutic drug melphalan on multiple myeloma cells in the MTS assay after 72 hours.

APX3330 (RN3-3) was applied in combination with the chemotherapeutic drug melphalan and was found to synergistically enhance the killing of multiple myeloma cells in the MTS assay after 72 hours (FIG. 15). APX3330 (RN3-3) was either given alone or in combination with melphalan and the ED50 plotted against the percent control as per the CalcuSyn software which is based on the Chou-Talalay algorithm (Chou-Talalay; Advances in Enzyme Regulation 22, 27-55). Melphalan plus APX3330 (RN3-3) is more effective than either agent alone.

Figure 16:
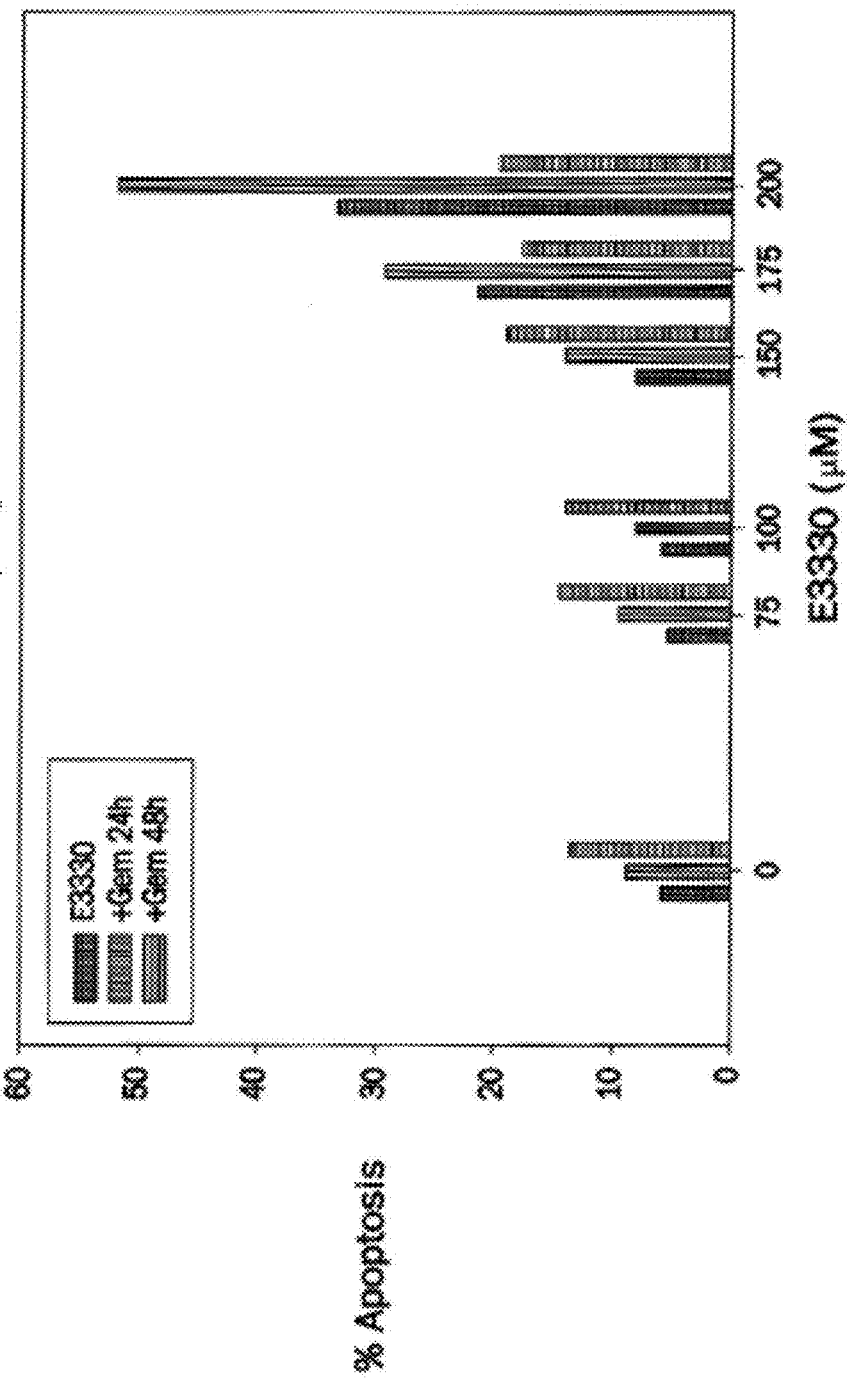
FIG. 16. Effect of APX3330 (RN3-3) and gemcitabine (0.25 µM) on pancreatic tumor cells at 24 and 48 hours.

APX3330 in combination with chemotherapeutic Gemcitabine. APX3330 enhanced the apoptosis inducing effects of gemcitabine (about 0.25 µM) in pancreatic tumor cells (FIG. 16). To analyze the cells for apoptosis, cells were plated and allowed to attach overnight. Cells were treated with APX3330 alone or with gemcitabine. Apoptosis was assayed about 24 and 48 hr following treatment. Cells were trypsinized, pelleted, washed in ice-cold PBS, and resuspended in 1× binding buffer [about 10 mmol/L HEPES/NaOH (pH 7.4), 140 mmol/L NaCl, 2.5 mmol/L CaCl$_2$]. Apoptosis was analyzed using the Alexa Fluor 488 AnnexinV from Vybrant Apoptosis Assay kit in combination with propidium iodide (Molecular Probes, Eugene, Oreg.) as described previously Clinical Cancer Research 13, 260-267, Jan. 1, 2007. Cells that were strongly Annexin positive were considered positive for apoptosis. The samples were analyzed by flow cytometry in the Indiana University Cancer Center flow cytometry facility.

Figure 17:
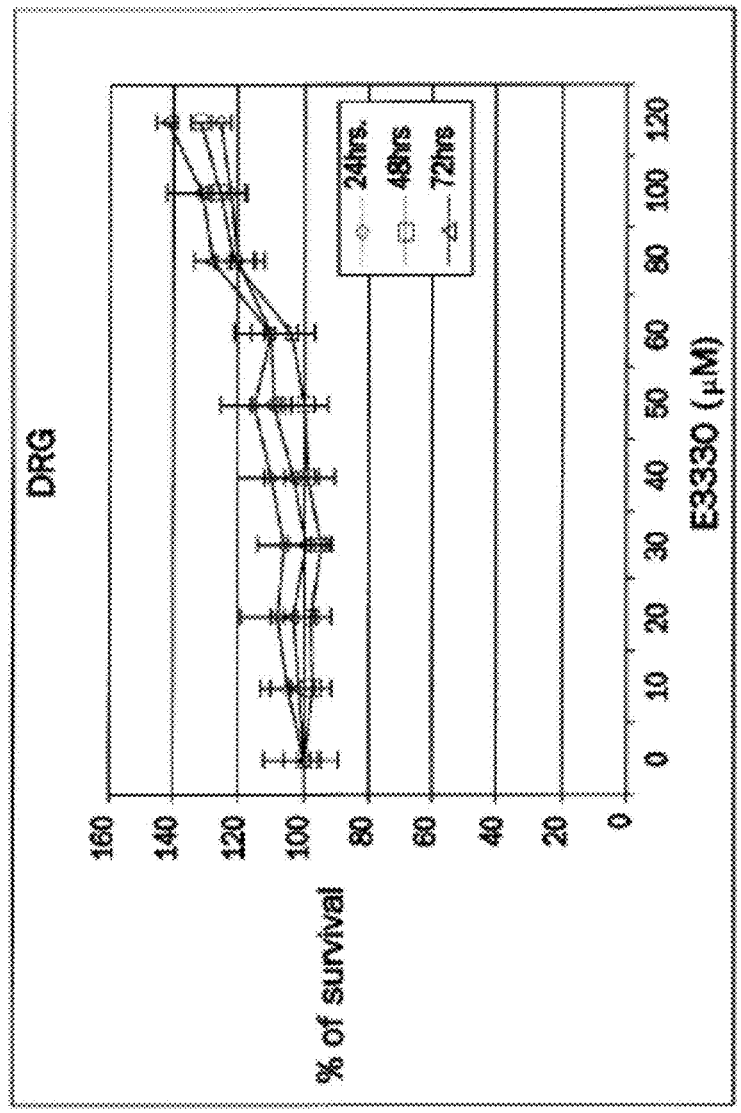
FIG. 17. MTS cell viability assay.

APX3330 in combination with chemotherapeutic Cisplatin. Concentrations of APX3330 as high as about 120 µM did not impair the survival of rat dorsal root ganglion cells growing in culture for up to about 72 hours, as measured by the MTS cell viability assay (FIG. 17). There was no effect of APX3330 (RN3-3) on the post-mitotic DRG cells, indicative of a non-toxic effect of APX3330 (RN3-3) on non-dividing cells.

Figure 18:
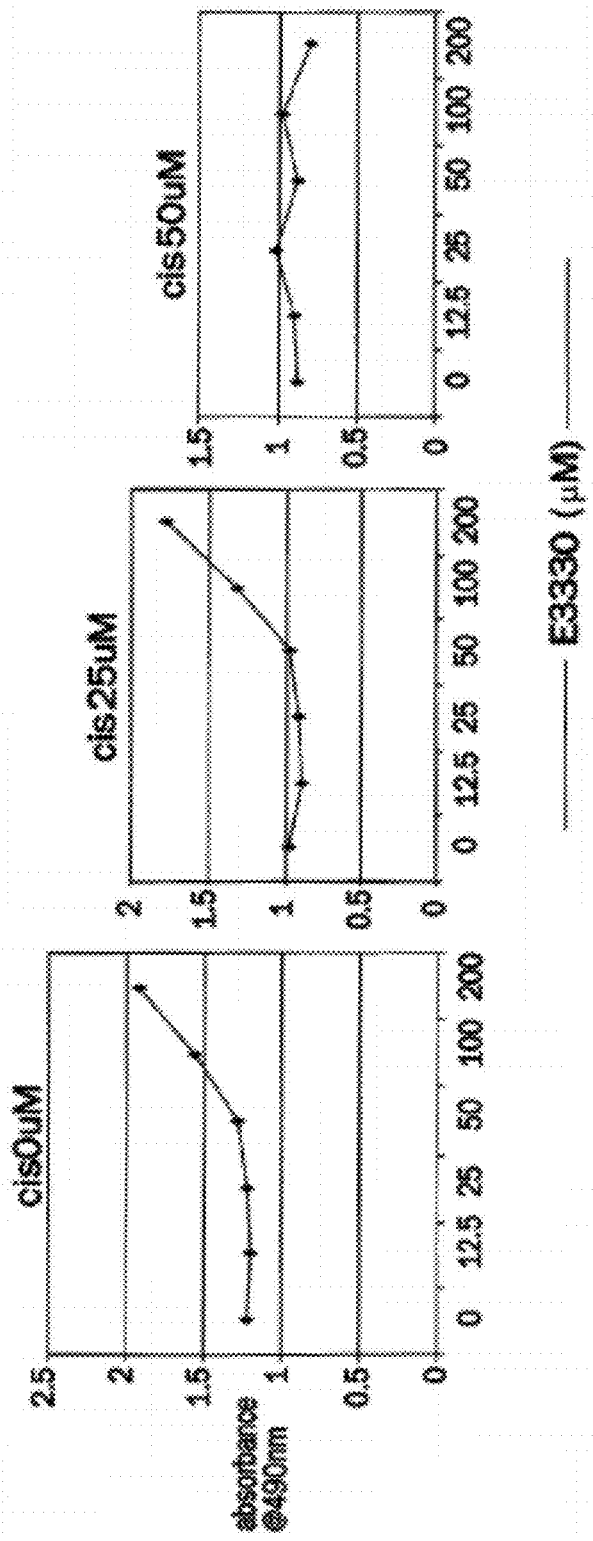
FIG. 18. MTS cell viability assay.

DRG cell cultures and treatments were performed similar to previously published procedures using just APX3330 alone (DNA Repair Volume 4, Issue 3, 2 Mar. 2005, pp 367-1379). Further, APX3330 provided protection against the neuro-toxic effects of the chemotherapeutic cisplatin when administered to rat dorsal root ganglion cells (FIG. 18). This demonstrates that while APX3330 (RN3-3) enhances some chemotherapeutic agents, it has a protective effect on non-dividing, post-mitotic cells (e.g. DRG cells) even in the presence of a chemotherapeutic agent.

Figure 23:
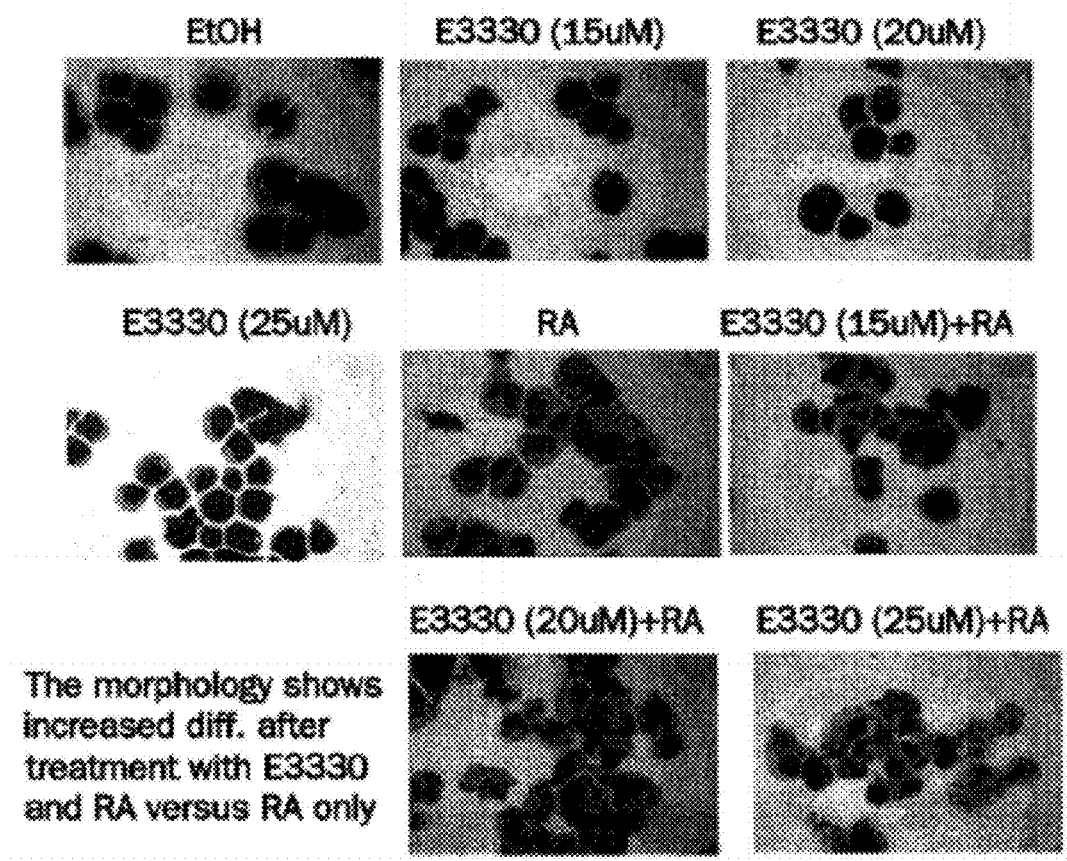
FIG. 23. Effect of APX3330 (RN3-3) and retinoic acid on promoting cell differentiation.
Figure 24:
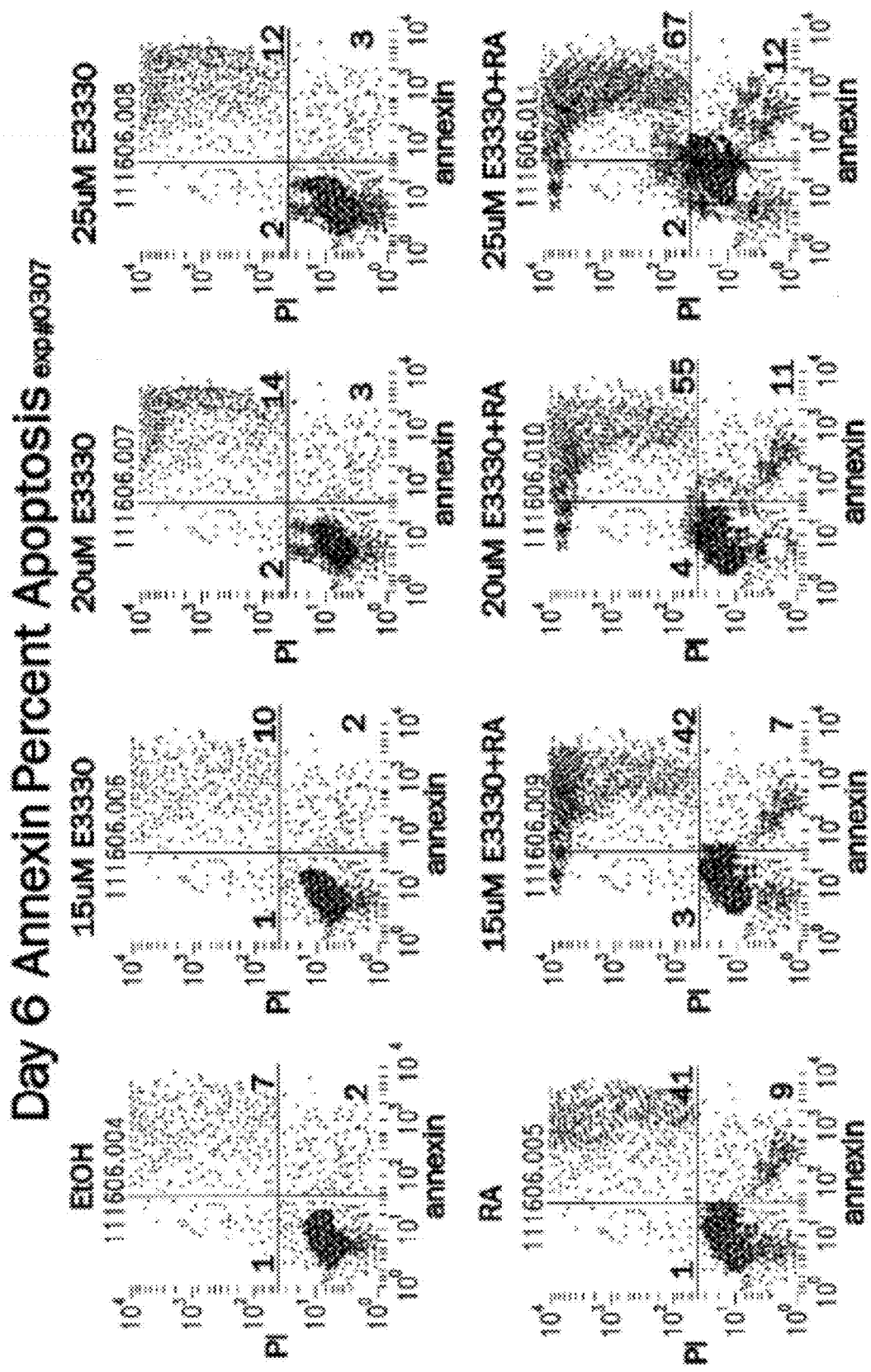
FIG. 24. Apoptosis analysis of HL-60 cells treated as described in FIG. 23 using annexin/PI assay.
Figure 27A:
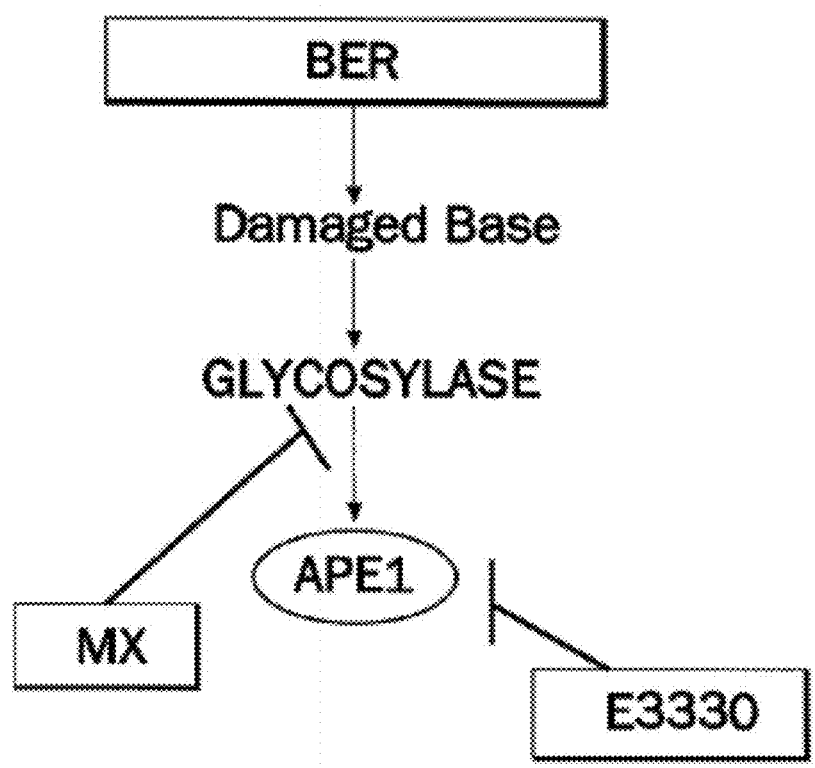
FIGS. 27A-27D. Effect of APX3330 (RN3-3) in combination with the small molecule methoxyamine on multiple myeloma cells.
Figure 27B:
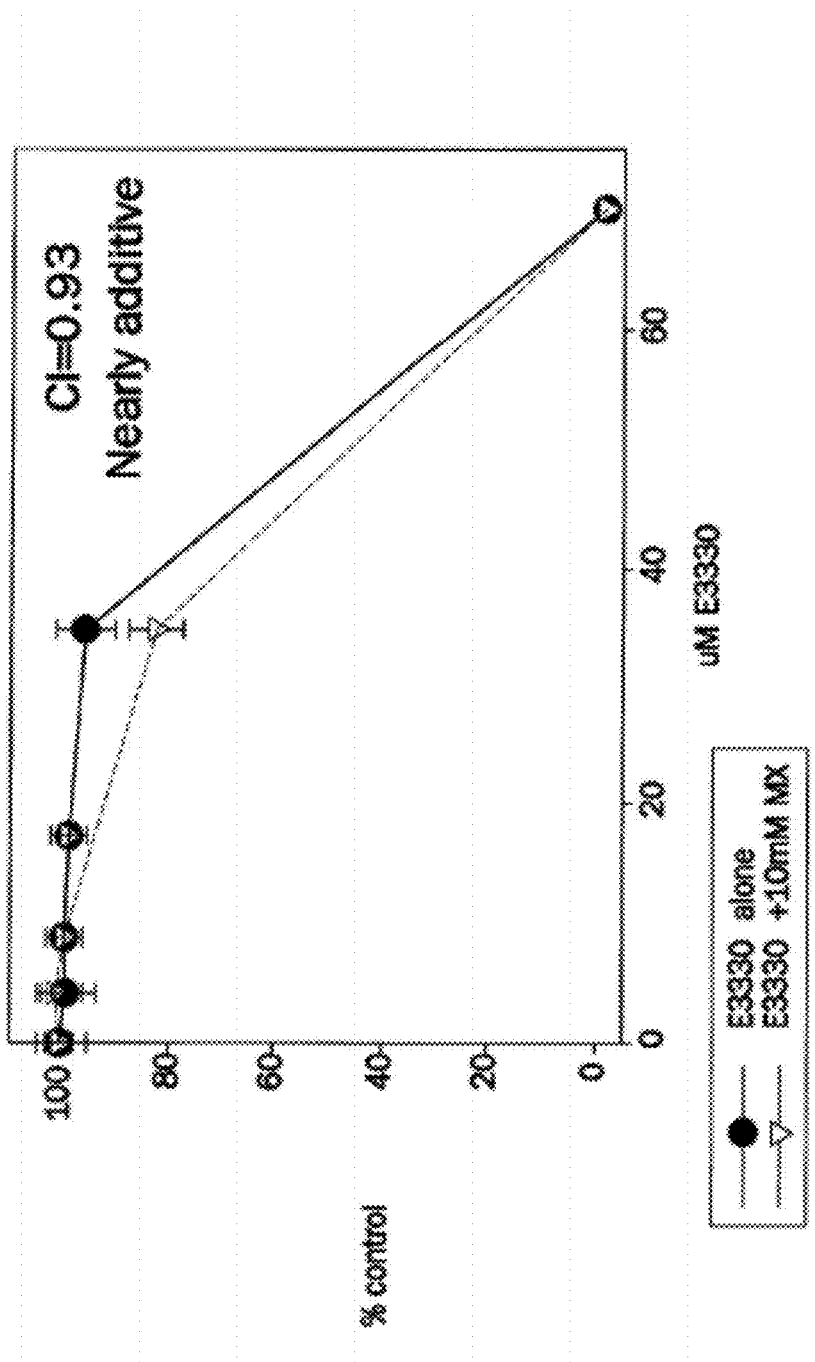
Figure 27C:
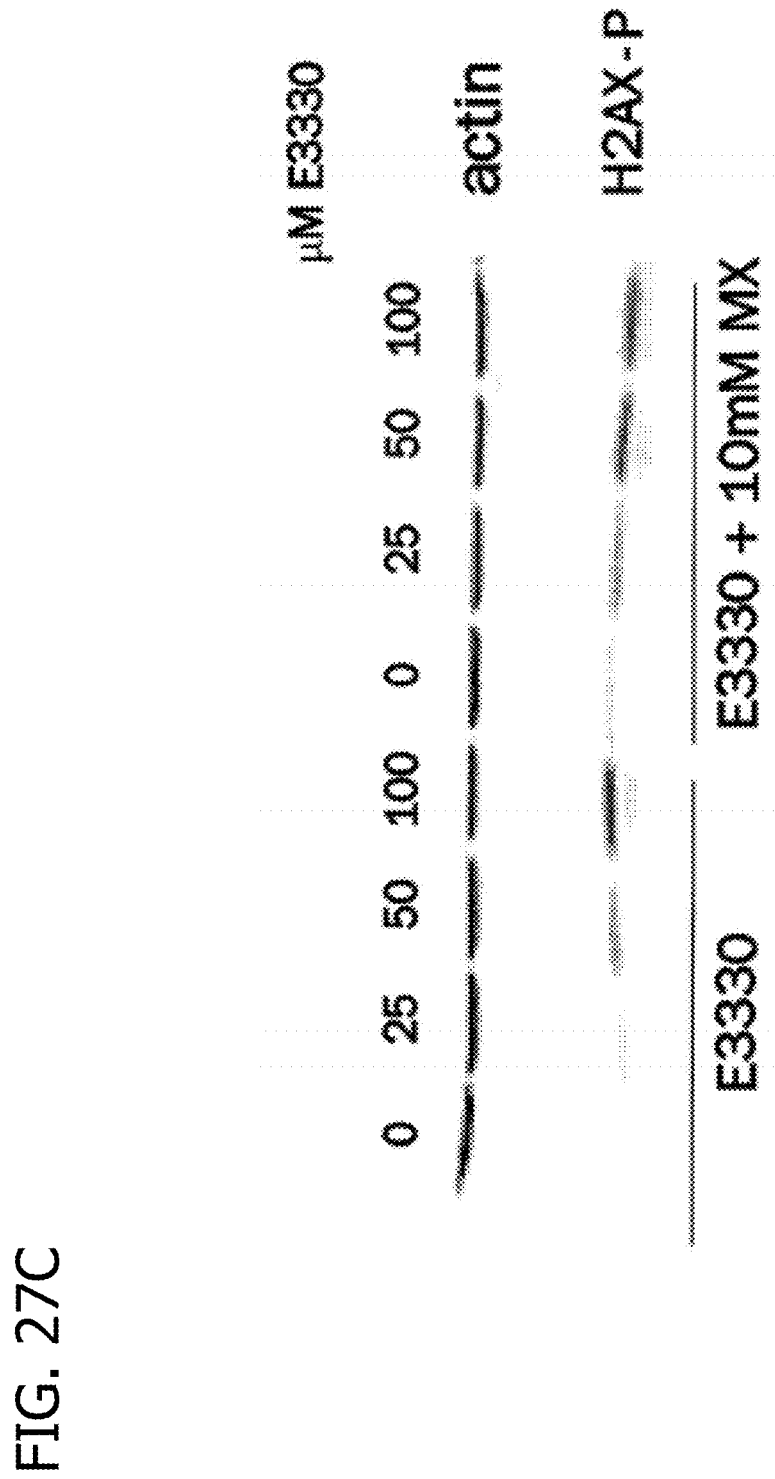
Figure 27D:
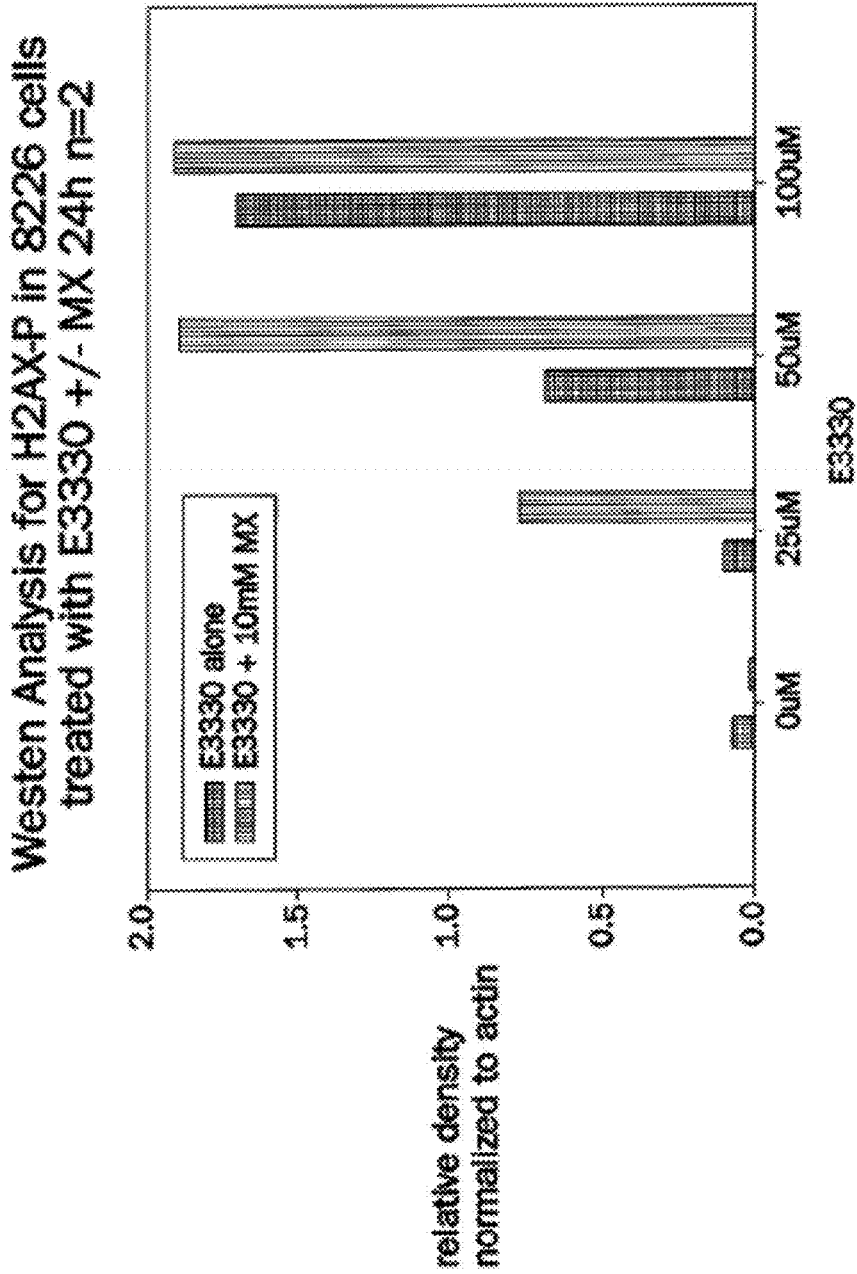

APX3330 in combination with Retinoic Acid. APX3330 enhanced the effects of retinoic acid on promoting cell differentiation (FIG. 23). HL-60 cells were treated with either vehicle (EtOH; control), APX3330, retinoic acid (RA) or APX3330 and RA at the concentrations indicated and morphology determined on day six. Morphological analysis indicated an increase in the differentiation of the HL-60 cells treated with APX3330 (RN3-3). Apoptosis analysis of HL-60 cells at day 6 revealed that the combination of APX3330 and RA showed an increase in the number of cells undergoing apoptosis com-pared to the cells treated with APX3330 alone, and about a 1.5 increase compared with RA alone at the 25 µM dose APX3330 (FIG. 24).

APX3330 enhanced the effect of RA at the 1000 fold lower dose of RA, but resulted in similar levels of differentiation as with the higher doses of RA. CD11, which is a marker for HL-60 differentiation, demonstrated that the addition of APX3330 to RA allows for about 1000 fold (3 orders of magnitude) less RA being required to have the same level of differentiation as at higher doses of RA (FIG. 25).

APX3330 did not significantly enhance the level of HL-60 cells undergoing apoptosis (annexin/PI assay) at lower doses of RA even though the level of differentiation was greatly enhanced by about 1000 fold (FIG. 26).

These results indicate that APX3330 plus RA leads to cell differentiation but not increased apoptosis in these cells and model system at the reduced doses of RA.

APX3330 in combination with Methoxyamine-multiple myeloma cells. APX3330 in combination with the small molecule methoxyamine enhanced killing of multiple myeloma cells as assayed by MTS (FIGS. 27A-27D). Data was calculated using the CalcuSyn software which is based on the Chou-Talalay algorithm (Chou-Talalay; *Advances in Enzyme Regulation* 22, 27-55). APX3330 was either given alone or in combination with methoxyamine.

As an indicator of DNA double stranded breaks (DSBs), the phosphorylation of histone H2AX at Ser1 39 was measured with a phosphorylation-specific H2AX antibody from Upstate Cell Signaling Solutions (Waltham, Md.). Cells were treated with APX3330 alone or APX3330 plus methoxyamine After drug treatment, exponentially growing cells were harvested, washed in cold PBS, and lysed in about 100 [IL RIM assay buffer as described above. Protein was quantified and electrophoresed in SDS gel-loading buffer on a 12% SDS-polyacrylamide gel. Mouse monoclonal anti-phosphohistone H2AX (about 1:1000) or anti-actin antibody (about 1:1000; as a loading control, LabVision Corp., Neo-Markers, Fremont, Calif.) was used to probe for protein levels as described previously. Bands were detected using a chemiluminescence kit from Roche Applied Biosciences (Indianapolis, Ind.). The bands were visualized using Bio-Rad Chemidoc XRS (Hercules, Calif.) and quantitated using Chemidoc software, Quantity One 4.6.1.

APX3330 in combination with Methoxyamine-pancreatic cells. APX3330 enhanced the apoptosis inducing effects of methoxyamine in pancreatic tumor. To analyze the cells for apoptosis, cells were plated and allowed to attach overnight. Cells were treated with APX3330 alone or with methoxyamine Apoptosis was assayed about 24 and 96 hr following treatment. Cells were trypsinized, pelleted, washed in ice-cold PBS, and resuspended in 1× binding buffer [about 10 mmol/L HEPES/NaOH (pH 7.4), 140 mmol/L NaCl, 2.5 mmol/L $CaCl_2$]. Apoptosis was analyzed using the Alexa Fluor 488 Annexin V from Vybrant Apoptosis Assay kit in combination with propidium iodide (Molecular Probes, Eugene, Oreg.) as described previously Clinical Cancer Research 13, 260-267, Jan. 1, 2007. Cells that were strongly Annexin positive were considered positive for apoptosis. The samples were analyzed by flow cytometry in the Indiana University Cancer Center flow cytometry facility.

Preliminary in vivo experiments. Preliminary in vivo experiments in mice were performed to explore the safety profile and determine the pharmacokinetic properties of APX3330 (FIGS. 19-22).

Figure 19:
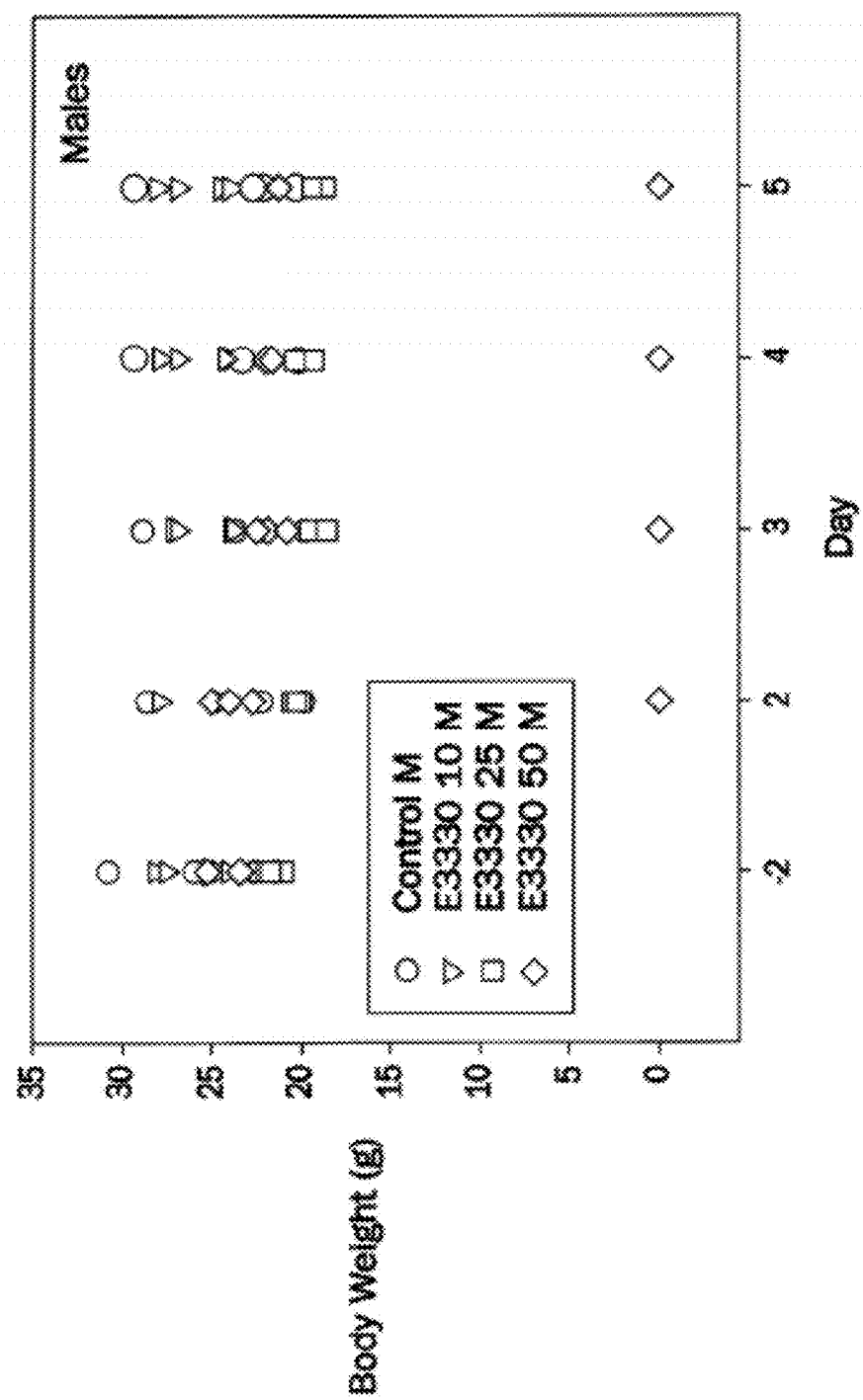
FIG. 19. Body weight in male mice administered APX3330 (RN3-3) (0-50 mg/kg).

FIG. 19. Body weight in male mice administered APX3330 (RN3-3) (0-50 mg/kg). No mouse toxicity was observed with APX3330 (RN3-3) under 50 mg/kg. Mice were treated with RN3-3 (APX3330) and weighed either two days before treatment or following treatment with the three doses of compound.

FIG. 20. Survival data of mice treated with RN3-3 (APX3330) at various amounts and observed on days 2, 3, 4 or 5 after treatment. The number of surviving mice over the total number are presented as surviving/total.

Figure 21B:
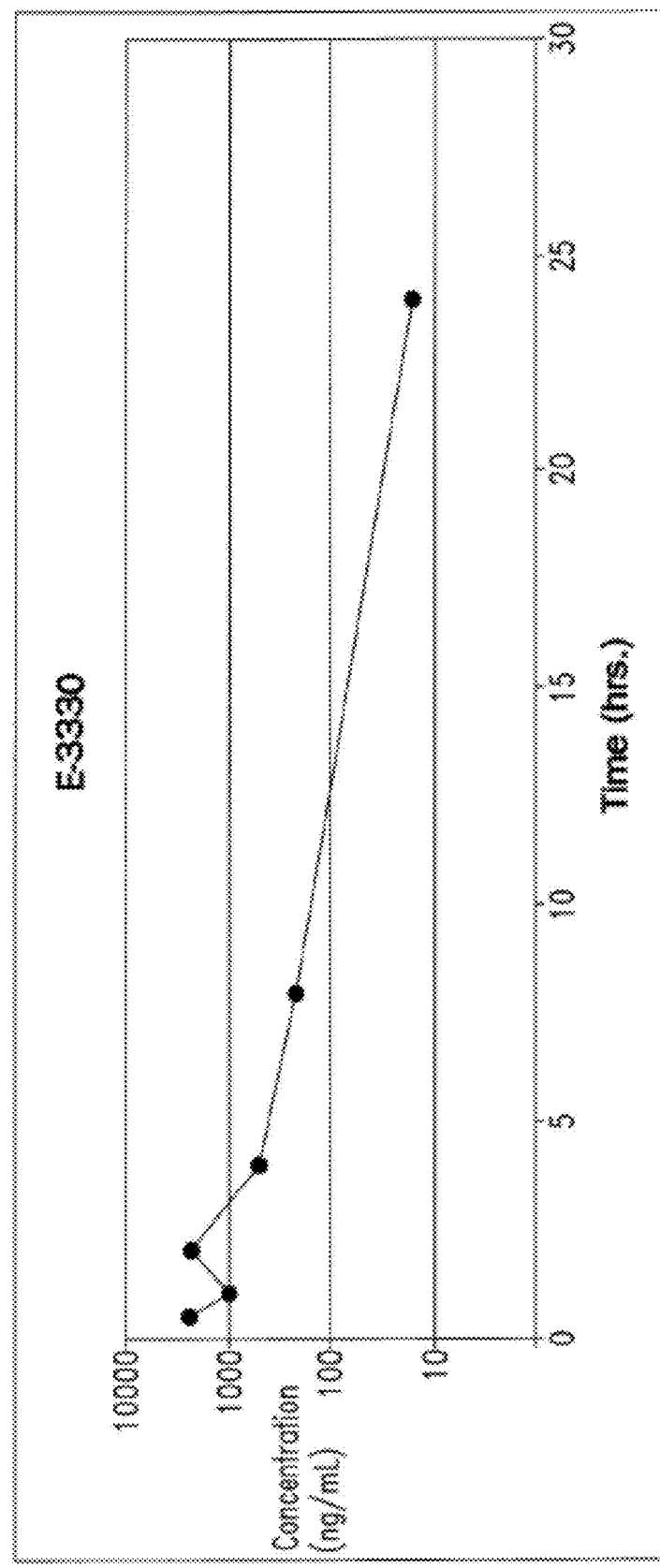

FIGS. 21A & 21B. Pharmacokinetic data of APX3330 (RN3-3) over a 24 hr time course experiment. Mice were treated with APX3330 (RN3-3) and then the blood concentration detected in the Clinical Pharmacology and Analytical Core (CPAC). The time vs. concentration of APX3330 (RN3-3) is plotted (FIG. 21B) and the estimated concentration is shown in the table (FIG. 21A). Three mice were used at each time point and the data represents the mean with SD (not shown) plotted for each time.

FIG. 22. Pharmacokinetic data for APX3330 (RN3-3). Data from the survival, weight and PK studies were collected and are shown in this table. The half-life of RN3-3 (APX3330) was determined for male, female and combined mice as well as their weight and concentrations.

Patients having urinary bladder cancer exhibit increased levels of APE1/Ref-1 in their serum and their urine, and APE1/Ref-1 levels correlated with tumor stage and grade suggesting APE1/Ref-1 may act as a biomarker in bladder cancer (BCa). However, a characterization of APE1/Ref-1 expression and activity in bladder cancer tissue has not been reported. To address this deficiency, APE1/Ref-1 expression was analyzed in control benign bladder tissue and bladder cancer tissue. Further, a tissue array was constructed from over 36 patients with cisplatin-refractory bladder cancer from cystectomy specimens.

APE1/Ref-1 expression was robust in the majority of patient tumor samples compared to benign. Assessment of potency and efficacy of APE1/Ref-1 redox-selective inhibitors in preclinical experimental BaC models is lacking, leaving APE1/Ref-1 inhibition as an untapped opportunity in bladder cancer therapy. Here, we report that inhibition of APE1/Ref-1 redox-specific signaling attenuates bladder cancer cell proliferation in monolayer, in 3D cultures and in vivo, induces apoptosis and blocks cancer cell proliferation, decreases the transcriptional activity of NFκB and STAT3, and thereby decreases expression of key survival proteins in vitro and in vivo. One of these proteins was survivin. Survivin is known to be induced during bladder cancer, and over the past year has become the focus of intense screening as a functional biomarker for the disease. Finally, we show that in vitro treatment with APE1/Ref-1 redox inhibitors in combination with the current standard-of care, cisplatin, is more effective than cisplatin alone.

Materials and Methods

Human Specimens

Figure 28A:
FIGS. 28A-28G. APE1/Ref-1 is expressed in bladder cancer tissue as well as bladder cancer cell lines including patient-derived xenograft lines, RP-B-01 and RP-B-02. APE1/Ref-1 (red) is expressed at a low level in benign bladder urothelium (FIG. 28A), but is highly expressed in urothelial carcinoma (FIGS. 28B & 28C) as determined by IF. Expression is primarily nuclear in non-invasive tumors (FIG. 28B), but exhibits both nuclear and cytosolic pattern in invasive lesions (FIG. 28C) Immunohistochemistry on cisplatin-refractory patient samples also demonstrated nuclear localization of APE1/Ref-1 in urothelial-confined tumor (FIG. 28D) and a shift to both cytosolic and nuclear expression in invasive tumor (FIG. 28E). Samples within The Cancer Genome Atlas (TCGA) confirmed that APE1/Ref-1 mRNA (APEX1) is significantly upregulated in bladder cancer patients compared to matched control p=1.68e-05, Mann Whitney test (FIG. 28F). Bladder cancer cell lines SW-780, UC3, T24, RT-4, *Scaber*, as well as the PDX lines B01 and B02 all expressed robust levels of APE1/Ref-1 in comparison to HUC (human urothelial cells), justifying their use for inhibitor study.

Two sets of paraffin-embedded human specimens were used for assessment of APE1/Ref-1 and target protein assessment by histology. In Set one (FIGS. 28B & 28C and FIGS. 29A-29C) used for APE1/Ref-1 immunofluorescence, specimens were obtained from patients undergoing cystectomy for muscle invasive bladder cancer, and controls were obtained as freshly harvested cadaveric specimens (FIG. 28A, n=12). These controls (average age 68±8 yrs) were age-matched to the bladder cancer specimens (64±8 yrs) and were confirmed by histology to be free from malignant or inflammatory bladder disease. The controls used in this analysis were verified by pathology to be void of bladder cancer or bladder inflammatory diseases. Specimens were fixed in 10% buffered formalin, processed routinely through ethanol and xylene gradients and into paraffin, and embedded in paraffin blocks. Sections were made at 5 μm via microtome cutting. All human specimens were stained with APE1/Ref-1 antibodies and known target proteins of APE1/Ref-1 signaling for immunofluorescence or immunohistochemistry, as described below. In addition, basic histology of these specimens was performed by hematoxylin and eosin (H&E) staining; this was used to assess any underlying inflammation and the pathological features of bladder tumors or any underlying pathology that may have been present in the controls, which disqualified them from use.

Figure 28B:
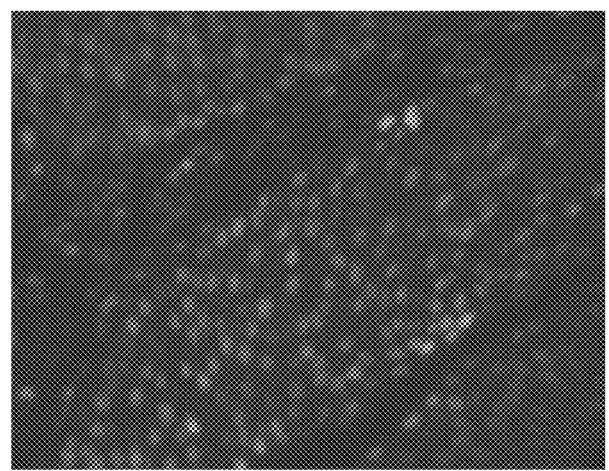
Figure 28C:
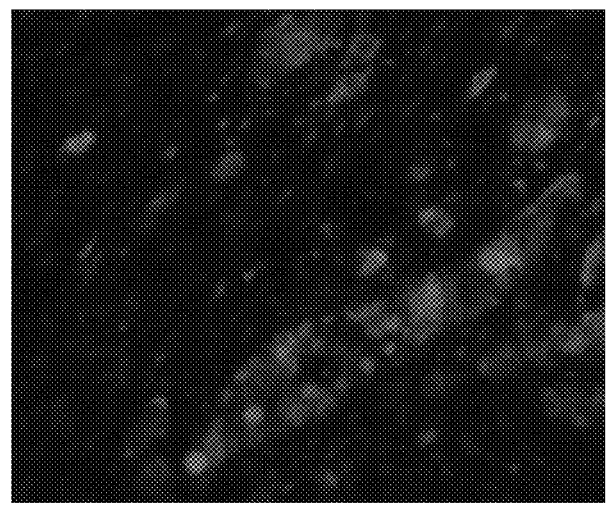
Figure 28D:
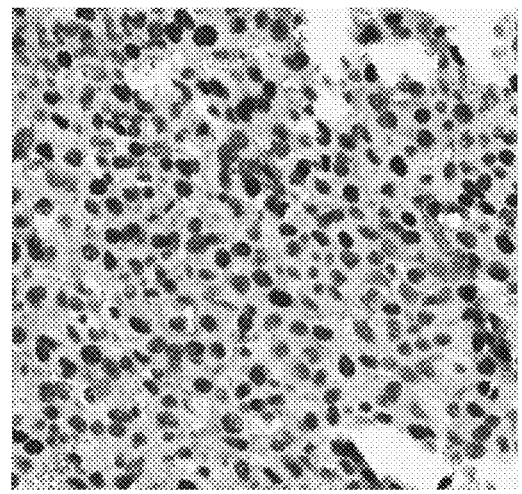
Figure 28E:
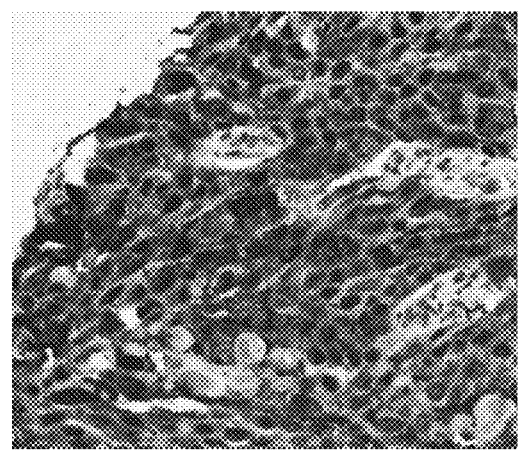

A second set of patient samples was collected from bladder tumors in patients with muscle invasive bladder cancer (FIGS. 28D & 28E). A human cisplatin-refractory bladder cancer tissue microarray (CisR-TMA) was created from this cohort of 36 patients that were noted to have residual disease at time of cystectomy despite preoperative neoadjuvant cisplatin-combination chemotherapy. Bladder tumor specimens for the CisR-TMA were obtained in duplicate 3-mm cores from formalin fixed paraffin embedded cystectomy samples. A total of 36 separate patient samples were obtained, all of which were treated with preoperative cisplatin-combination chemotherapy. The average age was 64±8 yrs, 19% were female, and cystectomy surgery was performed between 2007-2017. Median survival after cystectomy was 33±12 months, with greater than 70% of patients undergoing additional systemic treatments in the adjuvant setting or at time of relapse.

Tissues were fixed overnight at room temperature in 10% NBF (neutral buffered formalin), then transferred through graded concentrations of alcohol to xylene inside a tissue processor. Processed tissues were embedded in paraffin before being microtomed into 5-micron sections, mounted on positively charged slides and baked at 60° C. Sections from the CisRef-TMA were stained with the APE1/Ref-1 antibody by the Indiana University School of Medicine Research Immunohistochemistry Facility (Indianapolis, Ind.) and quantified using the HALO image analysis platform (Indica Labs). Basic histology of these specimens was performed by H&E staining; this was used to assess any underlying inflammation and the pathological features of bladder tumors or any underlying pathology that may have been present in the controls, which disqualified them from use. H&E analysis revealed that the tumors exhibited mostly epithelially confined loci of tumors, but all had some elements of invasive lesion formation, consistent with clinical expectations of specimens from patients that have failed cisplatin therapy.

Immunofluorescence and Immunohistochemistry (IHC)

Sections were rehydrated routinely and treated with heat-induced antigen retrieval in 10 mM citrate buffer (citrate buffer stock solution of monohydrate-free acid citric acid, sodium citrate dehydrate, pH 6.0) for 10 minutes followed by 10 minutes rest. Sections were then treated with a protein block at ambient temperature with a bovine serum albumin (BSA)-Donkey serum mixture for 2 hours and incubated with primary antibody overnight at 4° C. Primary antibodies and dilutions included rabbit survivin (1:100, Cell Signaling Technologies), mouse APE1/Ref-1 (1:200, Novus Biologicals), rabbit BrdU (1:200, Cell Signaling Technologies), and mouse PanCK (1:200, Cell Signaling Technologies). Sections were washed with 1×PBS (Phosphate-buffered saline)-Tween and incubated with IgG Alexa 488 and IgG Alexa 594-conjugated secondary antibody against rabbit or mouse for 1 hour at room temperature (1:200, Invitrogen), followed by 10 minutes incubation with Hoechst 33258 nuclear stain (1 µg/ml). Tissues were washed with 1×PBS-Tween and water and then covered with an aqueous medium/glass coverslips. The sections were analyzed for immunofluorescence intensity using a Leica 6000 epifluorescence/confocal microscope. IHC was conducted as previously published for APE1/Ref-1.

Drugs

APX3330, which is also called E3330, was synthesized and used as previously described (Nyland R L, et al., J Med Chem. 2010; 53(3):1200-10.). APX2009 and APX2014 were kind gifts from Apexian Pharmaceuticals LLC (Indianapolis, Ind.). Synthesis, description, and molecular target verification of APX2009, APX2014, and RN7-58 have been previously described in Nyland R L, et al., J Med Chem. 2010:53(3):1200-10; Sardar P., et al., Journal of Exp Therapeutics. 2018:367(1)108-118). The concentrations defined in this Example are within the specific activity concentration range of each inhibitor. Additionally, the concentrations are within the achievable levels in patients. Molecular target confirmation is routinely done via assessment of protein or gene expression of known pathway targets.

Cells in Culture

The following cell lines were obtained from the ATCC in 2016 and have been maintained in the laboratory since: Grade 3/4 transitional cell carcinoma (TCC) line UC3; Grade 3 papillary urothelial carcinoma T24; Grade 1 TCC line SW-780; Grade 1 papillary urothelial RT-4; squamous bladder cancer line SCaBER; and non-cancerous human urothelial cell (HUC). Cells were grown in RPMI medium supplemented with antibiotic and 10% fetal bovine serum (FBS) for 2 passages, after which stocks were made and deep frozen in liquid nitrogen. From these laboratory stocks, cells for all experiments have been recultured, with a maximum of 10 passages performed before returning to the laboratory stocks for fresh cultures. All cells are authenticated regularly (1× per year) to verify cell line integrity at the University of Arizona Genetics Core: (uagc.arl.arizona.edu/cell-line-authentication), and all are routinely tested and verified as *mycoplasma*-free.

Alamar Blue Assay

Bladder cancer cell lines (BLCAb001 (RP-B-01) and BLCAb002 (RP-B-02) maintained in RPMI growth medium with 10% FBS were plated at 4,000 cells/well in poly-D-lysine treated 96-well clear bottom black plates and grown overnight in 5% $CO_2$ at 37° C. Cells in monolayer were then treated with increasing concentrations of redox-specific inhibitor APX3330, APX2014 or APX2009 and serially diluted 1:2 in a 5-point dose scheme. For combination studies, cells were treated with both cisplatin and APX compounds to determine efficacy. After 72 hours, fresh RPMI medium with 5% FBS was exchanged, and a fluorescent metabolic indicator, Alamar Blue was added to each well at 10% final concentration. After a 4 hour incubation, plates were read on a Synergy H4 (Bio-Tek) plate reader. For each drug dose, background was subtracted and then further normalized to media alone.

BrdU Labeling and Proliferation Quantification

To determine the proliferation rate of cells in response to APE1/Ref-1 redox inhibitors, cells were grown in the culture conditions described above and treated with inhibitors as described above, in chamber slides. After 24 hours in culture with inhibitors or vehicle, all cells were treated with 3.1 µg/ml BrdU (in sterile PBS; 0.1%) for one hour. Cells were fixed and permeablized with 4% paraformaldehyde and stained for BrdU incorporation with the antibody and methodology described in the Roche BrdU labeling Kit, (Risch-Rotkreuz, Switzerland), using secondary antibodies. Positive cells were captured on a Leica 6000 fluorescent microscope and were quantified relative to Hoechst positive nuclei (total live cells).

Apoptosis Labeling Via Incucyte Caspase-3/7 Reagent

UC3 and T24 cells were plated in 96-well plates at 3,500 cell/well and allowed to attach overnight. Increasing amounts of APX2009 or APX2014 were added to each well along with 1 µM of the caspase reagent (Caspase-3/7 Red, Essen Bioscience) and then the cells were allowed to recover for 2 hours prior to beginning imaging with the Incucyte system (Essen Bioscience). Each well was imaged for phase contrast as well as red fluorescence every 2 hours for 96 hours. The Incucyte software generated movies of the cells following treatment as well as real-time imaging data with red fluorescence normalized to the percent confluency of the well.

Transfection of APE1/Ref-1 siRNA

All siRNA transfections in T24, UC3, RP-B-01 and RP-B-02 cells were performed using the Lipofectamine RNAimax Reagent (Thermofisher) protocol as described in Fishel et al., DNA Repair (Amst). 2008; 7(2): 177-86; Logsdon et al., Mol Cancer Ther. 2016; 15(11):2722-32; and Fishel et al., J Biol Chem. 2015; 290(5):3057-68. The APE1/Ref-1 siRNA sequences were: SEQ ID NO: 1: GTCTGGTACGACTGGAGTA and Life Technologies Cat #s1446 (SEQ ID NO: 2: CAGATATACTGTGCCTTCA). Twenty four hours post transfection, cells (1,500/well) were replated in xCELLigence plates, and growth was measured in real time using the xCELLigence RTCA system. For the RP-B-02 cell line, 1,500 cells/well were replated in 96-well black plates and cell growth determined over five days using the Alamar blue assay. Alamar blue assay was used with the RP-B-02 cells due to the fact that they did not attach and proliferate proficiently on the xCELLigence plates. Samples for western blotting were collected 72 and 144 hours post transfection of cancer cells with APE1/Ref-1 siRNA and scrambled siRNA control.

Western Blot

Whole cell extracts were prepared using RIPA (radioimmunoprecipitation) buffer containing protein inhibitors (1:100 PMSF, 1:100 orthovanadate and 1:100 protease inhibitor). Total protein concentration was determined via Lowry or BCA assay. 10-50 μg/well of each lysate was separated by SDS-PAGE using a 12% SDS-polyacrylamide gel. Blots were blocked with 5% nonfat dry milk in 1×TBS for 1 h and incubated overnight with primary antibodies to either APE1/Ref-1 (1:1000 dilution, Novus, NB-100-116), survivin (1:1000, Cell Signaling), Cyclin D1 (1:500, Abcam), PARP-1 (1:1000, Cell Signaling) or GAPDH (1:5000, Cell Signaling). After blots were washed three-six times with TBS-Tween, blots were incubated with HRP-conjugated secondary mouse antibodies (1:5000, Pierce). After washing three-six times with TBS-Tween, blots were visualized by enhanced chemiluminescence (West Pico/West Femto, Pierce).

Three-Dimensional (3D) Spheroid Growth Assays

RP-B-01 and RP-B-02 cells were resuspended in normal growth media containing 3% Reduced Growth Factor Matrigel (BD Biosciences) at a cell density of 1,500 and 3,000 cells/well, respectively and plated in ultra-low adherence 96-well plates (Corning).

Spheroids were allowed to form and then treated on days 4, 8, and 12 following plating with media containing 5% serum, 3% Reduced Growth Factor Matrigel, and APE1/Ref-1 inhibitors. Vehicle control, DMSO, was less than 0.01% of the volume, and was equivalent in each well. On Day 15, Alamar blue reagent (LifeTechnologies) was added to each well (10 μL/well) and incubated for 24 hours. $IC_{50}$s were calculated for each compound using a line of best fit (i.e., linear regression model) where the percent survival equaled 50% (n=3-4).

In Vivo Subcutaneous Tumor $10^7$ T24 human bladder cancer cells were grown in conditions described above and harvested with 0.05% Trypsin, centrifuged, and resuspended in a 50:50 solution of Matrigel: RPMI medium. For each subcutaneous tumor, a 100 μl volume of this suspension was implanted in the hind flank of male athymic nude male and female mice. Previous characterization of the T24 model indicated that log phase was entered when tumor volumes reached 65 to 150 mm$^3$ (between 2-4 weeks post-implant to reach log phase). At this point, and individual, for each animal, the animals were treated with either 50 mg/kg APX3330, 25 mg/kg IP APX2009 or vehicle (both in Propylene Glycol Kolliphor HS15 Tween 80 (PKT)) every 12 hours for up to 12 days. BrdU was injected into the animals 2 hours prior to sacrifice and tumor tissues were harvested and split into either snap frozen tissues for protein harvest and molecular analysis or fixed in formalin and processed for histological analysis, and then analyzed for survivin, Cyclin D1 levels (immunofluorescence and immunoblotting) for target protein assessment and BrdU incorporation (immunofluorescence).

Statistical Analysis $IC_{50}$ values for all dose response curves were calculated using ANOVA with Tukey post hoc analysis of all cell lines in monolayer and 3D cultures. The caspase time course curves were analyzed using Prism 6 software and generating linear regression curves for each treatment. The linear regression data indicated that all slopes were significantly different from each other and from vehicle control ($p<0.05$, n=2-4).

Results

Figure 29A:
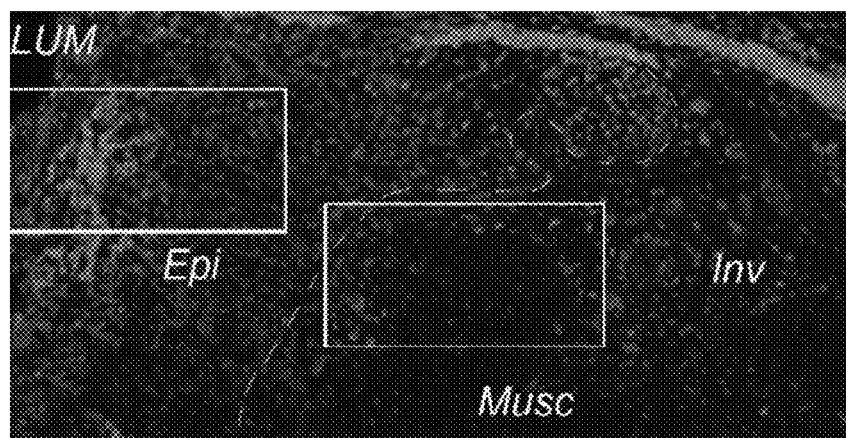
FIGS. 29A-29D. APE1/Ref-1 localization in human tumors. Additional examples of APE1/Ref-1 immunofluorescence in human bladder cancer specimens at 10× and 40×. Lower power (10×) (FIG. 29A) demonstrates transition from nuclear localized APE1/Ref-1 in the epithelial compartment (Epi) to cytosolic staining in the invasive regions of a human tumor, in the muscularis (Musc) in a single image, with high power (40×) views showing the cellular localization (FIGS. 29B & 29C). Additional examples in high power are shown in FIG. 29D, from 3 different specimens (1-3), exclusively nuclear staining in the epithelial compartment (Epi) and cytosolic staining in the invasive satellite lesions (INV).
Figure 29B:
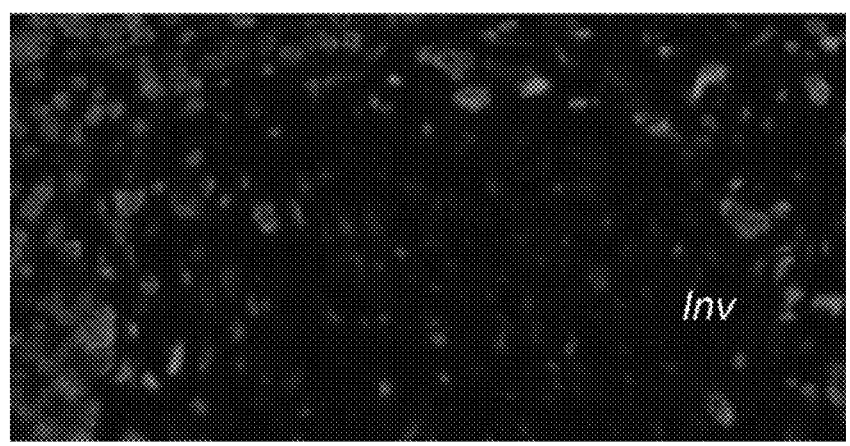
Figure 29C:
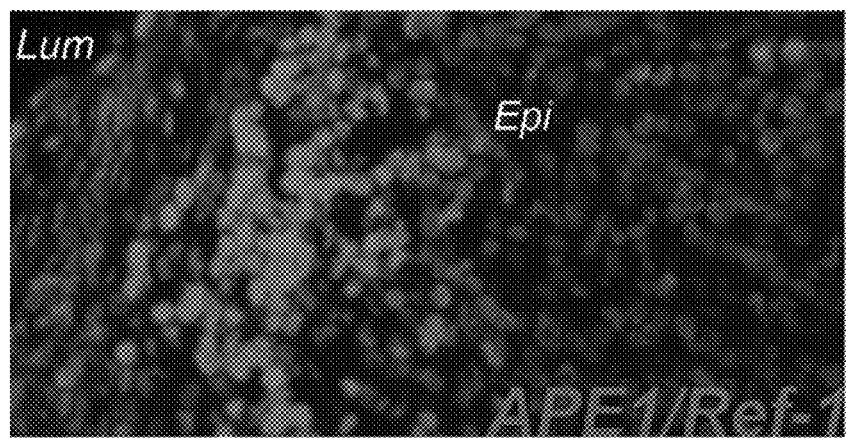
Figure 29D:
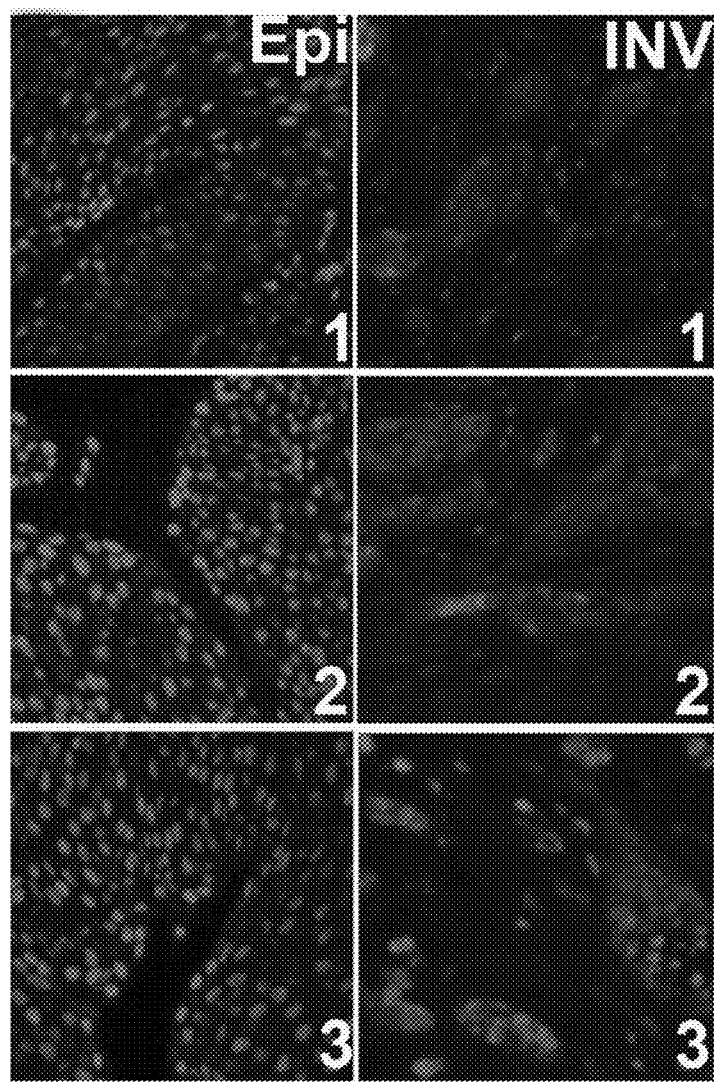

APE1/Ref-1 is highly expressed in bladder cancer compared to benign bladder urothelium and in multiple bladder cancer cells lines. To investigate APE1/Ref-1 redox signaling in bladder cancer, we obtained bladder cancer patient samples and stained for APE1/Ref-1 via immunofluorescence (IF, FIGS. 28A-28C) as well as immunohistochemistry (IHC, FIGS. 28D & 28E). Benign bladder urothelium showed low nuclear staining in the urothelium (FIG. 28A, representative of n=12). Strong nuclear fluorescence was observable in the tumor cell epithelia in all bladder cancer cases examined (FIGS. 28B & 28C, representative of twelve specimens from bladder cancer, See FIGS. 29A-29D for additional staining). Expression is primarily nuclear in non-invasive tumors as determined by the presence of satellite lesions in the muscularis of the tissue by H&E (FIG. 28B), but exhibits both nuclear and a stronger cytosolic pattern in invasive lesions where microsatellite growths occur in detrusor muscle (FIG. 28C, FIG. 29A). In calculation, 77±11% of cells in muscle-invaded satellite lesions exhibited nuclear staining, while 2.8±0.6% exhibit any detectable cytosolic staining by ImageJ.

Figure 28F:
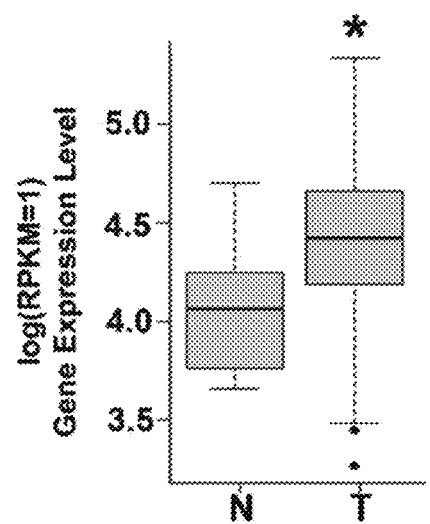

APE1/Ref-1 protein expression in cisplatin-refractory patient samples. 36 cisplatin-refractory patient samples were obtained, a TMA (tissue microarray) was constructed, and IHC staining of APE1/Ref-1 was performed. FIGS. 28D & 28E confirm the intense nuclear staining in the tumor cells within samples in the TMA, as well as the nuclear localization of APE1/Ref-1 in urothelial-confined tumor (FIG. 28D) with a stronger cytosolic expression in invasive tumor in addition to nuclear APE1/Ref-1 expression (FIG. 28E, n=36). Samples within The Cancer Genome Atlas (TCGA) confirmed that APE1/Ref-1 mRNA (APEX1) was significantly upregulated in bladder cancer patients compared to matched control (FIG. 28F, p=1.68e-05, Mann Whitney test). RNA-seq V2 data of the TCGA BLCA data were used for the analysis. Mann Whitney test was used for the differential gene expression test.

The observation that APE1/Ref-1 localization in the cytosol, specifically in the muscle-invading satellite lesions, but not the epithelially-confined tumors, may have important ramifications for using redox-specific APE1/Ref-1 inhibitors for muscle-invasive disease. Unlike the DNA repair function of this enzyme, the redox function could occur in either the nucleus or the cytosol, and therefore cytosolic localization could be a key indicator of redox function for this enzyme, and suggests a role for redox-specific inhibitors such as those described herein. Muscle-invasive disease is the deadly form of bladder cancer, and it is the form of the disease that metastasizes and for which very few treatment options have proven successful. Inhibition of Ref-1 may be a therapeutic option for bladder cancer patients with this deadly form of the disease.

Figure 28G:
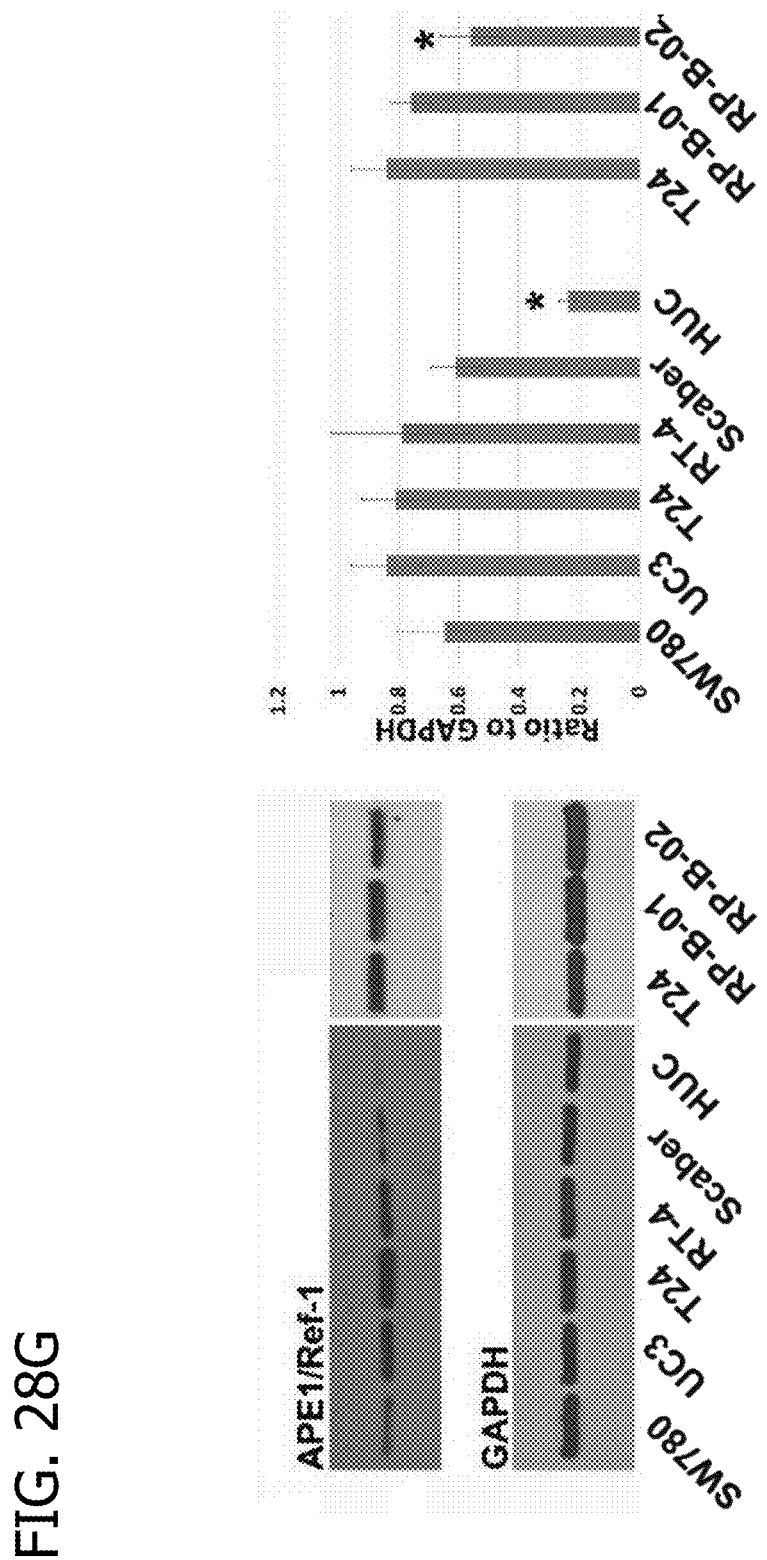

Human bladder cancer cell lines including SW-780, UM-UC3, T24, as well as the patient-derived xenograft lines RP-B-01 (B01) and RP-B-02 (B02) all express robust levels of APE1/Ref-1 protein (FIG. 28G). High levels of APE1/Ref-1 in patient samples, as well as patient-derived cell lines, support the investigation of APE1/Ref-1 as a target in bladder cancer. Furthermore, the RP-B-01 have been characterized as more cisplatin-resistant than the RP-B-02 cells, which was confirmed in vitro in FIGS. 30A & 30B. RP-B-01 were at least 3-fold more resistant to cisplatin than RP-B-02 cells, providing representative BCa cell lines to study APE1/Ref-1 signaling and response to inhibition.

Figure 31A:
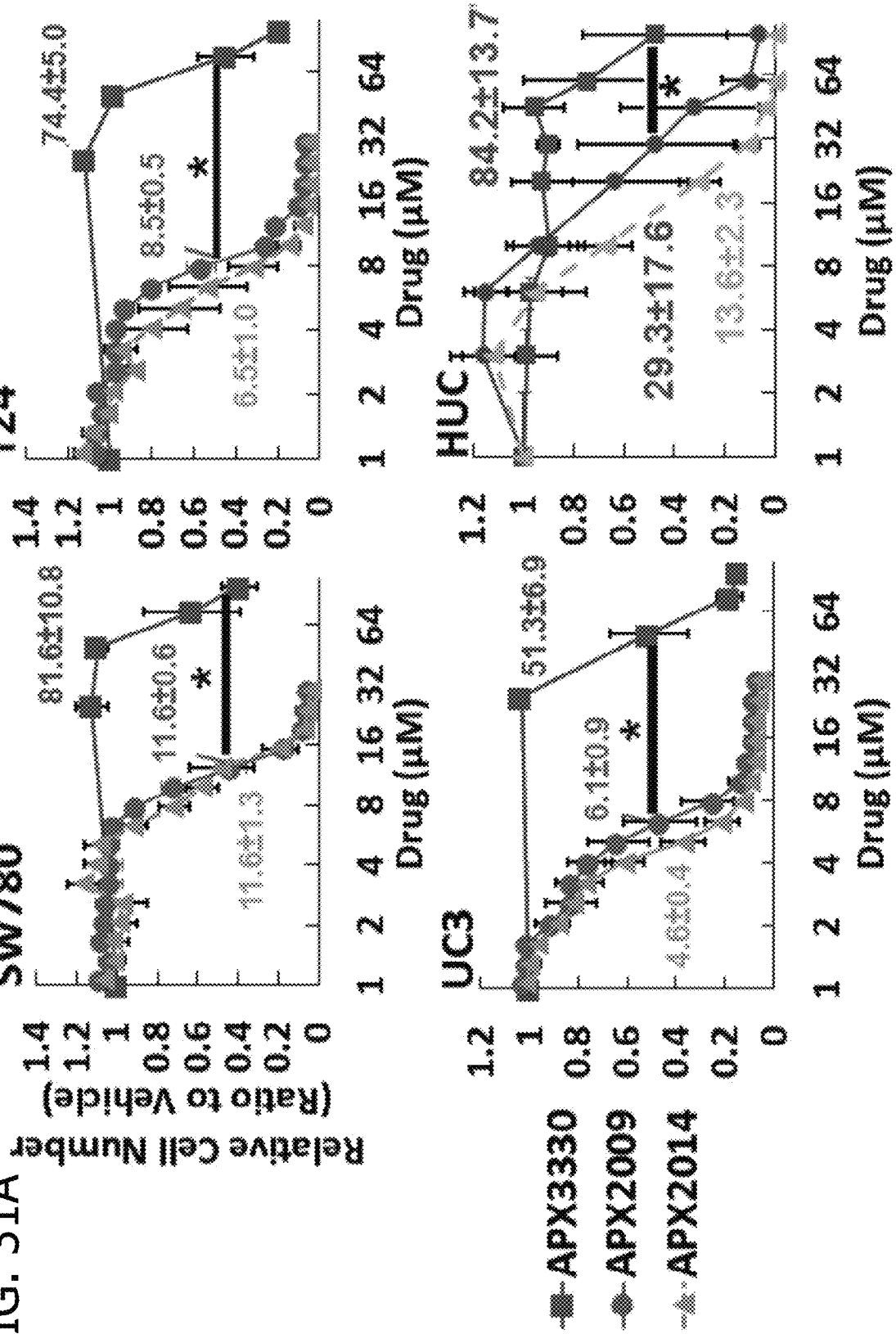
FIGS. 31A & 31B. Treatment with APE1/Ref-1 inhibitors potently blocks bladder cancer cell proliferation and activated Caspase 3/7. SW780, T24, UC3, and HUC cell lines (FIG. 31A) were treated with increasing concentrations of redox-specific inhibitor APX3330 (RED square), as well as the more potent analogs APX2009 (GREEN circle) and APX2014 (orange triangle). The $IC_{50}$ values for FIG. 31A were determined using the methylene blue assay, n=4. $IC_{50}$s were calculated and compared between the drugs, and are listed next to their curves in the figure; * denotes p<0.05 APX3330 $IC_{50}$ versus both APX analogs. T24 and UC3 cells were treated with APX2009 and APX2014 at the $IC_{50}$ and $IC_{90}$ and monitored over time for activation of capsase 3/7 by an increase in red fluorescence. Time course graphs are shown in FIG. 31B and representative images at 48 hr are shown in FIG. 32A (described more fully below), n=3-4. The curves are all significantly different from DMSO (p<0.05).

Bladder cancer cell proliferation was inhibited and apoptosis was induced by potent, selective redox inhibitors of APE1/Ref-1. A panel of bladder cancer cell lines including SW780, T24, UC3, and noncancerous HUC cells was used to investigate the effects of parent compound APX3330 and more potent analogs, APX2009 and APX2014 on bladder cancer cell proliferation and apoptosis. Data in FIG. 31A clearly demonstrates that the inhibition of APE1/Ref-1 redox activity potently and significantly reduced bladder cancer cell number in vitro. Analogs, APX2009 and APX2014 were significantly more potent in all cell lines tested ($p<0.0001$) compared to APX3330. The $IC_{50}$ values for APX2009 and APX2014 were 7- and 11-fold, respectively, lower than the $IC_{50}$s for APX3330. Notably, the noncancerous HUC cell line exhibited substantially less response to APE1/Ref-1 redox-selective inhibitors (FIG. 31A).

Figure 31B:
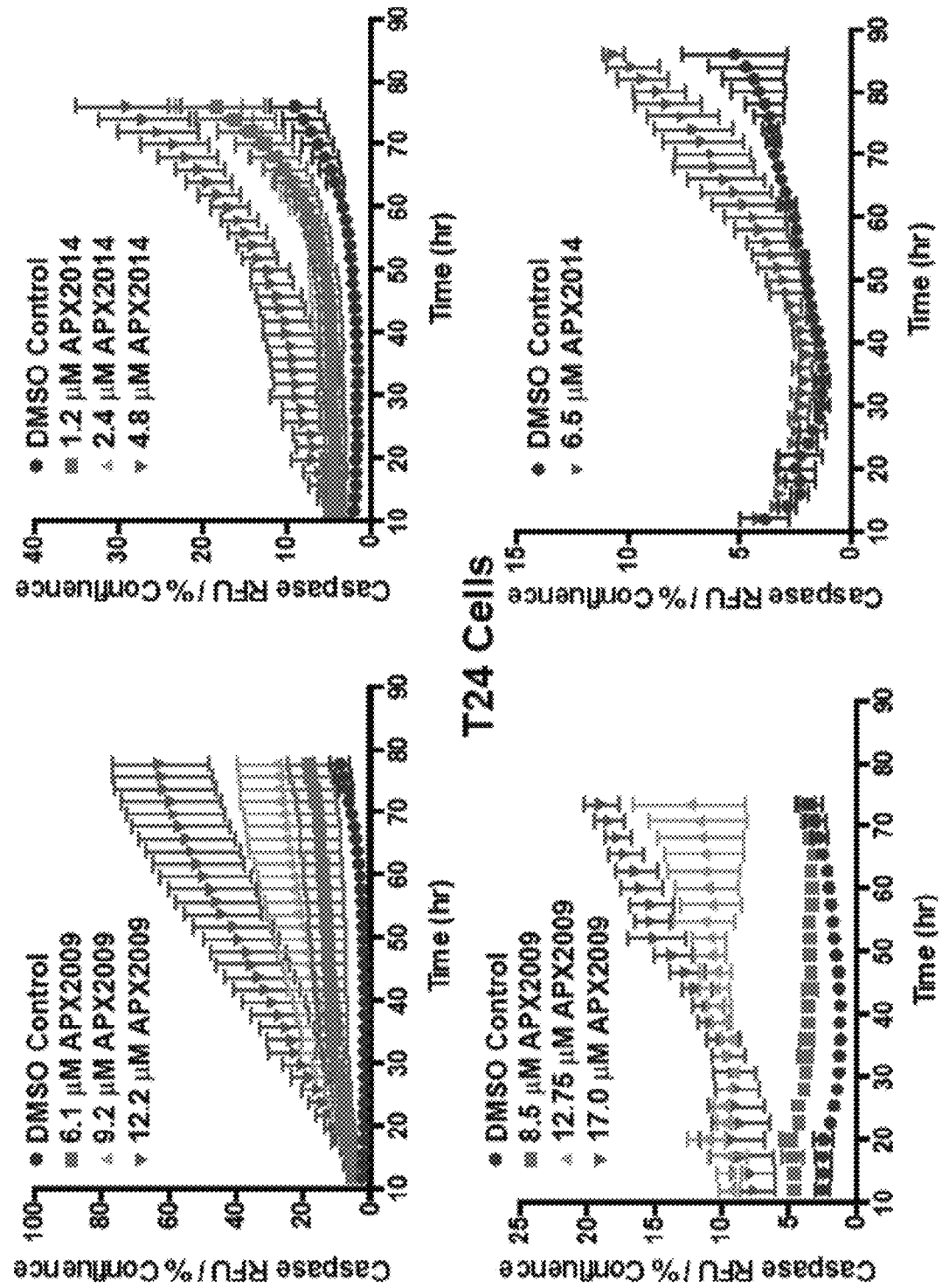

To further characterize this effect, it was analyzed whether this reduced cell number was due to decreases in proliferation, increases in apoptosis, or both. BrdU incorporation assay demonstrated that the number of BrdU-positive cells was reduced from 11.2%±0.84 to 7.8%±0.64 after treatment with $IC_{50}$ concentration of APX3330, to 6.9%±0.58 by the $IC_{50}$ concentration of APX2009, and to 7.2%±0.49 by the $IC_{50}$ concentration of APX2014 (all $p<0.05$ by ANOVA; n=4). Along with the observed decrease in proliferation, an increase in apoptosis was seen in both UC3 and T24 cells (FIG. 31B).

Figure 32A:
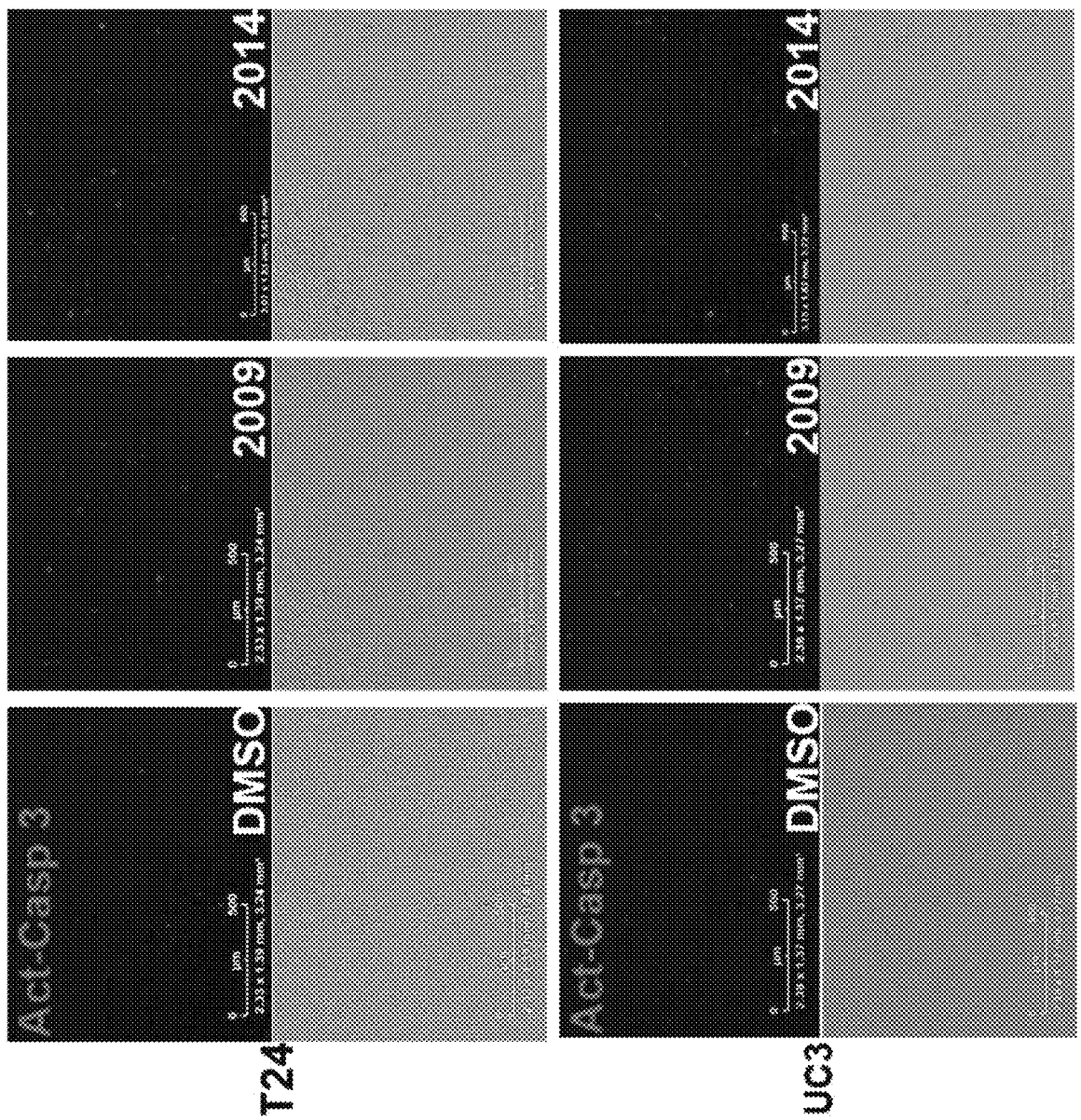
FIGS. 32A & 32B. Confirmation of cell death induction by caspase activity assay and PARP cleavage. Representative images for caspase activity via red fluorescence (FIG. 32A) for the data calculated and shown in FIGS. 31B & 32A, each with matching brightfield images. Representative examples for T24 and UC3 cells are shown form cells treated with the growth-inhibitor $IC_{50}$ concentrations for each drug, in each cell line. PARP cleavage was used to confirm the induction of apoptotic mechanisms by western blotting for cleaved PARP1 (FIG. 32B), with representative cell experiments in which UC3 cells were treated with $EC_{50}$ and $EC_{90}$ concentrations of each drug.
Figure 32B:
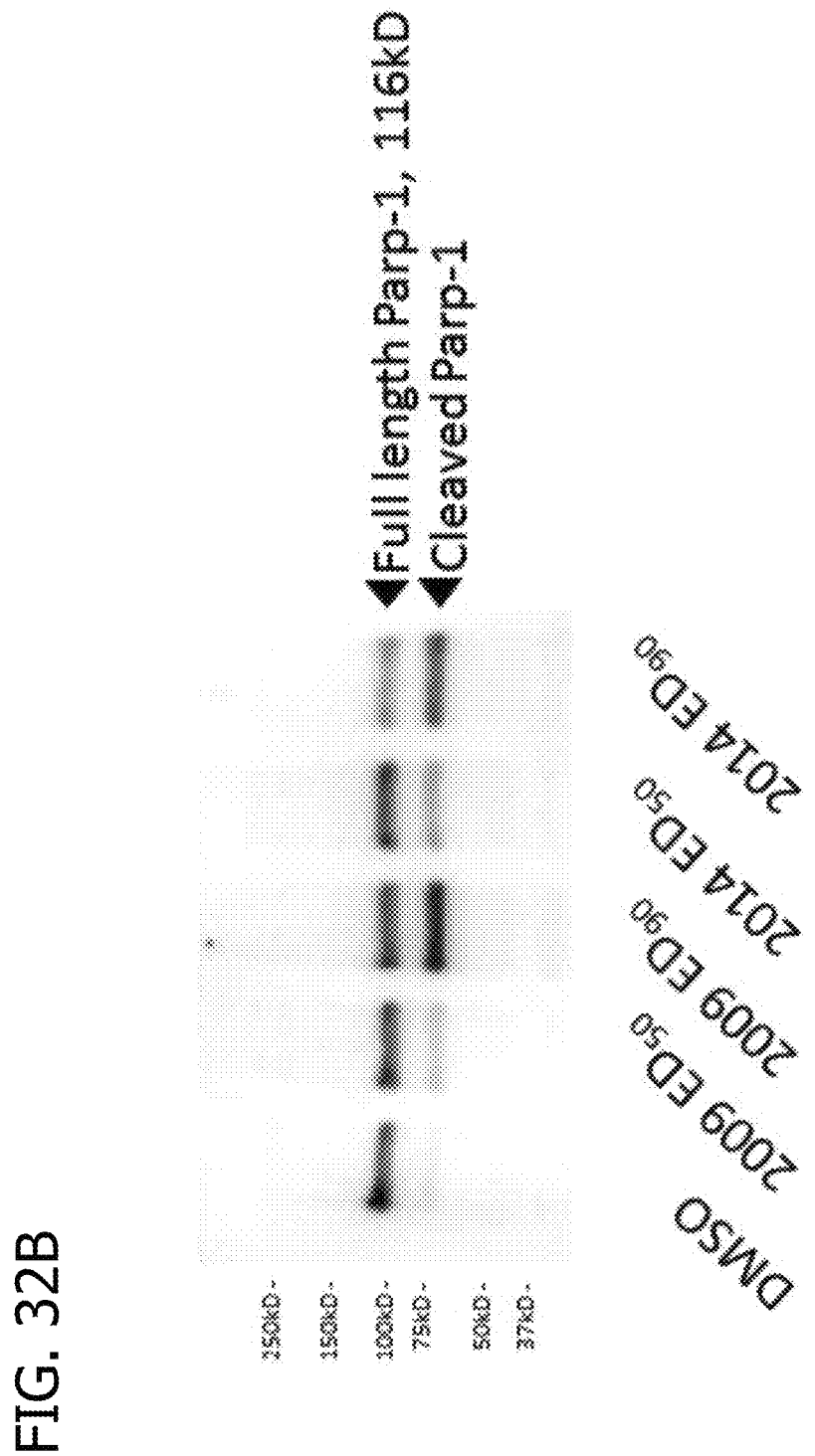

To assay for caspase-3/7 mediated apoptosis, the increase in red fluorescence was analyzed over time following the addition of APX2009 and APX2014. Representative images of the vehicle- and APX-treated cells at 48 hours are shown in FIGS. 32A & 32B. A dose-dependent increase in caspase activation was also accompanied by an increase in PARP-1 cleavage (FIG. 32B).

Figure 33A:
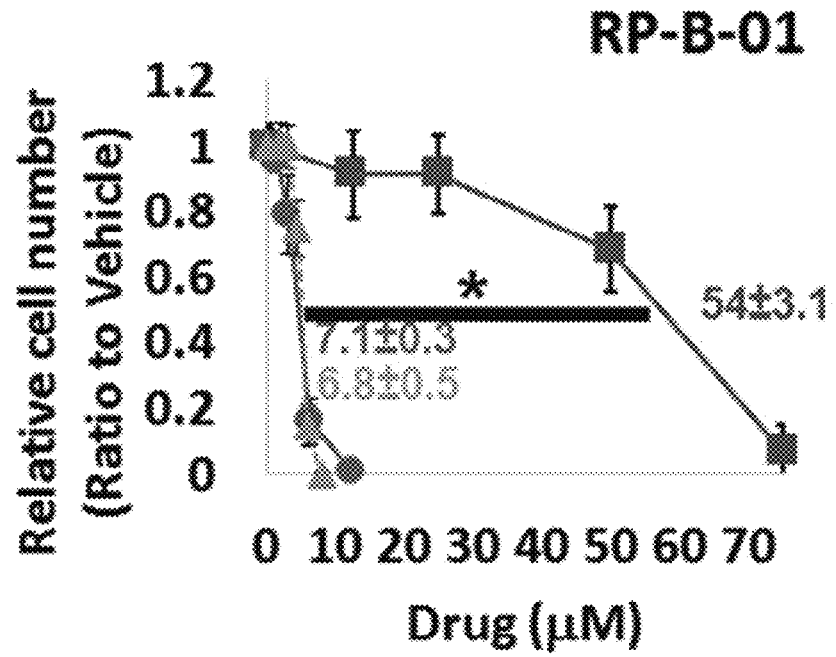
FIGS. 33A-33F. Inhibition of APE1/Ref-1 in monolayer and in three-dimensional (3D) culture using PDX-derived cells RP-B-01 and RP-B-02 blocks tumor growth. RP-B-01 and RP-B-02 cells were grown first in monolayer cell culture (FIGS. 33A & 33B, n=3), and then in 3D culture (FIGS. 33C-33F) and treated with APX3330, APX2009 and APX2014 over the course of 15 days (n=3-4±SE). Monolayer and spheroid growth was measured via Alamar blue and normalized to the fluorescence of media control. Representative images of spheroids treated with APX inhibitors are shown in FIG. 33E and FIG. 33F. The $IC_{50}$ values were determined (n=3.4±SE) and compared between the drugs using ANOVA with Tukey post hoc test: * p<0.05, **p<0.001 comparison of $IC_{50}$ of APX3330 versus APX analog; while # denotes p<0.01 APX2009 vs APX2014.
Figure 33B:
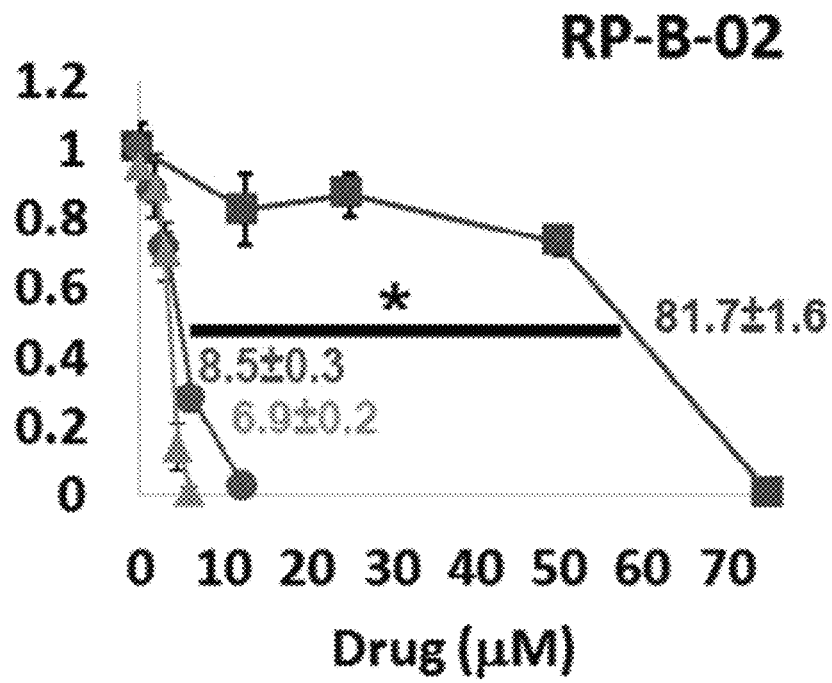

Blockade of APE1/Ref-1 inhibits PDX bladder cancer cell growth in monolayer and in 3D culture model. APE1/Ref-1 redox inhibition was also characterized in two additional bladder cancer cell lines that were derived from a patient-derived xenograft (PDX) model. Patient-derived cells demonstrated similar sensitivity to APE1/Ref-1 redox inhibition as established bladder cancer cell lines and were similarly more sensitive to analogs, APX2009 and 2014 (FIGS. 33A & 33B).

Figure 33C:
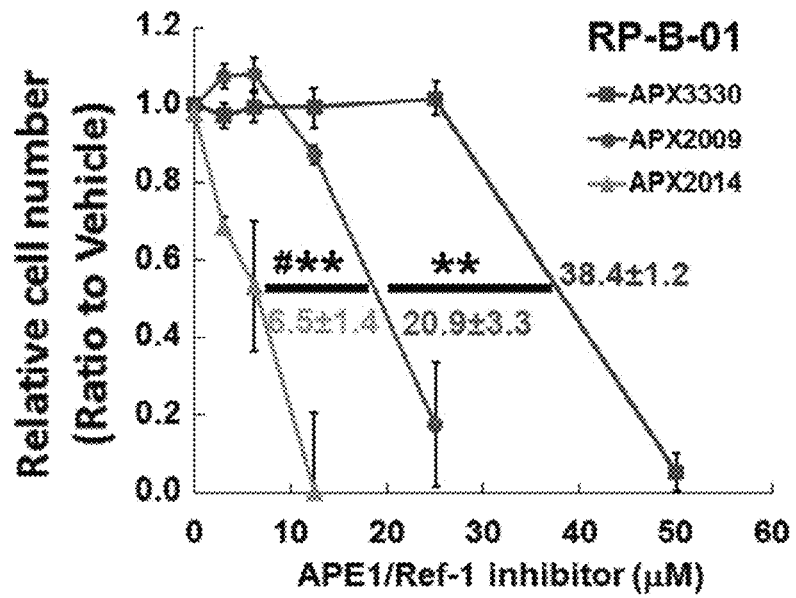
Figure 33D:
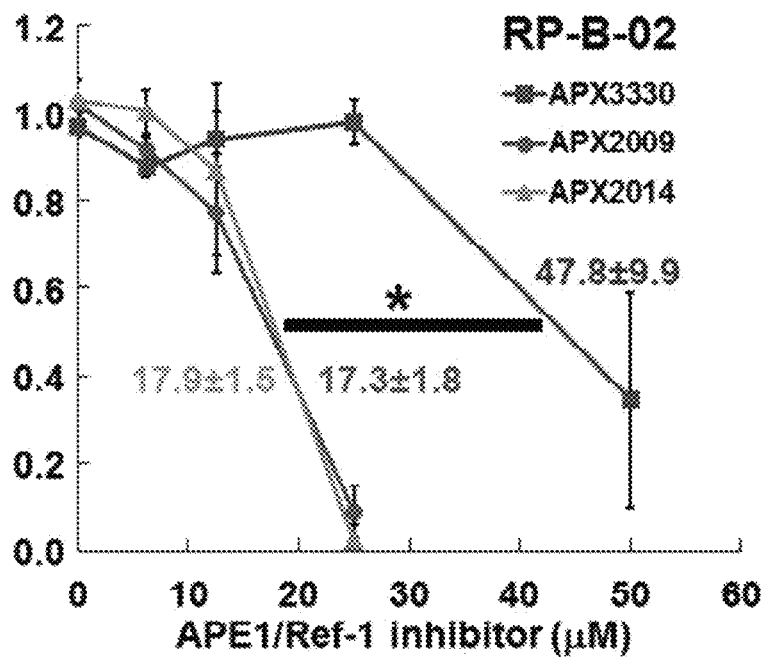
Figure 33E:
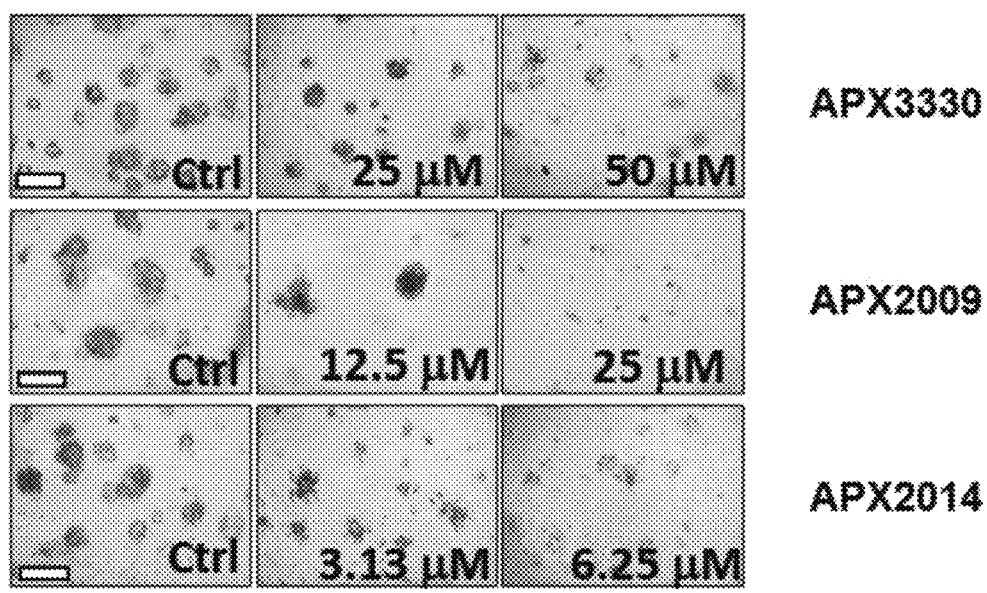
Figure 33F:
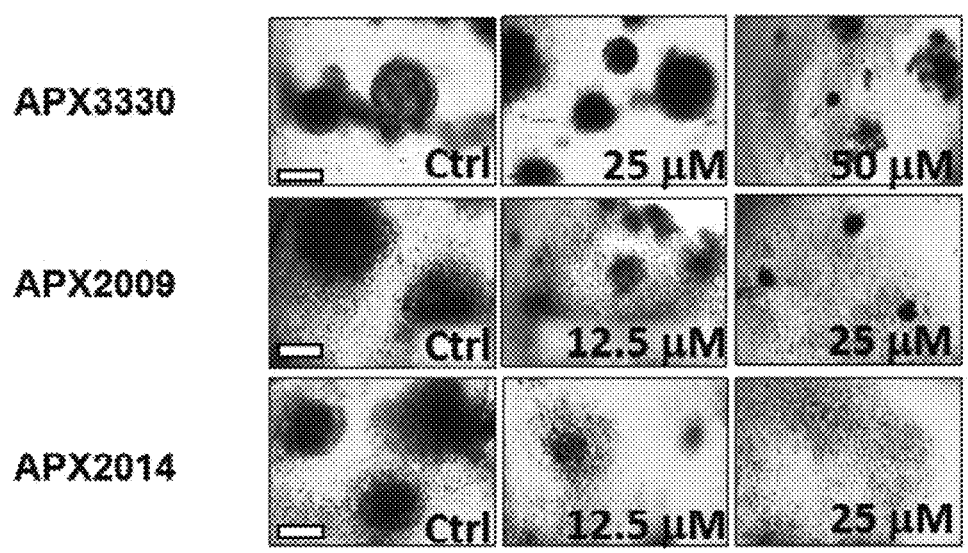
Figure 34A:
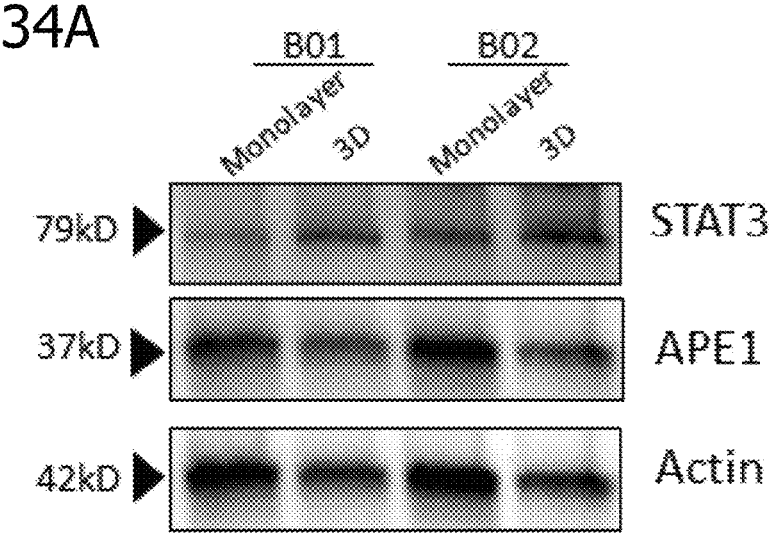
FIGS. 34A-34C. Confirmation of APE1/Ref-1 and STATS expression in 3D and monolayer conditions in RP-B-01 and RP-B-02 cells. Basal growth conditions as described in the methods for each cell line were used for monolayer and 3D conditions. No significant differences in expression relative to actin were observed in either condition. Representative blot is shown in FIG. 34A, and quantified data shown as the ratio of each protein to actin from 2 determinations is shown in FIGS. 34B &34C.
Figure 34B:
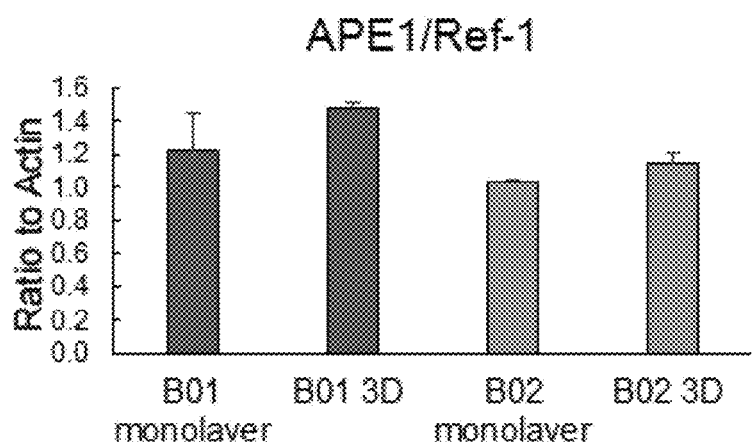
Figure 34C:
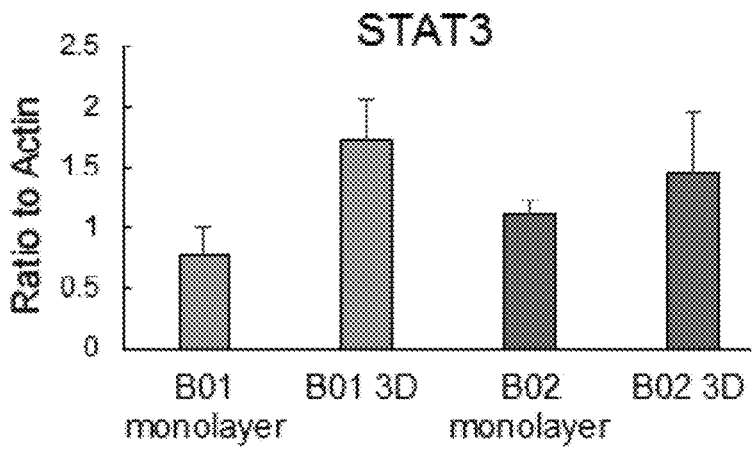
Figure 35A:
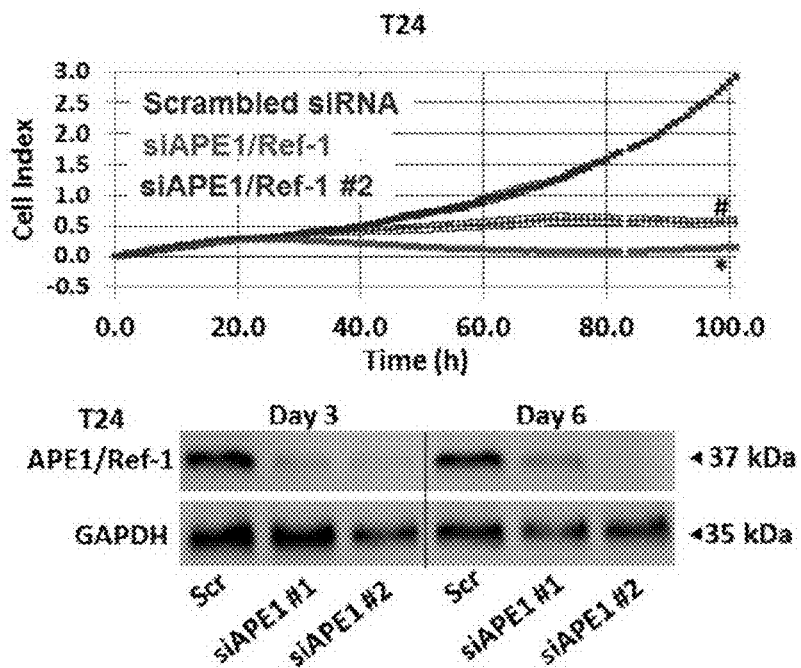
FIGS. 35A-35D. Reducing APE1/Ref-1 levels via siRNA dramatically slows down the proliferation of bladder cancer cells. T24 (FIG. 35A), UC3 (FIG. 35B), RP-B-01 (FIG. 35C) and RP-B-02 (FIG. 35D) were transfected with two distinct sequences of APE1/Ref-1 siRNA (50 nM) and growth was compared to Scrambled control (n=3, *p<0.05 (Scr vs siAPE/Ref-1 #1), # p<0.05 (Scr vs siAPE/Ref-1 #2) at 100 h). Cell index was monitored via xCELLigence system in FIGS. 35A-35C and fluorescence using Alamar blue assay was monitored over time in FIG. 35D. Western analysis confirmed the reduction in APE1/Ref-1 protein levels and GAPDH was used as a loading control.
Figure 35B:
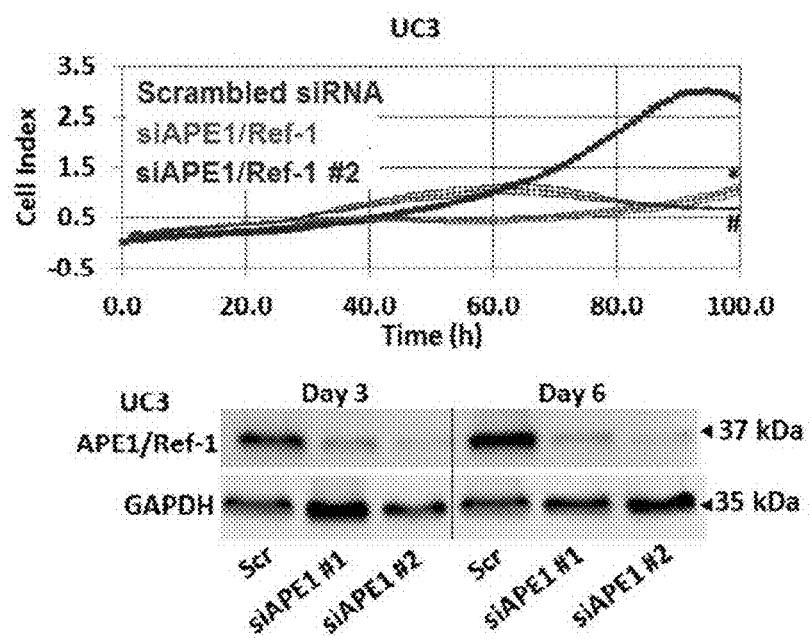
Figure 35C:
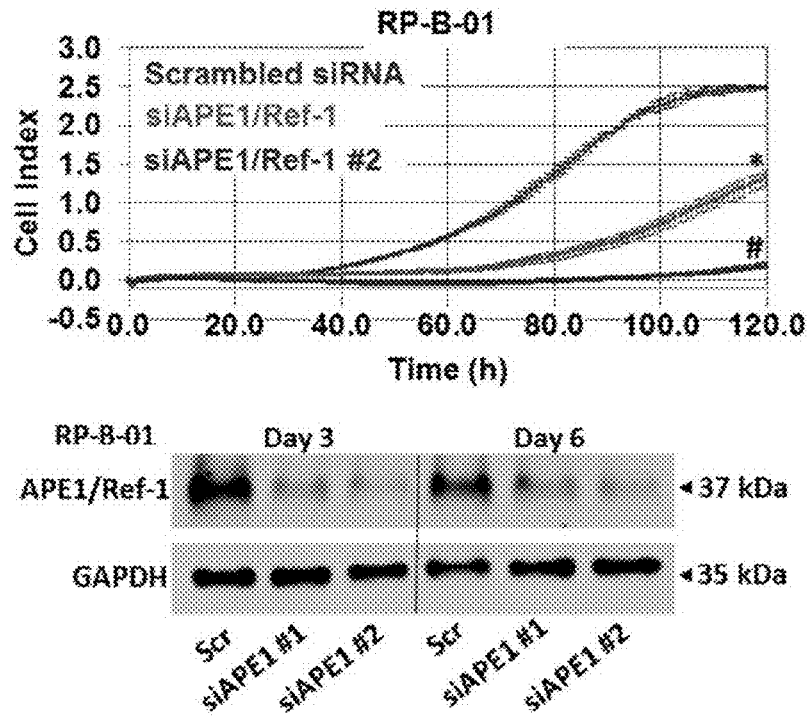
Figure 35D:
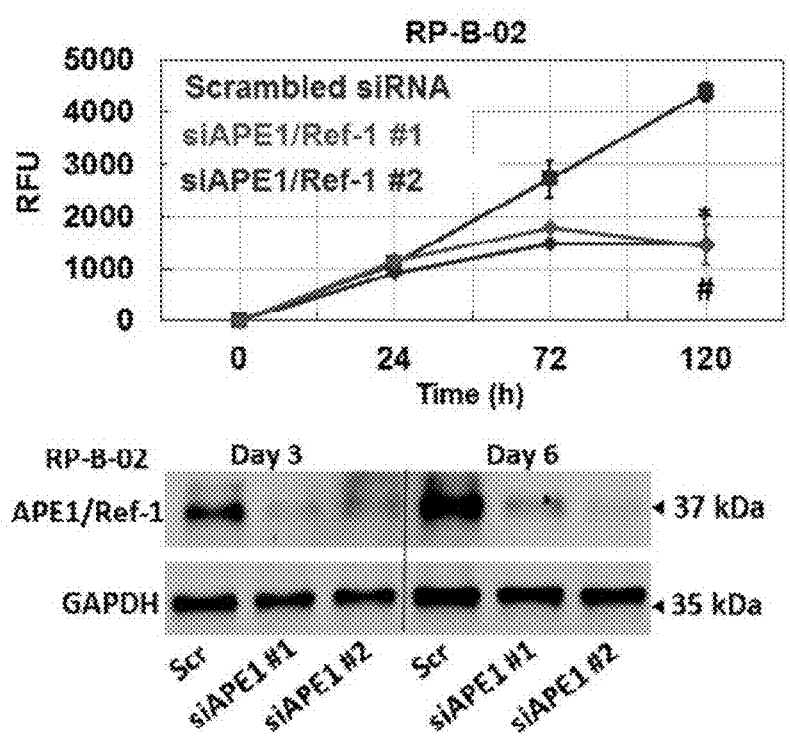

In order to mimic tumor growth more accurately in a relevant microenvironment and in a more robust model for predicting response to treatment, a three-dimensional (3D) culture model of patient-derived RP-B-01 and RP-B-02 bladder cancer cells was used. Both RP-B-01 and RP-B-02 cell lines are transitional cell carcinoma staged as T4bN1Mx and T2bN0Mx Grade III tumors, respectively. Using this 3D culture model, a dose-dependent decrease was observed in spheroid growth with all three APE1/Ref-1 inhibitors with a similar increase observed in potency for the new analogs, APX2009 and APX2014, as seen in monolayer (FIGS. 33C & 33D). One difference that was observed with the 3D culture compared to monolayer was that the RP-B-01 cells were significantly more sensitive to APX2014 than APX2009 (FIGS. 33C & 33E, $p<0.01$). APX2009 and APX2014 were more potent in the RP-B-02 cells than parent compound APX3330 ($p<0.05$), but were not significantly different from each other (FIGS. 33D & 33F). Both PDX cell lines exhibited similar expression patterns of both APE1/Ref-1 and its target STAT3 in 3D and in monolayer conditions, with no significant changes in these two critical proteins between either culturing conditions (FIGS. 34A-34C).

Blockade of APE1/Ref-1 via siRNA similarly reduced the ability of the bladder cancer cells to proliferate. To confirm the effects of APE1/Ref-1 inhibition on bladder cancer cell proliferation, bladder cancer cells were transfected with APE1/Ref-1 siRNA and the proliferative capacity quantified following APE1/Ref-1 knockdown. Using two siRNAs that are specific to APE1/Ref-1, the levels of APE1/Ref-1 protein were effectively reduced to greater than 70% over a 6-day period (FIGS. 35A-35D). T24, UC3, RP-B-01 and RP-B-02 cell lines were transfected with APE1/Ref-1 siRNAs, and growth of cells with reduced APE1/Ref-1 levels was compared to the Scrambled siRNA-transfected cells over time. The xCELLigence system was used to monitor cell attachment, proliferation, and morphology in real time. Bladder cancer cells transfected with APE1/Ref-1 siRNA grew at a significantly slower rate compared to those transfected with the Scrambled control siRNA (FIGS. 35A-35D, $p<0.05$ compared to Scrambled control, at t=100 h). Western blotting was performed Day 3 and Day 6 post transfection, and APE1/Ref-1 levels were found to be decreased compared to scrambled control at all timepoints tested.

Figure 36A:
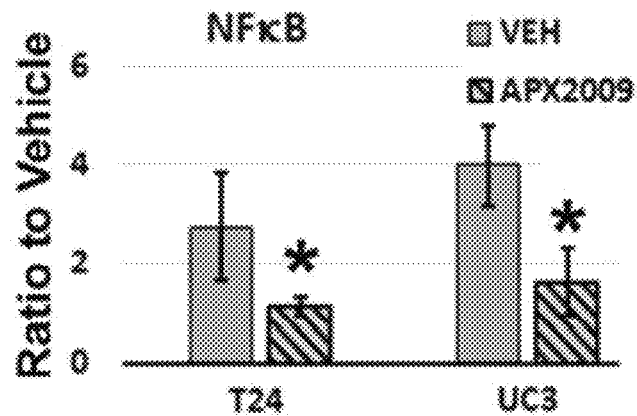
FIGS. 36A-36H. Redox-1 specific APE1/Ref-1 inhibition with APX2009 and APX2014 reduced the transcriptional activity of NFκB and STAT3 resulting in a decrease in expression of Survivin and Cyclin D1. In cytokine-induced T24 and UC3 cells NFκB-driven luciferase (FIG. 36A), STAT3-driven luciferase (FIG. 36B), and AP-1-driven luciferase (FIG. 36C) were quantified and normalized via *Renilla* following treatment with the corresponding cell growth-inhibitory $IC_{50}$ concentrations. T24 cells were treated with APX2009 (8.5 µM) and APX2014 (6.5 µM), and UC3 cells were treated with APX2009 (6.1 µM) and APX2014 (4.6 µM) for 24 h. (*-p<0.05 APX treated vs vehicle, n=4). APX2009 and APX2014 treatment also decreased expression of two verified NFκB and STAT3 targets, survivin and Cyclin D1 (FIG. 36D), as indicated by densitometry quantified immunoblots (right panel, *-p<0.05 APX treated vs vehicle, n=4). In the panels of FIGS. 36F & 36G, co-expression of survivin and APE1/Ref-1 was analyzed in superficial (FIG. 36F) and invasive human bladder tumors (FIG. 36G) in patients, and found nearly universal overlap of positivity in both in human samples. This was also true in cisplatin-refractory patients from the tissue microarray specimens (FIG. 36H).
Figure 36B:
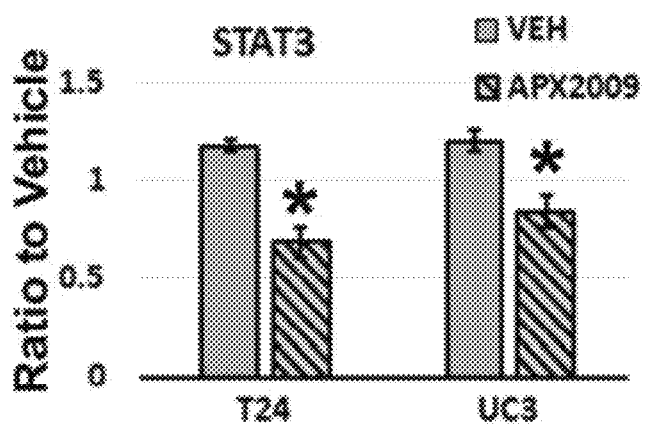
Figure 36C:
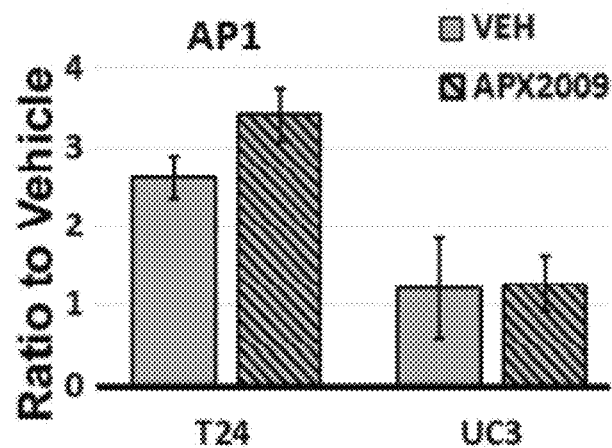
Figure 36D:
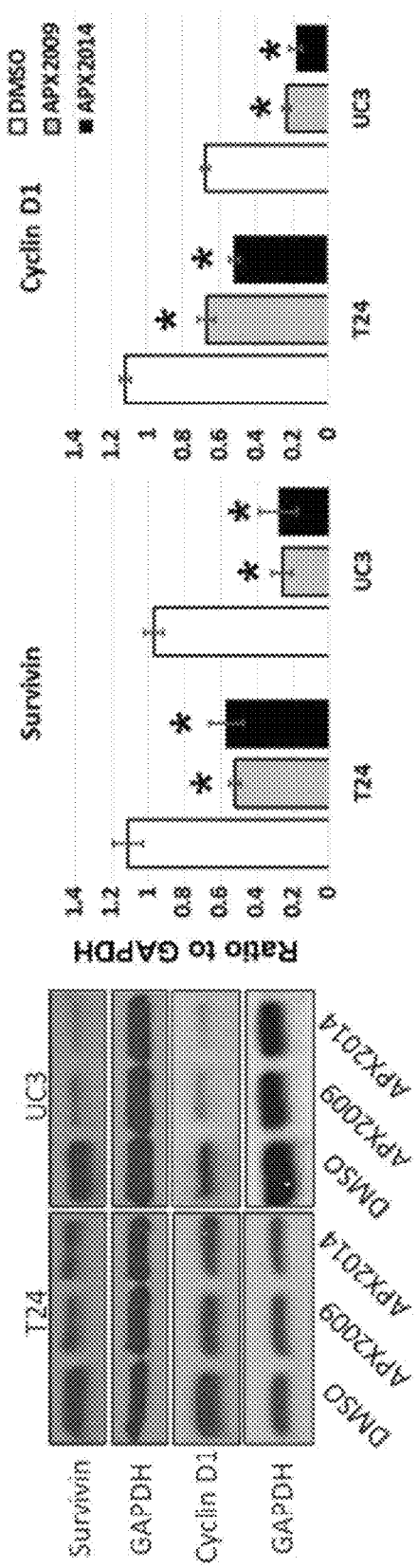

Redox-specific APE1/Ref-1 inhibition with APX2009 and APX2014 reduced the transcriptional activity of NFκB and STAT3 promoters as well as downstream expression of NFκB- and STAT3-regulated genes. The transcriptional activity of NFκB, STAT3, and AP-1 is under redox control by APE1/Ref-1. Therefore, NFκB, STAT3, or AP-1 transcriptional activity was quantified following treatment with APE1/Ref-1 redox inhibitors (FIGS. 36A-36C). In T24 and UC3 cells induced with the NFκB activator, TNFa, APX2009 significantly reduced NFκB-driven luciferase activity 2-fold (*-$p<0.05$ APX treated vs vehicle, n=4) Similarly STAT3 activity was significantly blocked in T24 and UC3 cells following induction with STAT3 activator IL-6, and treatment with APX2009 (FIG. 36B, *-$p<0.05$ APX treated vs vehicle, n=4). No effect on the transcription factor AP-1 was observed in these cell lines at the timepoints tested (FIG. 36C). These data show that following inhibition of APE1/Ref-1, the expected decrease in NFκB and STAT3 activity was observed.

Figure 36E:
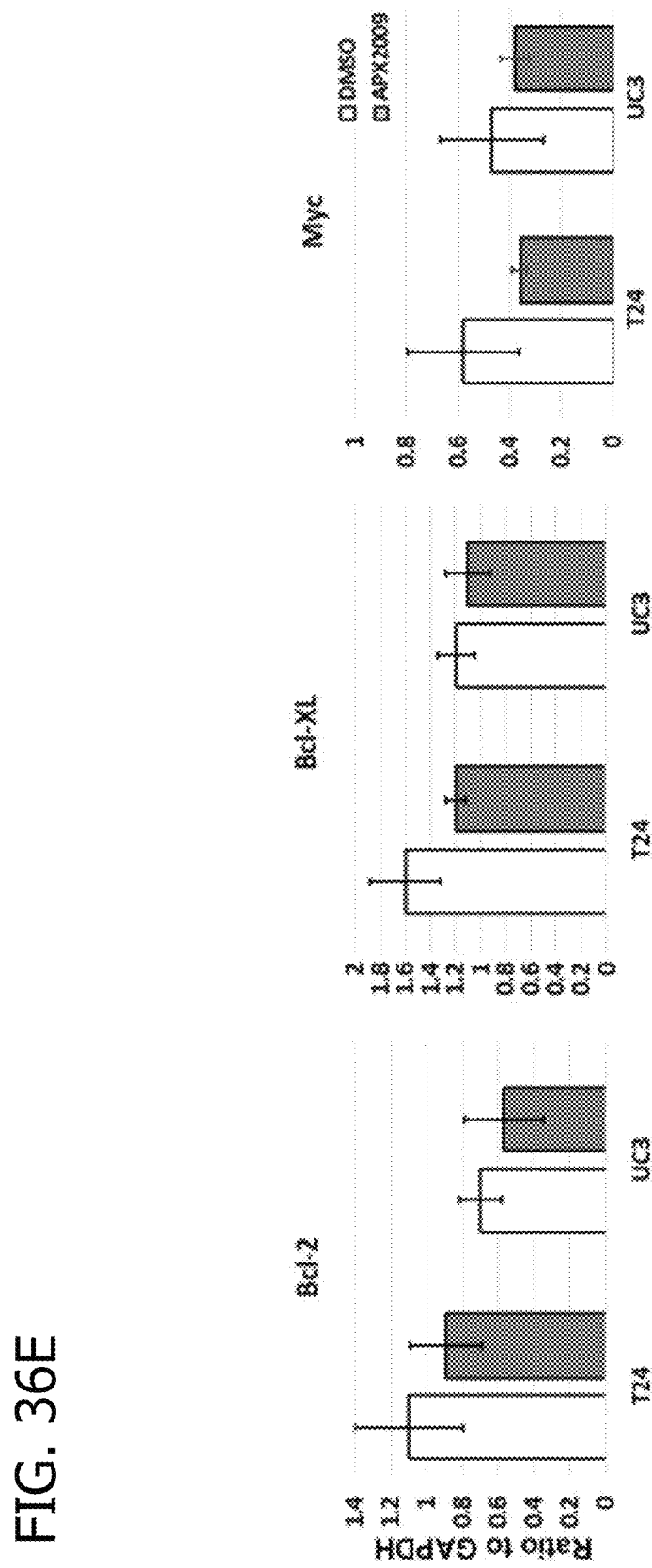
Figure 36F:
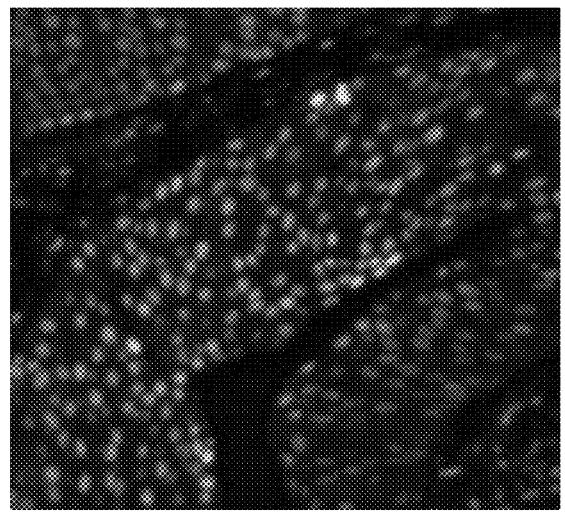
Figure 36G:
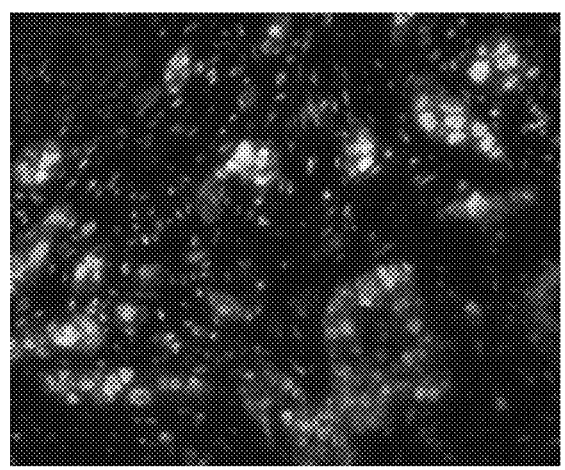
Figure 36H:
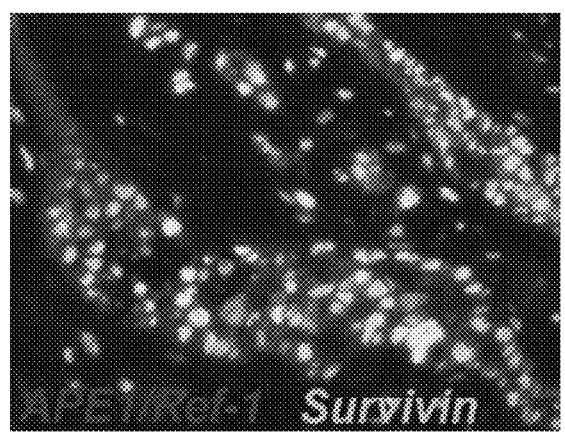

For further confirmation of a decrease in NFκB and STAT3 transcriptional activity, levels of survivin and Cyclin D1 were examined Both survivin and Cyclin D1 are known to be downstream targets of NFκB and STAT3. Following treatment with APX2009 and APX2014, the expression of two proteins, survivin and Cyclin D1, were significantly down-regulated, as shown in FIG. 30D. No change in expression was observed from other cell proliferation or cell survival proteins, including c-Myc, Bcl-2, or Bcl-XL (FIG. 36E). Co-expression of APE1/Ref-1 and survivin was also analyzed in superficial (n=12, FIG. 36F) and invasive human bladder tumors (n=12, FIG. 36G), and found a nearly universal overlap of positivity in both, as over 99% of cells positive for APE1/Ref-1 also demonstrated high levels of survivin. However, unlike APE1/Ref-1, survivin expression was primarily nuclear in both urothelial confined and invasive lesions. This result held true in dual fluorescence staining of the cisplatin-resistant TMA specimens (FIG. 36H).

In vivo blockade of APE1/Ref-1 redox signaling decreases tumor growth and proliferation with a corresponding decrease in the protein levels of NFκB/STAT3 target, survivin. Thus far, it has been demonstrated herein that APE1/Ref-1 is highly expressed in human bladder cancer, as well as PDX, and established cell lines and that blockade of this critical redox protein inhibits bladder cancer cell growth and reduces cell survival proteins such as survivin and Cyclin D1 in vitro. FIGS. 37A-37D demonstrates in vivo efficacy following inhibition of APE1/Ref-1 redox activity in subcutaneous T24 tumor growth (FIG. 37A), as mice treated throughout the growth period exhibited reduced graft tumor growth compared to vehicle-treated controls. At sacrifice, vehicle-treated animals bore tumors of 1.0±0.2 g on average, while tumors from animals treated with APX3330 were 0.43±0.10 g, and APX2009-treated tumors averaged 0.37±0.14 g (both p<0.05 compared to vehicle control). Due to the observed increase in potency of APX2009, similar tumor growth reduction was achieved to parent compound APX3330 at half the dose (APX3330 50 mg/kg and APX2009 25 mg/kg).

Figure 37A:
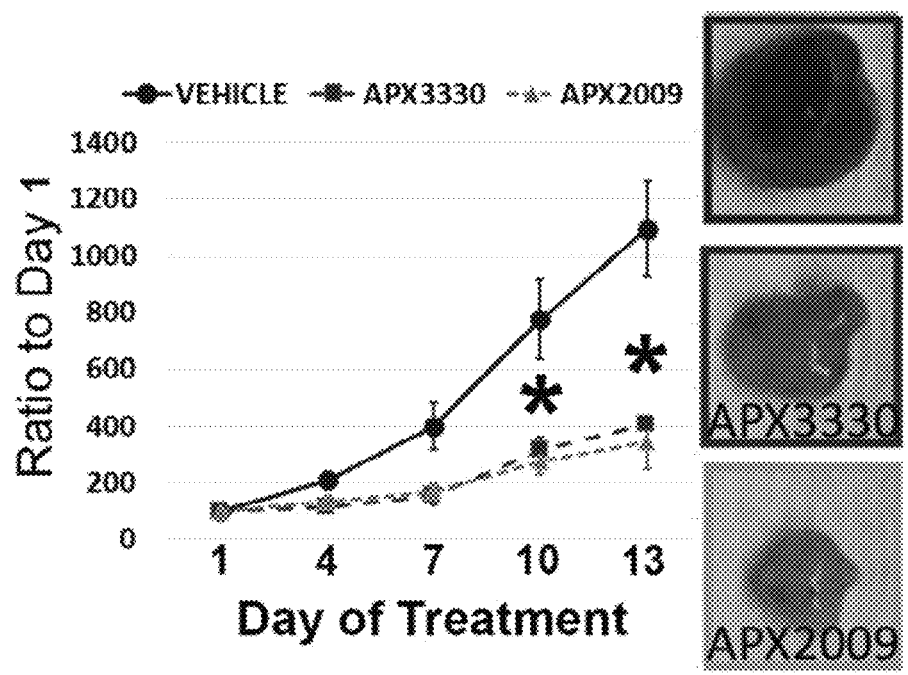
FIGS. 37A-37D. Treatment with APX3330 and APX2009 exhibited significantly reduced tumor growth and proliferation in vivo compared to vehicle control. Tumor growth delay following treatment with APX compounds in T24 flank xenografts with images of representative size of tumors shown in FIG. 37A. Mice were treated with APX3330 (50 mg/kg, ip) and APX2009 (25 mg/kg, ip) twice daily for the duration of the experiment. Tumor growth was normalized to the tumor volume on Day 1, when treatment was started (FIG. 37A, *p<0.05, n=8 animals per group). Proliferation following treatment as determined by BrdU labeling and IF is pictured in FIG. 37B, with quantification shown in FIG. 37C (n=8; p<0.05). Harvested tumors also showed a reduction in survivin expression by both APX3330 (42%) and APX2009 (64%) with densitometry ratios to GAPDH shown in the blots, and a reduction in the ratio of cleaved caspase 3 to total caspase 3, as demonstrated by the densitometry data included in the blots as the ratio of cleaved to total caspase 3 (FIG. 37D, n=8, p=0.03). Representative immunoblots shown, and the average densitometry of 8 tumors is inset.
Figure 37B:
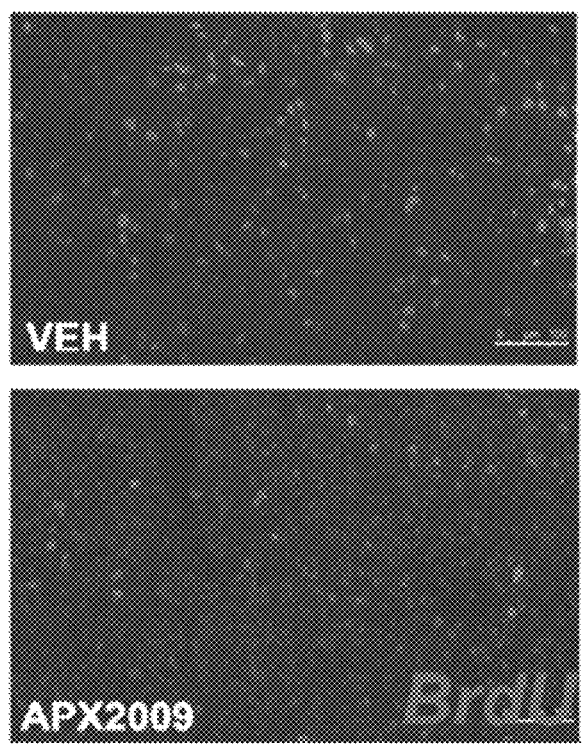
Figure 37C:
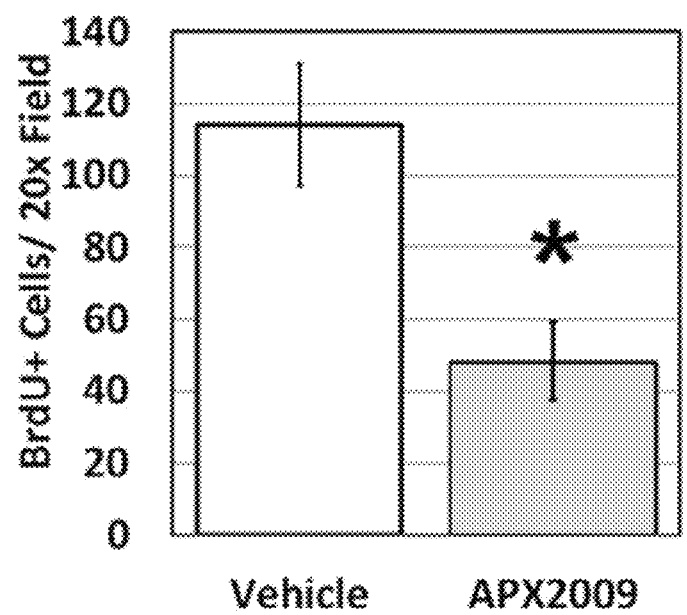
Figure 37D:
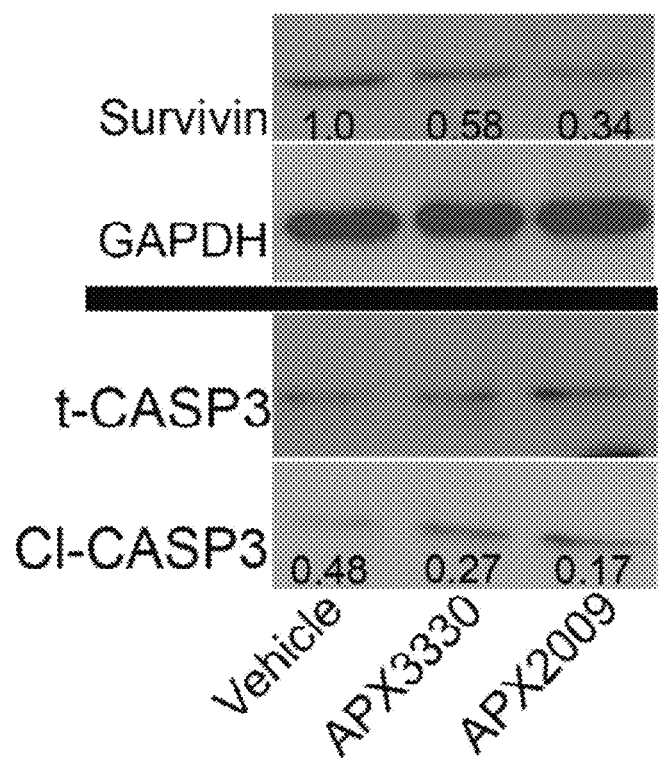

Prior to sacrifice, mice were injected with BrdU and BrdU incorporation was visualized and quantitated via red fluorescence. There is a dramatic 60% decrease in BrdU+ cells following treatment with APX2009 (FIGS. 37B & 37C; *p<0.05) confirming that inhibition of APE1/Ref-1 redox activity similarly reduces bladder cancer cell proliferation in vivo. Mechanistically, it was believed that the regulation of the transcriptional activity of NFκB and STATS by APE1/Ref-1 played a role in the observed tumor efficacy. In support of this, decreased expression of survival protein, survivin was observed in vitro as well as in vivo and could at least partially explain the decrease in tumor cell survival Immunoblotting for survivin protein in tumor tissues following in vivo treatment with APE1/Ref-1 inhibitors also demonstrated a significant reduction in survivin levels when compared to control tumors (FIG. 37D, p=0.016). Harvested tumors demonstrated a 42% reduction in survivin expression by APX3330 and a 64% reduction by APX2009, p<0.05, each inhibitor compared to vehicle. In addition, harvested tumors from mice treated with APX3330 and APX2009 demonstrated an increase in the ratio of cleaved caspase 3 (C1-CASP3) to total caspase 3 by immunoblotting, (p<0.05, each inhibitor compared to vehicle).

Figure 30A:
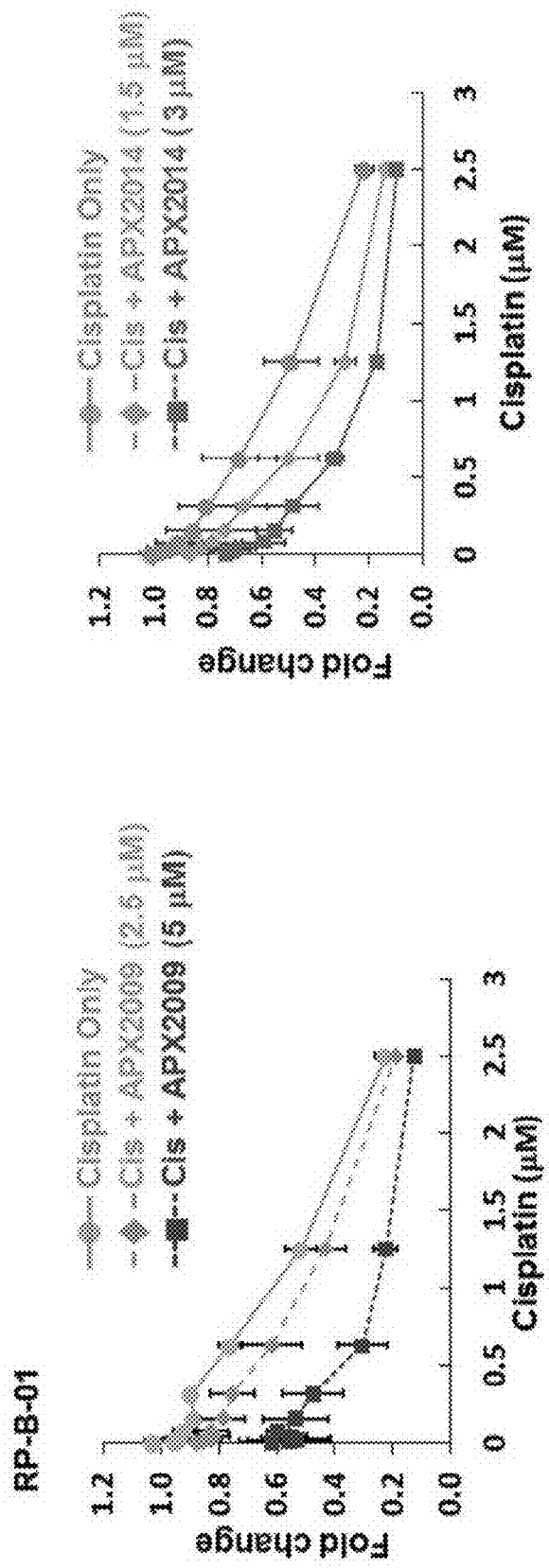
Figure 30B:
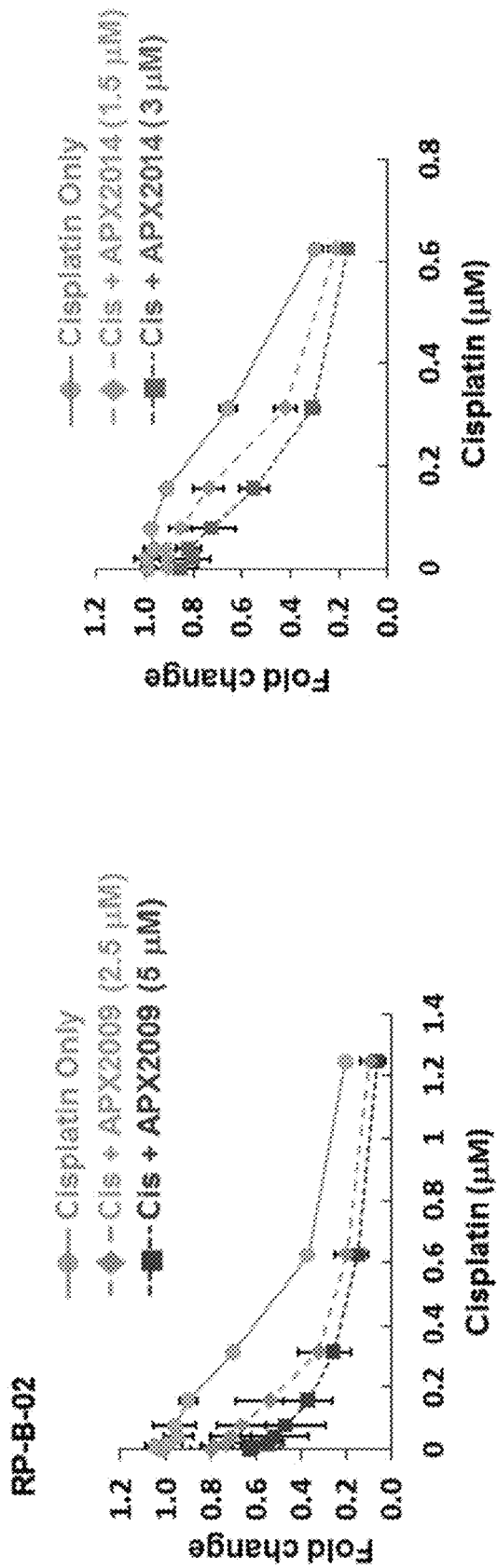

APE1/Ref-1 inhibition enhances cisplatin's therapeutic effect. Cisplatin is the standard of care for bladder cancer, but many patients' tumors are refractory to this therapy. Therefore, it was evaluated whether the combined treatment of cisplatin and APE1/Ref-1 inhibitors was more effective at reducing bladder cancer cell proliferation. To determine this, PDX lines, RP-B-01 and RP-B-02, as well as established cell line, T24, were treated with increasing concentrations of cisplatin in combination with APX compounds (FIGS. 30A-30C). Cell proliferation was assessed using Alamar blue 72 h after drug treatment. First, preferential sensitivity of RP-B-02 cells was confirmed by demonstrating that the RP-B-02 cells exhibited an $IC_{50}$ to cisplatin of 0.5 μM while the RP-B-01 cells exhibited an $IC_{50}$ to cisplatin of 1.44 μM (n=3; p<0.05). At the doses used in combination treatment, minimal reduction in bladder cancer cell proliferation was observed with APX2014 and APX2009 alone in all cell lines (~10-30%). However, when combined with increasing concentrations of cisplatin, a further reduction in cellular proliferation was observed. It was also determined using an ex vivo model of sensory neurons in culture measuring various embodiments of neurotoxicity that APX2009 is an effective small molecules that is neuroprotective against cisplatin and oxaliplatin-induced toxicity of sensory neurons. Interestingly, the effects of APE1/Ref-1 on cisplatin-induced cytotoxicity was more prevalent in the PDX lines (FIGS. 30A & 30B) than the T24 cells (FIG. 30C).

What is claimed is:

1. A method for inhibiting bladder cancer, the method comprising administering to a subject in need thereof an effective amount of an APE1/Ref-1 inhibitor selected from a group consisting of 3-[(5-(2,3-dimethoxy-6-methyl 1,4-benzoquinoyl)]-2-nonyl-2-propenoicacid (APX3330), [(2E)-2-[(3-methoxy-1,4-dioxo-1,4-dihydronaphthalen-2-yl)methylidene]-N,N-diethylpentanamide] (APX2009), and (2E)-2-[(3-methoxy-1,4-dioxo-1,4-dihydronapthalen-2-yl)methylidene]-N-methoxypentanamide] (APX2014), which selectively inhibits the redox function of Ape1/Ref- 1.

2. The method of claim 1 wherein the APE1/Ref-1 inhibitor is 3-[(5-(2,3-dimethoxy-6-methyl 1,4-benzoquinoyl)]-2-nonyl-2-propenoic acid (APX3330) and is administered in the effective amount of from about 10 µM to about 100 µM.

3. The method of claim 1 wherein the APE1/Ref-1 inhibitor is [(2E)-2[(3-methoxy-1,4-dioxo-1,4-dihydronaphthalen-2-yl)methylidene]-N,N-diethylpentanamide] (APX2009) and is administered in the effective amount of from about 1 µM to about 50 µM.

4. The method of claim 1 wherein the APE1/Ref-1 inhibitor is (2E)-2-[(3-methoxy-1,4-dioxo-1,4-dihydronapthalen-2-yl)methylidene]-N-methoxypentanamide] (APX2014) and is administered in the effective amount of from about 1 µM to about 50 µM.

5. The method of claim 1 wherein at least one additional therapeutic agent is administered to the subject.

6. The method of claim 5 wherein at least one additional therapeutic agent selected from the group consisting of melphalan, gemcitabine, cisplatin, thalidomide and its derivatives, and retinoic acid is administered to said subject.

7. The method of claim 6 wherein said additional therapeutic agent is cisplatin.

* * * * *

SEQUENCE LISTING

<160> NUMBER OF SEQ ID NOS: 2

<210> SEQ ID NO 1
<211> LENGTH: 19
<212> TYPE: DNA
<213> ORGANISM: Artificial Sequence
<220> FEATURE:
<223> OTHER INFORMATION: Synthetic

<400> SEQUENCE: 1
gtctggtacg actggagta                                                19

<210> SEQ ID NO 2
<211> LENGTH: 19
<212> TYPE: DNA
<213> ORGANISM: Artificial Sequence
<220> FEATURE:
<223> OTHER INFORMATION: Synthetic

<400> SEQUENCE: 2
cagatatact gtgccttca                                                19